US008420670B2

(12) United States Patent
Amberg et al.

(10) Patent No.: US 8,420,670 B2
(45) Date of Patent: Apr. 16, 2013

(54) 4-BENZYLAMINOQUINOLINES, PHARMACEUTICAL COMPOSITIONS CONTAINING THEM, AND THEIR USE IN THERAPY

(75) Inventors: Wilhelm Amberg, Ludwigshafen (DE); Michael Ochse, Ludwigshafen (DE); Wilfried Braje, Ludwigshafen (DE); Berthold Behl, Ludwigshafen (DE); Wilfried Hornberger, Ludwigshafen (DE); Mario Mezler, Ludwigshafen (DE); Charles W. Hutchins, Libertyville, IL (US)

(73) Assignees: Abbott Laboratories, Abbott Park, IL (US); Abbott GmbH & Co. KG, Wiesbaden (DE)

( * ) Notice: Subject to any disclaimer, the term of this patent is extended or adjusted under 35 U.S.C. 154(b) by 361 days.

(21) Appl. No.: 12/666,629

(22) PCT Filed: Aug. 22, 2008

(86) PCT No.: PCT/EP2008/061007

§ 371 (c)(1), (2), (4) Date: May 11, 2010

(87) PCT Pub. No.: WO2009/024611

PCT Pub. Date: Feb. 26, 2009

(65) Prior Publication Data

US 2010/0222346 A1 Sep. 2, 2010

Related U.S. Application Data

(60) Provisional application No. 60/965,724, filed on Aug. 22, 2007.

(51) Int. Cl.
*A61K 31/04* (2006.01)
*C07D 215/38* (2006.01)

(52) U.S. Cl.
USPC .......................................... 514/313; 546/159

(58) Field of Classification Search .................. 546/159; 514/313
See application file for complete search history.

(56) References Cited

U.S. PATENT DOCUMENTS 7,189,850 B2 3/2007 Ceccarelli et al.
7,427,612 B2 9/2008 Alberati-Giani et al.
7,462,617 B2 12/2008 Alberati-Giani et al.
2002/0169197 A1 11/2002 Egle et al.
2004/0026364 A1 2/2004 Kihara
2005/0124627 A1 6/2005 Schadt et al.
2005/0153963 A1 7/2005 Dargazanli et al.
2005/0153980 A1 7/2005 Schadt et al.
2005/0159450 A1 7/2005 Dargazanli et al.
2005/0267152 A1 12/2005 Bloomfield et al.
2006/0074105 A1 * 4/2006 Ware et al. .................... 514/313
2006/0223802 A1 10/2006 Dargazanli et al.
2006/0223861 A1 10/2006 Dargazanli et al.
2006/0223885 A1 10/2006 Dargazanli et al.
2006/0223886 A1 10/2006 Dargazanli et al.
2008/0070941 A1 3/2008 Dargazanli et al.
2008/0119486 A1 5/2008 Jolidon et al.

FOREIGN PATENT DOCUMENTS

EP 0258755 A1 3/1988
EP 1284257 A2 2/2003
WO 92/22533 A1 12/1992
WO 03031435 A1 4/2003
WO 03053942 A1 7/2003
WO 03055478 A1 7/2003
WO 03076420 A1 9/2003
WO 03087086 A2 10/2003
WO 03089411 A1 10/2003
WO 2004013100 A2 2/2004
WO 2004013101 A2 2/2004
WO 2004022528 A2 3/2004

(Continued)

OTHER PUBLICATIONS

Lindsley, C.W. et al., Progress Towards Validating the NMDA Receptor Hypofunction Hypothesis of Schizophrenia, Current Topics in Medicinal Chemistry, vol. 6, pp. 771-785 (2006).
Harsing, L.G. et al., Glycine Transporter Type-1 and its Inhibitors, Current Medicinal Chemistry, vol. 13, pp. 1017-1044 (2006).
Hashimoto, Kenji, Glycine Transporter Inhibitors as Therapeutic Agents for Schizophrenia, Recent Patents on CNS Drug Discovery, vol. 1, pp. 43-53 (2006).
Javitt, DC, Glutamate as a therapeutic target in psychiatric disorders, Molecular Psychiatry, vol. 9, pp. 984-997 (2004).
Lindsley, C.W. et al., Progress in the Preparation and Testing of Glycine Transporter Type-1 (GlyT1) Inhibitors, Current Topics in Medicinal Chemistry, vol. 6, pp. 1883-1896 (2006).

(Continued)

*Primary Examiner* — D M Seaman

(74) *Attorney, Agent, or Firm* — Lisa V. Mueller; Michael Best & Friedrich LLP

(57) ABSTRACT

The present invention relates to 4-benzylaminoquinolines of the formula (I) or physiologically tolerated salts thereof. The invention relates to pharmaceutical compositions comprising such quinolines, and the use of such quinolines for therapeutic purposes. The quinolines are GlyTI inhibitors.

(I)

$R^{6c}$, $R^{6d}$, $R^{6b}$, $R^{6e}$, $R^{6a}$, $R^1$, N, $R^2$, $R^3$, $R^{10}$, $R^9$, $R^7$, $R^8$, N, $R^4$, $R^5$

18 Claims, No Drawings

FOREIGN PATENT DOCUMENTS

| | | | |
|---|---|---|---|
| WO | 2004072034 | A1 | 8/2004 |
| WO | 2004096761 | A1 | 11/2004 |
| WO | 2004112787 | A1 | 12/2004 |
| WO | 2004113280 | A1 | 12/2004 |
| WO | 2004113301 | A1 | 12/2004 |
| WO | 2005014563 | A1 | 2/2005 |
| WO | 2005023260 | A1 | 3/2005 |
| WO | 2005023261 | A1 | 3/2005 |
| WO | 2005037781 | A2 | 4/2005 |
| WO | 2005037782 | A2 | 4/2005 |
| WO | 2005037783 | A2 | 4/2005 |
| WO | 2005037785 | A2 | 4/2005 |
| WO | 2005037792 | A1 | 4/2005 |
| WO | 2005040166 | A1 | 5/2005 |
| WO | 2005046601 | A2 | 5/2005 |
| WO | 2005049023 | A1 | 6/2005 |
| WO | 2005058317 | A1 | 6/2005 |
| WO | 2005058882 | A1 | 6/2005 |
| WO | 2005058885 | A2 | 6/2005 |
| WO | WO2006/034235 | * | 3/2006 |
| WO | 2006/121767 | A2 | 11/2006 |

OTHER PUBLICATIONS

Kinney, G.G., et al., "The glycerine transporter type 1 inhibitor N-[3-(4'-fluorophenyl)-3-(4'-phenylphenoxy) propyl] sarcosine potentiates NMDA receptor-mediated responses in vivo and produces an antipsychotic profile in rodent behavior," The Journal of Neuroscience, Aug. 20, 2003, 23(20), pp. 7586-7591.

Hashimoto, K., "Glycerine transport inhibitors for the treatment of schizophrenia," The Open Medicinal Chemistry Journal, 2010, 4, pp. 10-19.

Boulay, D., et al., "Characterization of SSR103800, a selective inhibitor of the glycine transporter-1 in models predictive of therapeutic activity in schizophrenia," Pharmacology, Biochemistry and Behavior, 91, (2008), pp. 47-58.

Pinard, E., et al., Selective gly T1 inhibitors: Discovery of [4-(3-Fluoro-5-trifluoremethylpyridin-2-yl)piperazin-1-yl]-[5-methanesulfonyl-2-((S)-2,2,2-trifluoro-1-methylethoxy)phenyl)methanone (RG1678), a Promising Novel Medicine to Treat Schizophrenia, J. Med. Chem. 2010, 53, pp. 4603-4614.

Lindsley, C.W., et al., Design, synthesis, and in vivo efficacy of glycine transporter-1 (GlyT1) inhibitors derived from a series of [4-Phenyl-1-(propylsulfonyl)piperidin-4-yl]nethyl benzamides, ChemMedChem, 2006, 1, pp. 807-811.

Sur, C., et al., "Glycine transporter 1 inhibitors and modulation of NMDA receptor-mediated excitatory neurotransmission," Current Drug Targets, 2007, 8, pp. 643-649.

Hashimoto, K., et al., "Phencyclidine-induced cognitive deficits in mice are improved by subsequent subchronic administration of the glycine transporter-1 inhibitor NFPS and D-serine," European Neuropsychopharmacology (2008), 18, pp. 414-421.

Tsai, G., et al., "Gene knockout of glycine transporter 1: characterization of the behavioral phenotype," PNAS, Jun. 1, 2004, vol. 101, No. 22, pp. 8485-8490.

* cited by examiner

4-BENZYLAMINOQUINOLINES, PHARMACEUTICAL COMPOSITIONS CONTAINING THEM, AND THEIR USE IN THERAPY

CROSS-REFERENCE TO RELATED APPLICATIONS

This is the national stage of International Patent Application No. PCT/EP2008/061007, filed on Aug. 22, 2008, which claims the benefit of U.S. Provisional Patent Application No. 60/965,724, filed on Aug. 22, 2007, the contents of all of which are incorporated herein by reference.

BACKGROUND OF THE INVENTION

The present invention relates to 4-benzylaminoquinolines, pharmaceutical compositions comprising such quinolines, and the use of such quinolines for therapeutic purposes. The quinolines are GlyT1 inhibitors.

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

US 200426364

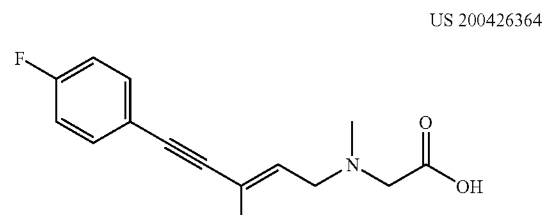

US 2002169197

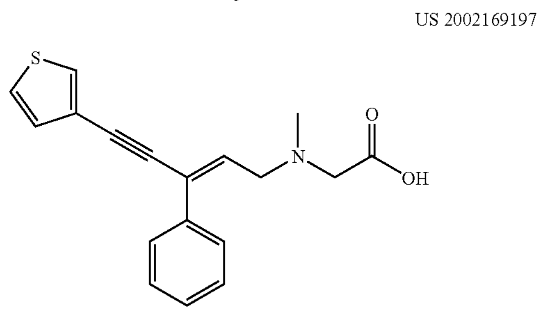

EP 1 284 257

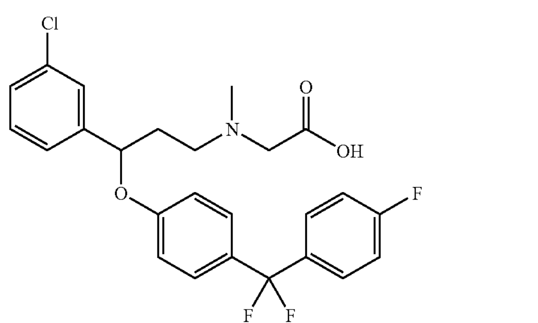

WO 2003053942

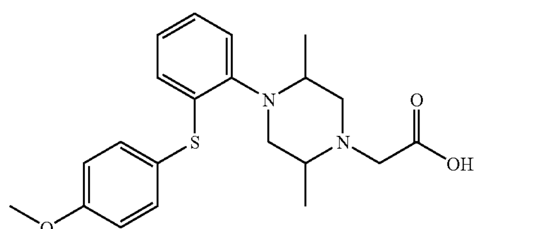

WO 2004096761

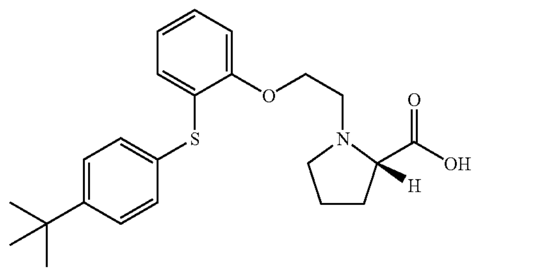

-continued
WO 2003031435
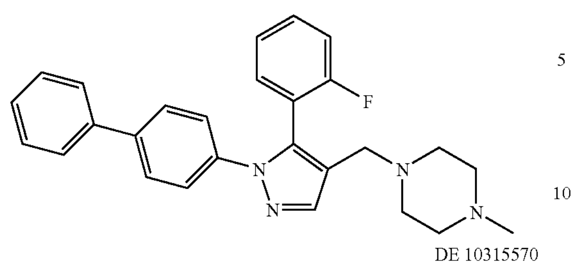
DE 10315570
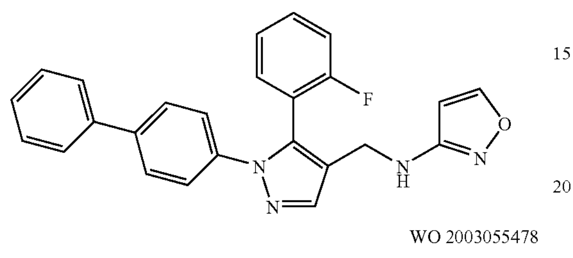
WO 2003055478
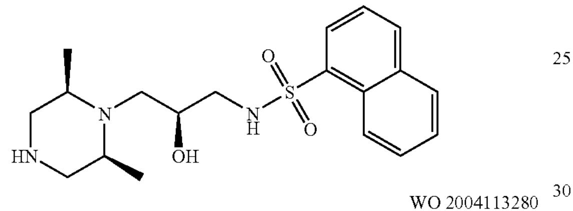
WO 2004113280
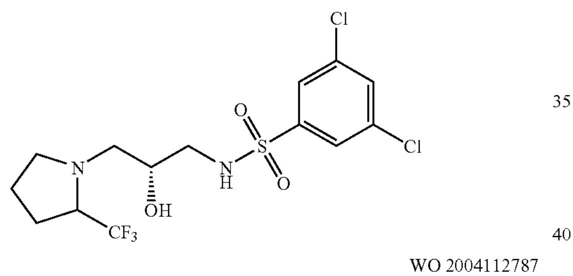
WO 2004112787
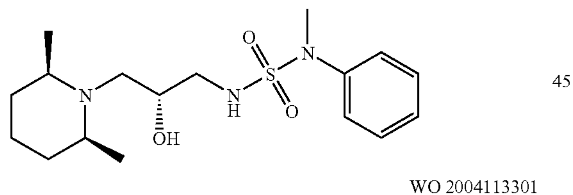
WO 2004113301
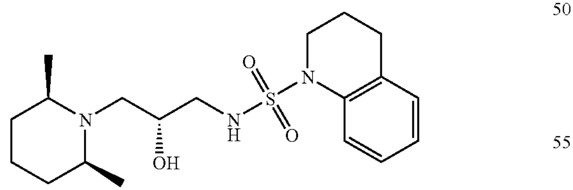
WO 2005049023
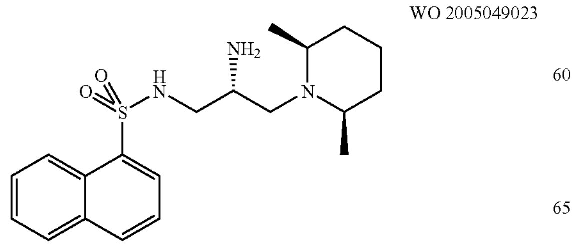
-continued
WO 2003089411
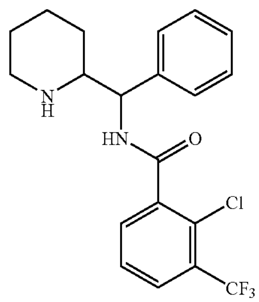
WO 2004013100
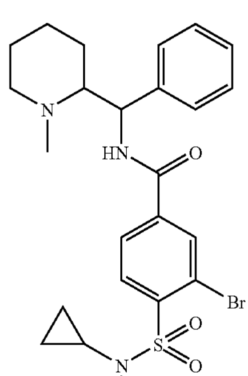
WO 2004013101
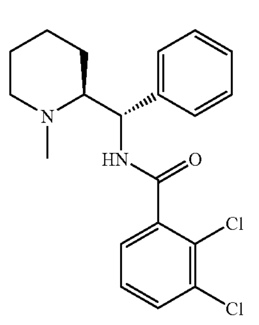
WO 2005037783
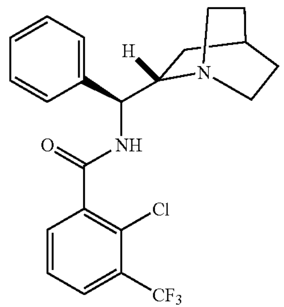
WO 2005037792
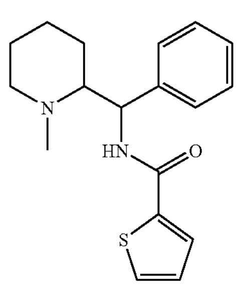

WO 2005037781
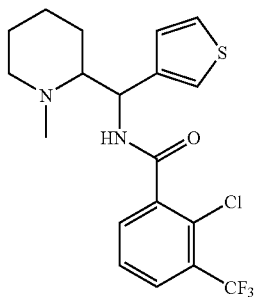
WO 2005037782
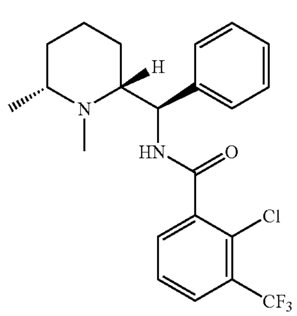
WO 2005037785
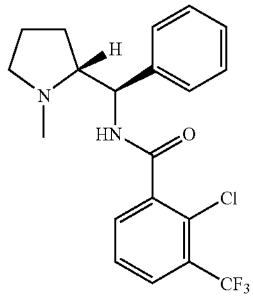
WO 2005037785
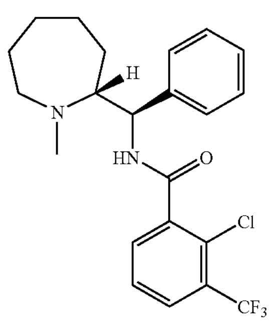
WO 2004072034
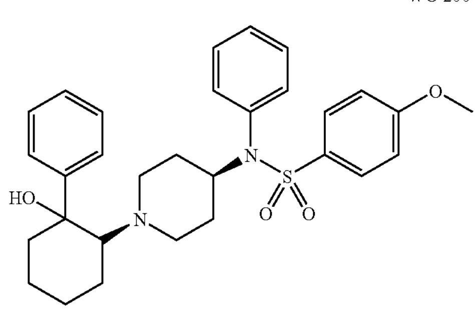
WO 2005014563
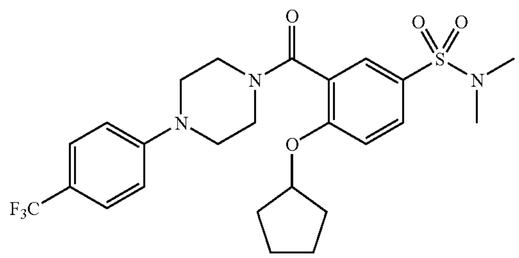
WO 2005023260
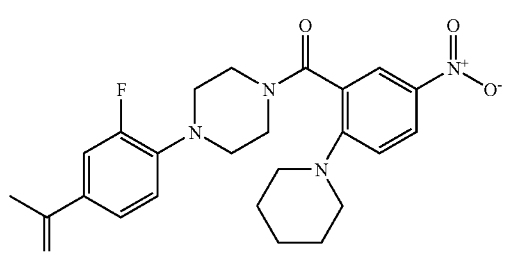
WO 2005023261
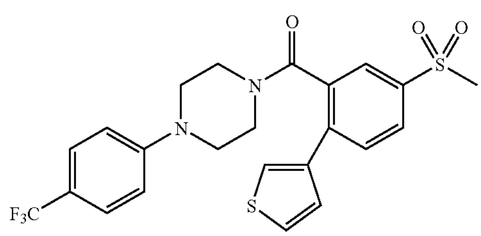
WO 2005040166
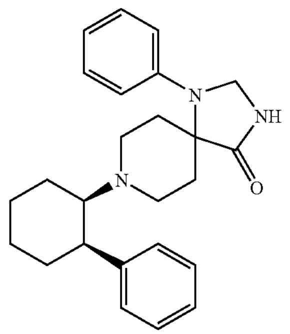
WO 2005058882
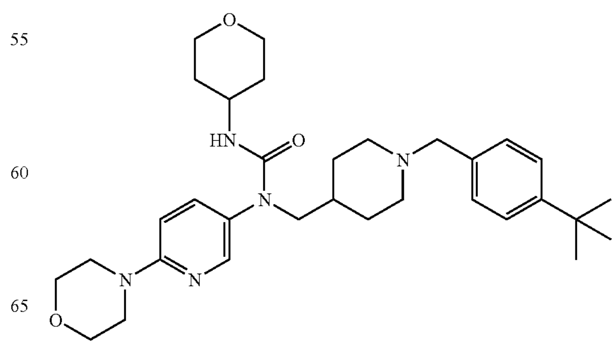

-continued

WO 2005058885

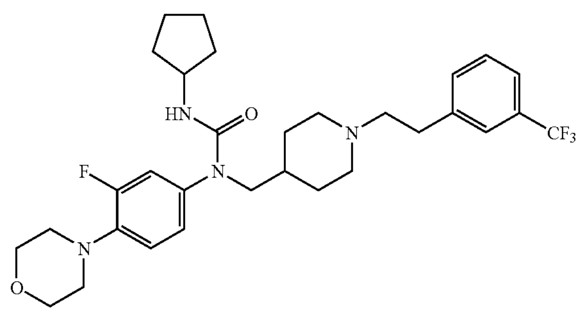

WO 2005058317

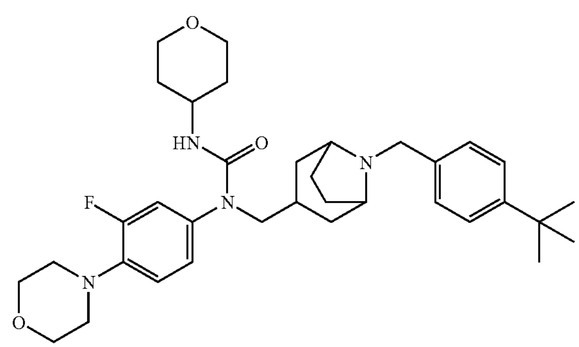

WO 2005046601

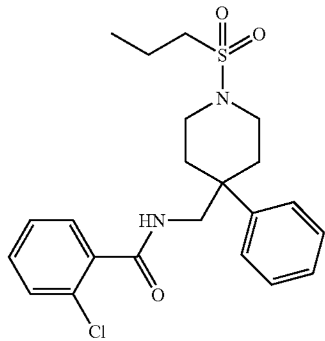

WO 2003087086

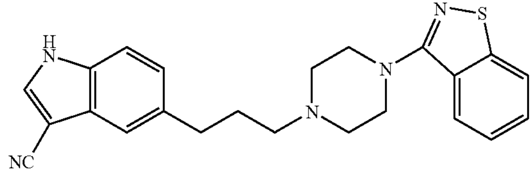

WO 2003076420

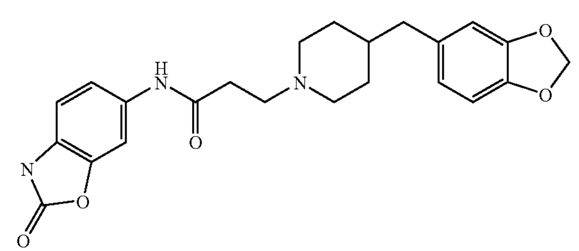

-continued

WO 2004022528

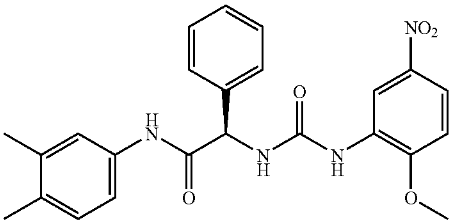

(see also Hashimoto K., Recent patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

It was one object of the present invention to provide further glycine transporter inhibitors.

SUMMARY OF THE INVENTION

The present invention relates to 4-benzylaminoquinolines of the formula (I)

(I)

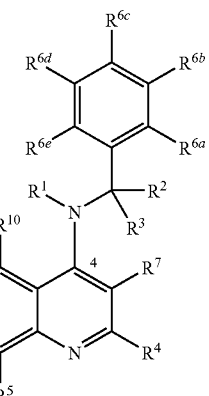

wherein $R^1$ is hydrogen, alkyl, aryl;

$R^2$, $R^3$ are independently hydrogen, alkyl, $C_3$-$C_{12}$-cycloalkyl, aryl, aminocarbonyl, amino or heterocyclyl;

$R^4$ is alkyl, halogenated alkyl, alkoxy, dialkylamino, arylamino or sulfonylamino;

$R^5$ is hydrogen, halogen, alkyl, hydroxy, alkoxy, substituted alkoxy, aryloxy, heteroaryloxy, alkylthio, alkylsulfinyl, alkylsulfonyl, aminosulfonyl, alkylaminosulfonyl, dialkylaminosulfonyl, arylaminosulfonyl, amino, substituted amino or heterocyclyl;

$R^{6a}$, $R^{6b}$, $R^{6c}$, $R^{6d}$, $R^{6e}$ are independently hydrogen, halogen, alkyl, halogenated alkyl, hydroxyalkyl, alkoxycarbonyl, (halogenated alkoxy)carbonyl, cyano, alkoxy, halogenated alkoxy, aryl, alkylthio, (halogenated alkyl)thio, nitro, amino, alkylamino, (halogenated alkyl)amino, dialkylamino, di-(halogenated alkyl)amino, alkylcarbonylamino, (halogenated alkyl)carbonylamino, alkylsulfonylamino, (halogenated alkyl)sulfonylamino or arylsulfonylamino; or $R^{6a}$, $R^2$ together are alkylene; or $R^{6a}$ and $R^{6b}$ or $R^{6b}$ and $R^{6c}$ together with the carbon atoms to which they are attached form an anellated aryl ring; or together are alkylenedioxo; and $R^7$, $R^8$, $R^9$, $R^{19}$ are independently hydrogen, halogen, alkyl or alkoxy, wherein alkyl, alkylene, alkoxycarbonyl, aminocarbonyl, aryl, alkoxy, alkylenedioxo, aryloxy, heteroaryloxy, alkylthio, alkylsulfinyl, alkylsulfonyl, aminosulfonyl, alkylaminosulfonyl, dialkylaminosulfonyl, arylaminosulfonyl, amino, alkylamino, dialkylamino, alkylcarbonylamino, arylamino, sulfonylamino, alkylsulfonylamino, arylsulfonylamino and heterocyclyl may be substituted, or a physiologically tolerated salt thereof.

Said compounds, i.e., the 4-benzylaminoquinolines and their physiologically tolerated acid addition salts, are glycine transporter inhibitors and thus uselful as pharmaceuticals.

The present invention thus also relates to pharmaceutical compositions which comprises an inert carrier and a compound of formula (I).

In particular, said compounds, i.e., the 4-benzylaminoquinolines and their physiologically tolerated acid addition salts, are inhibitors of the glycine transporter GlyT1.

The present invention thus further relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder.

The present invention thus further relates to the use of the compounds of formula (I) in the manufacture of a medicament for treating a neurologic or psychiatric disorder and corresponding methods of treating said disorders.

In one aspect of the present invention the following compounds and their physiologically tolerated salts are excluded, but not their use as defined herein:

a) 4'-[[(2-methyl-4-quinolinyl)amino]methyl]-[1,1'-biphenyl]-2-carboxylic acid, 1,1-dimethylethyl ester
b) 2-methyl-N-[[2'-[1-(triphenylmethyl)-1H-tetrazol-5-yl][1,1'-biphenyl]-4-yl]methyl]-4-quinolinamine,
c) 2-methyl-N-[[3'-(1H-tetrazol-5-yl)[1,1'-biphenyl]-4-yl]methyl]-4-quinolinamine,
d) 4'-[[(2-methyl-4-quinolinyl)amino]methyl]-[1,1'-biphenyl]-2-carboxylic acid,
e) 4'-[[(2-methyl-4-quinolinyl)amino]methyl]-[1,1'-biphenyl]-3-carboxylic acid, 1,1-dimethylethyl ester
f) 2-methyl-N-[[2'-(1H-tetrazol-5-yl)[1,1'-biphenyl]-4-yl]methyl]-4-quinolinamine,
g) 4'-[[(8-methoxy-2-methyl-4-quinolinyl)amino]methyl]-[1,1'-biphenyl]-2-carboxylic acid,
h) 8-methoxy-2-methyl-N-[[2'-(1H-tetrazol-5-yl)[1,1'-biphenyl]-4-yl]methyl]-4-quinolinamine,
i) 4'-[[(2-methyl-4-quinolinyl)amino]methyl]-N-(methylsulfonyl)-[1,1'-biphenyl]-2-carboxamide,
j) 4'-[[(2-methyl-4-quinolinyl)amino]methyl]-[1,1'-biphenyl]-2-carboxylic acid,
k) 4'-[[(2-methyl-4-quinolinyl)amino]methyl]-[1,1'-biphenyl]-2-carboxylic acid, methyl ester
l) N-[(2-methylphenyl)methyl]-8-methoxy-2-methyl-4-quinolinamine,
m) N-[(2-methoxyphenyl)methyl]-8-methoxy-2-methyl-4-quinolinamine,
n) N-[(2-ethylphenyl)methyl]-8-methoxy-2-methyl-4-quinolinamine,
o) N-[(2-bromophenyl)methyl]-8-methoxy-2-methyl-4-quinolinamine,
p) N-[(2,6-dichlorophenyl)methyl]-8-methoxy-2-methyl-4-quinolinamine,
q) N-[(2,6-dimethoxyphenyl)methyl]-8-methoxy-2-methyl-4-quinolinamine,
r) N-[(2,6-dimethylphenyl)methyl]-8-methoxy-2-methyl-4-quinolinamine,
s) N-[(2,3-dimethylphenyl)methyl]-8-methoxy-2-methyl-4-quinolinamine,
t) N-[(2,4-dimethylphenyl)methyl]-8-methoxy-2-methyl-4-quinolinamine,
u) N-[(2,5-dimethylphenyl)methyl]-8-methoxy-2-methyl-4-quinolinamine,
v) N-[(2-chlorophenyl)methyl]-8-methoxy-2-methyl-4-quinolinamine,
w) N-[(2-fluorophenyl)methyl]-8-methoxy-2-methyl-4-quinolinamine,
x) N-[(2-chloro-6-fluorophenyl)methyl]-8-methoxy-2-methyl-4-quinolinamine,
y) N-[(2,6-difluorophenyl)methyl]-8-methoxy-2-methyl-4-quinolinamine,
z) N-[[2-(trifluoromethyl)phenyl]methyl]-8-methoxy-2-methyl-4-quinolinamine,
aa) 4-[[(8-methoxy-2-methyl-4-quinolinyl)amino]methyl]-3-methyl-phenol,
ab) 4-[(p-chlorobenzyl)amino]-quinaldine,
ac) N-[(1S)-1-phenylethyl]-2-methyl-4-quinolinamine,
ad) N-(phenylmethyl)-2-methyl-4-quinolinamine,
ae) 4-[[1-(3,4-dimethoxyphenyl)hexyl]amino]-2-methyl-8-quinolinol,
af) 4-[[1-(2-hexyl-4,5-dimethoxypheny)ethyl]amino]-2-methyl-8-quinolinol,
ag) 4-[[1-(3,4-dimethoxyphenyl)hexyl]amino]-2-methyl-8-quinolinol,
ah) 4-[[1-(2-hexyl-4,5-dimethoxyphenyl)ethyl]amino]-2-methyl-4-quinolinol,
ai) N-[1-(3,4-dimethoxyphenyl)hexyl]-8-methoxy-2-methyl-4-quinolinamine,
aj) N-[1-(2-hexyl-4,5-dimethoxyphenyl)ethyl]-8-methoxy-2-methyl-4-quinolinamine.

DETAILED DESCRIPTION OF THE INVENTION

Provided that the 4-benzylaminoquinolines of the formula (I) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) and/or of their salts.

According to one embodiment, an enantiomer of the 4-benzylaminoquinolines of the present invention has the following formula (Ia):

(Ia)

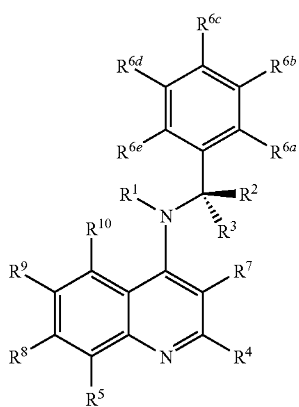

wherein $R^1$, $R^2$, $R^3$, $R^4$, $R^5$, $R^{6a}$, $R^{6b}$, $R^{6c}$, $R^{6d}$, $R^{6e}$, $R^7$, $R^8$, $R^9$, $R^{10}$ are as defined herein.

According to a further embodiment, an enantiomer of the 4-benzylaminoquinolines of the present invention has the following formula (Ib):

(Ib)

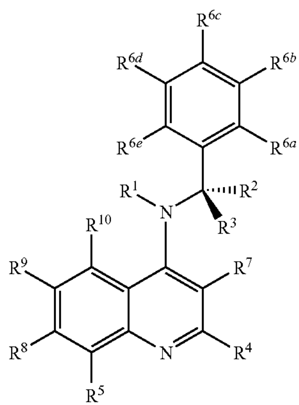

wherein $R^1$, $R^2$, $R^3$, $R^4$, $R^5$, $R^{6a}$, $R^{6b}$, $R^{6c}$, $R^{6d}$, $R^{6e}$, $R^7$, $R^8$, $R^9$, $R^{10}$ are as defined herein.

The physiologically tolerated salts of the 4-benzylaminoquinolines of the formula (I) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-campher sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$—$C_m$ indicates in each case the possible number of carbon atoms in the group.

Unless indicated otherwise, the term "substituted" means that a radical is substituted with 1, 2 or 3, especially 1, substituent selected from the group consisting of halogen, $C_1$-$C_4$-alkyl, $C_1$-$C_4$-alkenyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl$)_2$, $SO_2N$—($C_1$-$C_6$-alkyl$)_2$, $NH_2$, NH—$C_1$-$C_6$-alkyl, N—($C_1$-$C_6$-alkyl$)_2$, NH—($C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2NH$—$C_6$-$C_{12}$-aryl, CONH—$C_5$-$C_{12}$-hetaryl, $SO_2NH$—$C_5$-$C_{12}$-hetaryl, $SO_2$—$C_6$-$C_{12}$-aryl, NH—$SO_2$—$C_6$-$C_{12}$-aryl, NH—CO—$C_6$-$C_{12}$-aryl, NH—$SO_2$—$C_5$-$C_{12}$-hetaryl and NH—CO—$C_5$-$C_{12}$-hetaryl, wherein aryl and hetaryl in turn may be unsubstituted or substituted with 1, 2 oder 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or isopropyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2- hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, iso-butylaminomethyl or tert-butylaminomethyl.

Di-$C_1$-$C_6$-alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, iso-propylsulfonylaminomethyl, n-butylsulfonylaminomethyl, 2-butylsulfonylaminomethyl, iso-butylsulfonylaminomethyl or tert-butylsulfonylaminomethyl.

($C_6$-$C_{12}$-aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl) amino group, in particular a ($C_6$-$C_{12}$-aryl-$C_1$-$C_2$-alkyl)amino group, such as in benzylaminomethyl.

$C_3$-$C_{12}$-heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl or N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

$C_1$-$C_6$-alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl and pivaloyl.

$C_6$-$C_{12}$-arylcarbonyl is a radical of the formula R—C(O)—, wherein R is an aryl radical having from 6 to 12 carbon atoms as defined herein. Examples include benzoyl.

$C_1$-$C_6$-alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl (2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_1$-$C_4$-Alkylene is straight-chain or branched alkylene group having from 1 to 4 carbon atoms. Examples include methylene and ethylene.

$C_6$-$C_{12}$-Aryl is a 6- to 12-membered, in particular 6- to 10-membered, aromatic cyclic radical. Examples include phenyl and naphthyl.

Hydroxy is —OH.

$C_1$-$C_6$-Alkoxy is a a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, iso-butoxy (2-methylpropoxy), tert.-butoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$ alkoxy is an alkoxy radical having from 1 to 4, preferably 1 or 2 carbon atoms as defined herein, wherein one hydrogen atom is replaced by an amino group. Examples include 2-amino-ethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, iso-propylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, isopropylcarbonylaminomethoxy, n-butylcarbonylaminomethoxy, 2-butylcarbonylaminomethoxy, isobutylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(iso-butylcarbonylamino)ethoxy and 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, iso-propoxycarbonylaminomethoxy, n-butoxycarbonylaminomethoxy, 2-butoxycarbonylaminomethoxy, iso-butoxycarbonylaminomethoxy, tert-butoxycarbonylaminomethoxy, 2-(methoxycarbonylamino)ethoxy, 2-(ethoxycarbonylamino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(isobutoxycarbonylamino)ethoxy and 2-(tert-butoxycarbonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy and 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy and 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_2$-Alkylenedioxo is a radical of the formula —O—R—O—, wherein R is a straight-chain or branched alkylene group having 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—$S(O)_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylsulfonyl is a radical of the formula R—$S(O)_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—$S(O)_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—$S(O)_2$—, wherein R is $C_3$-$C_{12}$-heterocyclyl as defined herein.

Aminosulfonyl is $NH_2$—$S(O)_2$—.

$C_1$-$C_6$-Alkylaminosulfonyl is a radical of the formula R—NH—$S(O)_2$— wherein R is an alkyl radical having from 1 to 6, preferably from 1 to 4 carbon atoms as defined herein. Examples include methylaminosulfonyl, ethylaminosulfonyl, n-propylaminosulfonyl, isopropylaminosulfonyl, n-butylaminosulfonyl, 2-butylaminosulfonyl, iso-butylaminosulfonyl and tert-butylaminosulfonyl.

Di-$C_1$-$C_6$-alkylaminosulfonyl is a radical of the formula RR'N—$S(O)_2$— wherein R and R' are independently of each other an alkyl radical having from 1 to 6, preferably from 1 to 4 carbon atoms as defined herein. Examples include dimethylaminosulfonyl, diethylaminosulfonyl and N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is $NH_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino and tert-butylamino.

(Halogenated $C_1$-$C_6$-Alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different hydrogen atoms.

Di-$C_1$-$C_6$-Alkylamino is a radical of the formula RR'N— wherein R and R' are independently of each other an alkyl radical having from 1 to 6, in particular from 1 to 4 carbon atoms as defined herein. Examples include dimethylamino, diethylamino and N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different hydrogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido (methylcarbonylamino), propionamido, n-butyramido, 2-methylpropionamido (isopropylcarbonylamino), 2,2-dimethylpropionamido and the like.

(Halogenated $C_1$-$C_6$-Alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, isopropylsulfonylamino, n-butylsulfonylamino, 2-butylsulfonylamino, iso-butylsulfonylamino and tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —$NO_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C-bound 3-4-membered, saturated rings, such as 2-oxiranyl, 2-oxetanyl, 3-oxetanyl, 2-aziridinyl, 3-thiethanyl, 1-azetidinyl and 2-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl and 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl and tetrahydro-1,2-oxazin-6-yl;

N-bound, 5-membered, saturated rings, such as tetrahydropyrrol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl and tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl(morpholin-1-yl) and tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro- 1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl and 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl and 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl and 2,3-dihydrothiazol-3-yl; N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihdro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl and 3,4-dihydropyrimidin-3-yl.

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl and tetrazol-5-yl.

C-bound, 6-membered, heteroaromatic rings, such as pyridin-2-yl, pyridin-3-yl, pyridin-4-yl (4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl and 1,2,4,5-tetrazin-3-yl.

N-bound, 5-membered, heteroaromatic rings, such as pyrrol-1-yl, pyrazol-1-yl, imidazol-1-yl, 1,2,3-triazol-1-yl, 1,2,4-triazol-1-yl and tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydrochinolinyl, dihydroisoquinolinyl, chromenyl and chromanyl.

With respect to their capability of inhibiting glycine transporter 1, the variables $R^1$, $R^2$, $R^3$, $R^4$, $R^5$, $R^{6a}$, $R^{6b}$, $R^{6c}$, $R^{6d}$, $R^{6e}$, $R^7$, $R^8$, $R^9$ and $R^{10}$ preferably have the following meanings which, when taken alone or in combination, represent particular embodiments of the 4-benzylaminoquinolines of the formula (I).

$R^1$ is hydrogen, $C_1$-$C_6$-alkyl, or $C_6$-$C_{12}$-aryl. Preferably, $R^1$ is hydrogen.

$R^2$ and $R^3$ are independently hydrogen, $C_1$-$C_6$-alkyl, substituted $C_1$-$C_4$-alkyl, $C_3$-$C_{12}$-cycloalkyl, $C_6$-$C_{12}$-aryl, aminocarbonyl, amino, or optionally substituted $C_3$-$C_{12}$-heterocyclyl.

More preferably, $R^2$ and $R^3$ are independently hydrogen, $C_1$-$C_6$-alkyl (e.g. methyl), substituted $C_1$-$C_4$-alkyl, $C_3$-$C_{12}$-cycloalkyl (e.g. cyclopropyl), aminocarbonyl (e.g. aminocarbonyl), or optionally substituted $C_3$-$C_{12}$-heterocyclyl (e.g. piperidin-2-yl, N-methylpiperidin-2-yl, N-allylpiperidin-2-yl, pyridin-4-yl, N-methylimidazol-2-yl). Preferred alkyl substitutents are $C_1$-$C_6$-alkoxy, amino (e.g. aminomethyl), $C_1$-$C_6$-alkylamino (e.g. isopropylaminomethyl), di-$C_1$-$C_6$-alkylamino (e.g. dimethylaminomethyl), ($C_6$-$C_{12}$-aryl-$C_1$-$C_4$-alkyl)amino (e.g. benzylaminomethyl), $C_1$-$C_6$-alkylcarbonylamino, $C_1$-$C_6$-alkylsulfonylamino or $C_3$-$C_{12}$-heterocyclyl (e.g. N-pyrrolidinylmethyl, N-piperidinylmethyl, N-morpholinylmethyl). More preferred alkyl substitutents are amino (e.g. aminomethyl), $C_1$-$C_6$-alkylamino (e.g. isopropylaminomethyl), di-$C_1$-$C_6$-alkylamino (e.g. dimethylaminomethyl), ($C_6$-$C_{12}$-aryl-$C_1$-$C_4$-alkyl)amino (e.g. benzylaminomethyl) or $C_3$-$C_{12}$-heterocyclyl (e.g. N-pyrrolidinylmethyl, N-piperidinylmethyl, N-morpholinylmethyl). Preferred heterocyclyl substituents are $C_1$-$C_4$-alkyl and $C_2$-$C_4$-alkenyl.

According to a particular embodiment, $R^2$ is hydrogen or $C_1$-$C_3$-alkyl, in particular hydrogen. $R^3$ is defined as above. Preferably, $R^3$ is $C_1$-$C_2$-alkyl substituted with amino (e.g. aminomethyl), $C_1$-$C_4$-alkylamino (e.g. isopropylaminomethyl), di-$C_1$-$C_4$-alkylamino (e.g. dimethylaminomethyl), ($C_6$-$C_{12}$-aryl-$C_1$-$C_2$-alkyl)amino (e.g. benzylaminomethyl) or $C_3$-$C_{12}$-heterocyclyl (e.g. N-pyrrolidinylmethyl, N-piperidinylmethyl, N-morpholinylmethyl), or $R^3$ is optionally substituted $C_3$-$C_{12}$-heterocyclyl (e.g. piperidin-2-yl, N-methylpiperidin-2-yl, N-allylpiperidin-2-yl). More preferably, $R^3$ is aminomethyl (e.g. aminomethyl), $C_1$-$C_4$-alkylaminomethyl (e.g. isopropylaminomethyl), di-$C_1$-$C_4$-alkylaminomethyl (e.g. dimethylaminomethyl), ($C_6$-$C_{12}$-aryl-$C_1$-$C_2$-alkyl)aminomethyl (e.g. benzylaminomethyl) or $C_3$-$C_{12}$-heterocyclylmethyl (e.g. N-pyrrolidinylmethyl, N-piperidinylmethyl, N-morpholinylmethyl), or $R^3$ is piperidinyl or piperidinyl substituted with $C_1$-$C_4$-alkyl or $C_2$-$C_4$-allyl.

$R^4$ is $C_1$-$C_6$-alkyl, halogenated $C_1$-$C_6$-alkyl, $C_1$-$C_6$-alkoxy, di-($C_1$-$C_6$-alkyl)amino, $C_6$-$C_{12}$-arylamino or sulfonylamino.

More preferably, $R^4$ is methyl or dimethylamino.

$R^5$ is hydrogen, halogen, $C_1$-$C_6$-alkyl, hydroxy, $C_1$-$C_6$-alkoxy, substituted $C_1$-$C_4$-alkoxy, $C_6$-$C_{12}$-aryloxy, $C_6$-$C_{12}$-heteroaryloxy, $C_1$-$C_6$-alkylthio, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, (optionally substituted $C_6$-$C_{12}$-aryl)aminosulfonyl, amino, substituted amino or optionally substituted $C_3$-$C_{12}$-heterocyclyl. Preferred aryl substituents are halogen, in particular fluoro, $C_1$-$C_4$-alkyl, $C_1$-$C_4$-haloalkyl, $C_1$-$C_4$-alkoxy, in particular ethoxy, and $C_1$-$C_4$-haloalkoxy, in particular chloromethoxy. Preferred heterocyclyl substituents are halogen, in particular fluoro and chloro, $C_1$-$C_4$-alkyl, $C_1$-$C_4$-haloalkyl, $C_1$-$C_4$-alkoxy, in particular ethoxy, and $C_1$-$C_4$-haloalkoxy, in particular chloromethoxy.

According to a particular embodiment, $R^5$ is hydrogen or halogen (e.g. fluoro, chloro), preferably hydrogen.

According to a further particular embodiment, $R^5$ is hydroxy (e.g. hydroxy), $C_1$-$C_6$-alkoxy (e.g. methoxy, n-propyloxy, isopropyloxy, 2-methylpropyloxy), halogenated $C_1$-$C_4$-alkoxy (e.g. trifluoromethoxy), $C_6$-$C_{12}$-aryloxy (e.g. phenoxy) or $C_6$-$C_{12}$-heteroaryloxy (e.g. pyridin-2-yloxy), preferably $C_1$-$C_2$-alkoxy.

According to a further particular embodiment, $R^5$ is a group of the formula (II):

$$-A^1-A^2-A^3-R^{5a} \quad \text{(II)}$$

wherein $A^1$ is O, $NR^{5b}$;

$A^2$ is optionally substituted $C_1$-$C_4$-alkylene;

$A^3$ is O, $NR^{5b}$;

$R^{5a}$ is hydrogen, $C_1$-$C_4$-alkyl, $C_1$-$C_4$-alkylcarbonyl, $C_6$-$C_{12}$-arylcarbonyl, $C_1$-$C_6$-alkoxycarbonyl, halogenated $C_1$-$C_4$-alkoxycarbonyl, $C_6$-$C_{12}$-aryloxycarbonyl, $C_1$-$C_6$-alkylaminocarbonyl, (halogenated $C_1$-$C_4$-alkyl)aminocarbonyl, $C_6$-$C_{12}$-arylaminocarbonyl, $C_1$-$C_6$-alkylsulfonyl, (halogenated $C_1$-$C_6$-alkyl)sulfonyl, $C_6$-$C_{12}$-arylsulfonyl, ($C_6$-$C_{12}$-aryl-$C_1$-$C_4$-alkyl)sulfonyl, $C_3$-$C_{12}$-heterocyclylsulfonyl, $C_6$-$C_{12}$-aryl; and $R^{5b}$ is hydrogen, $C_1$-$C_4$-alkyl; or $R^{5a}$ and $R^{5b}$ together with the nitrogen atom to which they are attached are $C_3$-$C_{12}$-heterocyclyl.

Substituted $C_1$-$C_4$-alkylene is preferably $C_1$-$C_4$-alkylene substituted with halogen, $C_1$-$C_4$-alkyl or $C_1$-$C_3$-alkoxy.

$A^1$ in formula (II) is preferably oxygen.

$A^2$ in formula (II) is preferably $C_1$-$C_2$-alkylene.

$A^3$ in formula (II) is preferably $NR^{5b}$.

$R^{5a}$ and $R^{5b}$ in formula (II) are independently as defined above. $R^{5a}$ is preferably $C_1$-$C_4$-alkylsulfonyl. $R^{5b}$ is preferably hydrogen.

According to a further particular embodiment, $R^5$ is substituted $C_1$-$C_4$-alkoxy, such as $C_1$-$C_4$-alkoxy substituted with $C_1$-$C_6$-alkoxy (e.g. 2-methoxyethoxy), amino (e.g. 2-aminoethoxy), di-$C_1$-$C_6$-alkylamino (e.g. 2-(dimethylamino)ethoxy), $C_1$-$C_6$-alkylcarbonylamino (e.g. 2-(methylcarbonylamino)ethoxy, 2-(isopropylcarbonylamino)ethoxy), $C_6$-$C_{12}$-arylcarbonylamino (e.g. 2-(benzoylamino)ethoxy), $C_1$-$C_6$-alkoxycarbonylamino (e.g. 2-(t-butyloxycarbonylamino)ethoxy), $C_3$-$C_{12}$-heterocyclyl (e.g. 2-(N-pyrrolidinyl)ethoxy, 2-(N-morpholinyl)ethoxy, 2-(N-imidazolyl)ethoxy), $C_1$-$C_6$-alkylsulfonylamino (e.g. 2-(methylsulfonylamino)ethoxy, 2-(ethylsulfonylamino)ethoxy, 2-[(2-methylpropyl)sulfonylamino]ethoxy), (halogenated $C_1$-$C_4$-alkyl)sulfonylamino (e.g. 2-(trifluoromethylsulfonylamino)ethoxy), $C_6$-$C_{12}$-arylsulfonylamino (e.g. 2-(phenylsulfonylamino)ethoxy, 2-(naphthylsulfonylamino)ethoxy), ($C_6$-$C_{12}$-aryl-$C_1$-$C_4$-alkyl)sulfonylamino (e.g. 2-(benzylsulfonylamino)ethoxy), $C_3$-$C_{12}$-heterocyclylsulfonylamino (e.g. 2-(pyridin-3-yl-sulfonylamino)ethoxy) or $C_6$-$C_{12}$-aryl (e.g. benzyloxy); preferably, substituted $C_1$-$C_2$-alkoxy, such as $C_1$-$C_2$-alkoxy substituted with $C_1$-$C_4$-alkoxy (e.g. 2-methoxyethoxy), amino (e.g. 2-aminoethoxy), di-$C_1$-$C_4$-alkylamino (e.g. 2-(dimethylamino)ethoxy), $C_1$-$C_4$-alkylcarbonylamino (e.g. 2-(methylcarbonylamino)ethoxy, 2-(isopropylcarbonylamino)ethoxy), $C_6$-$C_{12}$-arylcarbonylamino (e.g. 2-(benzoylamino)ethoxy), $C_1$-$C_4$-alkoxycarbonylamino (e.g. 2-(t-butyloxycarbonylamino)ethoxy), $C_3$-$C_{12}$-heterocyclyl (e.g. 2-(N-pyrrolidinyl)ethoxy, 2-(N-morpholinyl)ethoxy, 2-(N-imidazolyl)ethoxy), $C_1$-$C_4$-alkylsulfonylamino (e.g. 2-(methylsulfonylamino)ethoxy, 2-(ethylsulfonylamino)ethoxy, 2-[(2-methylpropyl)sulfonylamino]ethoxy), (halogenated $C_1$-$C_4$-alkyl)sulfonylamino (e.g. 2-(trifluoromethylsulfonylamino)ethoxy), $C_6$-$C_{12}$-arylsulfonylamino (e.g. 2-(phenylsulfonylamino)ethoxy, 2-(naphthylsulfonylamino)ethoxy), ($C_6$-$C_{12}$-aryl-$C_1$-$C_2$-alkyl)sulfonylamino (e.g. 2-(benzylsulfonylamino)ethoxy), $C_3$-$C_{12}$-heterocyclylsulfonylamino (e.g. 2-(pyridin-3-yl-sulfonylamino)ethoxy), or $C_6$-$C_{12}$-aryl (e.g. benzyloxy); and even more preferably substituted ethoxy, such as $C_1$-$C_6$-alkoxy-ethoxy (e.g. 2-methoxyethoxy), amino-ethoxy (e.g. 2-aminoethoxy), di-$C_1$-$C_6$-alkylamino-ethoxy (e.g. 2-(dimethylamino)ethoxy), $C_1$-$C_6$-alkylcarbonylamino-ethoxy (e.g. 2-(methylcarbonylamino)ethoxy, 2-(isopropylcarbonylamino)ethoxy), $C_6$-$C_{12}$-arylcarbonylamino-ethoxy (e.g. 2-(benzoylamino)ethoxy), $C_1$-$C_6$-alkoxycarbonylamino-ethoxy (e.g. 2-(t-butyloxycarbonylamino)ethoxy), $C_3$-$C_{12}$-heterocyclyl-ethoxy (e.g. 2-(N-pyrrolidinyl)ethoxy, 2-(N-morpholinyl)ethoxy, 2-(N-imidazolyl)ethoxy), $C_1$-$C_6$-alkylsulfonylamino-ethoxy (e.g. 2-(methylsulfonylamino)ethoxy, 2-(ethylsulfonylamino)ethoxy, 2-[(2-methylpropyl)sulfonylamino]ethoxy), (halogenated $C_1$-$C_4$-alkyl)sulfonylamino-ethoxy (e.g. 2-(trifluoromethylsulfonylamino)ethoxy), $C_6$-$C_{12}$-arylsulfonylamino-ethoxy (e.g. 2-(phenylsulfonylamino)ethoxy, 2-(naphthylsulfonylamino)ethoxy), ($C_6$-$C_{12}$-aryl-$C_1$-$C_4$-alkyl)sulfonylamino-ethoxy (e.g. 2-(benzylsulfonylamino)ethoxy), $C_3$-$C_{12}$-heterocyclylsulfonylamino-ethoxy (e.g. 2-(pyridin-3-yl-sulfonylamino)ethoxy).

According to a further particular embodiment, $R^5$ is a radical that is bound to the quinoline nucleus via a sulphur atom, such as $C_1$-$C_6$-alkylthio (e.g. methylthio), $C_1$-$C_6$-alkylsulfinyl (e.g. methylsulfinyl), $C_1$-$C_6$-alkylsulfonyl (e.g. methylsulfonyl), aminosulfonyl (e.g. aminosulfonyl), $C_1$-$C_6$-alkylaminosulfonyl (e.g. isopropylaminosulfonyl), di-$C_1$-$C_6$-alkylaminosulfonyl (e.g. dimethylaminosulfonyl) or (optionally substituted $C_6$-$C_{12}$-aryl)aminosulfonyl (e.g. (4-chlorophenyl)aminosulfonyl).

According to a further particular embodiment, $R^5$ is amino (e.g. amino).

According to a further particular embodiment, $R^5$ is a substituted amino group, such as $C_1$-$C_6$-alkylamino (e.g. methylamino, ethylamino), di-$C_1$-$C_6$-alkylamino (e.g. dimethylamino), $C_1$-$C_6$-alkylcarbonylamino (e.g. methylcarbonylamino, isopropylcarbonylamino), $C_6$-$C_{12}$-arylcarbonylamino (e.g. phenylcarbonylamino), $C_1$-$C_6$-alkylsulfonylamino (e.g. methylsulfonylamino), $C_6$-$C_{12}$-arylsulfonylamino (e.g. phenylsulfonylamino), di-($C_1$-$C_6$-alkylsulfonyl)amino (e.g. di(methylsulfonyl)amino), optionally substituted $C_3$-$C_{12}$-heterocyclyl (e.g. N-pyrrolidinyl, N-piperazinyl, 4-[(4-methylphenyl)sulfonyl]piperazinyl, morpholin-1-yl). Preferred heterocyclyl substituents are halogen, in particular fluoro and chloro, $C_1$-$C_4$-alkyl, $C_1$-$C_4$-haloalkyl, $C_1$-$C_4$-alkoxy, in particular ethoxy, and $C_1$-$C_4$-haloalkoxy, in particular chloromethoxy.

$R^{6a}$, $R^{6b}$, $R^{6c}$, $R^{6d}$, $R^{6e}$ are independently hydrogen, halogen, $C_1$-$C_6$-alkyl, halogenated $C_1$-$C_4$-alkyl, $C_1$-$C_4$-hydroxyalkyl, $C_1$-$C_6$-alkoxycarbonyl, (halogenated $C_1$-$C_4$-alkoxy)carbonyl, cyano, $C_1$-$C_6$-alkoxy, halogenated $C_1$-$C_4$-alkoxy, optionally substituted $C_6$-$C_{12}$-aryl, $C_1$-$C_4$-alkylthio, (halogenated $C_1$-$C_4$-alkyl)thio, nitro, amino, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl)carbonylamino, $C_1$-$C_6$-alkylsulfonylamino, (halogenated $C_1$-$C_4$-alkyl)sulfonylamino or $C_6$-$C_{12}$-arylsulfonylamino.

$R^6$ is preferably hydrogen, halogen (e.g. fluoro, bromo, chloro), $C_1$-$C_6$-alkyl (e.g. methyl), halogenated $C_1$-$C_4$-alkyl (e.g. trifluoromethyl), $C_1$-$C_4$-hydroxyalkyl, cyano, $C_1$-$C_6$-alkoxy (e.g. methoxy), optionally substituted $C_6$-$C_{12}$-aryl (e.g. 3,5-dichlorophenyl), amino, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl)carbonylamino, $C_1$-$C_6$-alkylsulfonylamino, (halogenated $C_1$-$C_4$-alkyl)sulfonylamino or $C_6$-$C_{12}$-arylsulfonylamino, more preferably hydrogen, halogen (e.g. fluoro, bromo, chloro), $C_1$-$C_6$-alkyl (e.g. methyl), halogenated $C_1$-$C_4$-alkyl (e.g. trifluoromethyl), $C_1$-$C_6$-alkoxy (e.g. methoxy) or optionally substituted $C_6$-$C_{12}$-aryl (e.g. 3,5-dichlorophenyl). Preferred aryl substituents are halogen, in particular fluoro and chloro, $C_1$-$C_4$-alkyl, $C_1$-$C_4$-haloalkyl, $C_1$-$C_4$-alkoxy, in particular ethoxy, and $C_1$-$C_4$-haloalkoxy, in particular chloromethoxy.

$R^{6b}$ is preferably hydrogen, halogen (e.g. fluoro, chloro), $C_1$-$C_6$-alkyl (e.g. methyl), halogenated $C_1$-$C_4$-alkyl (e.g. trifluoromethyl), $C_1$-$C_4$-hydroxyalkyl, cyano, $C_1$-$C_6$-alkoxy (e.g. methoxy), nitro (e.g. nitro), amino, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl)carbonylamino, $C_1$-$C_6$-alkylsulfonylamino, (halogenated $C_1$-$C_4$-alkyl)sulfonylamino or $C_6$-$C_{12}$-arylsulfonylamino, more preferably hydrogen, halogen (e.g. fluoro, chloro), $C_1$-$C_6$- alkyl (e.g. methyl), halogenated $C_1$-$C_4$-alkyl (e.g. trifluoromethyl), $C_1$-$C_6$-alkoxy (e.g. methoxy) or nitro (e.g. nitro).

$R^{6c}$ is preferably hydrogen, halogen (e.g. fluoro, bromo, chloro), $C_1$-$C_6$-alkyl (e.g. methyl, t-butyl), halogenated $C_1$-$C_4$-alkyl (e.g. trifluoromethyl), $C_1$-$C_4$-hydroxyalkyl, $C_1$-$C_6$-alkoxycarbonyl (e.g. methoxycarbonyl), cyano, $C_1$-$C_6$-alkoxy (e.g. methoxy), halogenated $C_1$-$C_4$-alkoxy (e.g. trifluoromethoxy), halogenated $C_1$-$C_4$-alkylthio (e.g. trifluoromethylthio), nitro (e.g. nitro), amino, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl)carbonylamino, $C_1$-$C_6$-alkylsulfonylamino, (halogenated $C_1$-$C_4$-alkyl)sulfonylamino or $C_6$-$C_{12}$-arylsulfonylamino, more preferably hydrogen, halogen (e.g. fluoro, bromo, chloro), $C_1$-$C_6$-alkyl (e.g. methyl, t-butyl), halogenated $C_1$-$C_4$-alkyl (e.g. trifluoromethyl), $C_1$-$C_6$-alkoxycarbonyl (e.g. methoxycarbonyl), $C_1$-$C_6$-alkoxy (e.g. methoxy), halogenated $C_1$-$C_4$-alkoxy (e.g. trifluoromethoxy), halogenated $C_1$-$C_4$-alkylthio (e.g. trifluoromethylthio) or nitro (e.g. nitro).

$R^{6d}$ is preferably hydrogen, halogen (e.g. chloro), $C_1$-$C_6$-alkyl (e.g. methyl), halogenated $C_1$-$C_4$-alkyl, $C_1$-$C_4$-hydroxyalkyl, cyano, $C_1$-$C_6$-alkoxy (e.g. methoxy), nitro, amino, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl)carbonylamino, $C_1$-$C_6$-alkylsulfonylamino, (halogenated $C_1$-$C_4$-alkyl)sulfonylamino or $C_6$-$C_{12}$-arylsulfonylamino, more preferably hydrogen, halogen (e.g. chloro), $C_1$-$C_6$-alkyl (e.g. methyl) or $C_1$-$C_6$-alkoxy (e.g. methoxy).

$R^{6e}$ is preferably hydrogen, halogen, $C_1$-$C_6$-alkyl, halogenated $C_1$-$C_4$-alkyl, $C_1$-$C_4$-hydroxyalkyl, cyano, $C_1$-$C_6$-alkoxy, optionally substituted $C_6$-$C_{12}$-aryl, amino, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl) carbonylamino, $C_1$-$C_6$-alkylsulfonylamino, (halogenated $C_1$-$C_4$-alkyl)sulfonylamino or $C_6$-$C_{12}$-arylsulfonylamino, more preferably hydrogen.

Alternatively, $R^{6a}$ and $R^2$ together are optionally substituted $C_1$-$C_4$-alkylene, preferably un-substituted $C_1$-$C_4$-alkylene (e.g. ethylene), thereby forming a group of the formula (III):

(III)

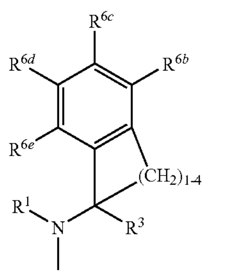

wherein $R^1$, $R^3$, $R^{6b}$, $R^{6c}$, $R^{6d}$, $R^{6e}$ are as defined above (the group of formula (III) is bound to the quinoline nucleus).

Alternatively, $R^{6a}$ and $R^{6b}$ or $R^{6b}$ and $R^{6c}$, preferably $R^{6a}$ and $R^{6b}$, together with the carbon atoms to which they are attached form an anellated aryl ring, preferably an anellated $C_5$-$C_{10}$-aryl ring (e.g. benzene), $R^{6a}$ or $R^{6c}$, and $R^{6d}$ and $R^{6e}$ being as defined herein.

Alternatively, $R^{6a}$ and $R^{6b}$ or $R^{6b}$ and $R^{6c}$, preferably $R^{6b}$ and $R^{6c}$, together are $C_1$-$C_2$-alkylenedioxo (e.g. methylenedioxo), thereby forming a group of the formula (IVa) or (IVb):

(IVa)

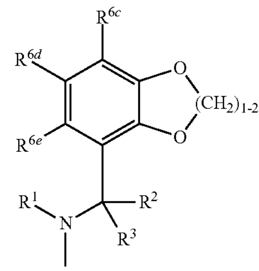

(IVb)

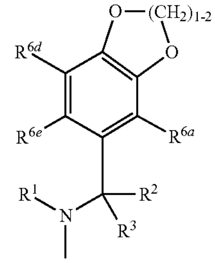

wherein $R^1$, $R^2$, $R^3$, $R^{6a}$ or $R^{6c}$, $R^{6d}$ and $R^{6e}$ are as defined above (the group of formula (IIIa) or (IIIb) is bound to the quinoline nucleus).

According to a particular embodiment, at least one of $R^{6a}$, $R^{6b}$, $R^{6c}$, $R^{6d}$, $R^{6e}$ is different from hydrogen. Preferably, at least one of $R^{6a}$, $R^{6b}$, $R^{6c}$, $R^{6d}$, $R^{6e}$ is halogen (e.g. fluoro, bromo, chloro), $C_1$-$C_4$-hydroxyalkyl, cyano or nitro (e.g. nitro). More preferably, at least one of $R^{6a}$, $R^{6b}$, $R^{6c}$, $R^{6d}$, $R^{6e}$ is halogen (e.g. fluoro, bromo, chloro) or nitro (e.g. nitro).

According to a further particular embodiment, at least one of $R^{6a}$, $R^{6c}$ is different from hydrogen. Preferably, at least one of $R^{6a}$, $R^{6c}$ is halogen (e.g. fluoro, bromo, chloro), $C_1$-$C_4$-hydroxyalkyl, cyano or nitro (e.g. nitro). More preferably, at least one of $R^{6a}$, $R^{6c}$ is halogen (e.g. fluoro, bromo, chloro) or nitro (e.g. nitro).

According to a further particular embodiment, at least one of $R^{6b}$, $R^{6c}$, $R^{6d}$ is different from hydrogen. Preferably, at least one of $R^{6b}$, $R^{6b}$, $R^{6d}$ is halogen (e.g. fluoro, bromo, chloro), $C_1$-$C_4$-hydroxyalkyl; cyano or nitro (e.g. nitro). More preferably, at least one of $R^{6b}$, $R^{6c}$, $R^{6d}$ is halogen (e.g. fluoro, bromo, chloro) or nitro (e.g. nitro).

According to a further particular embodiment, at least one of $R^{6b}$, $R^{6c}$ is different from hydrogen. Preferably, at least one of $R^{6b}$, $R^{6c}$ is halogen (e.g. fluoro, bromo, chloro), $C_1$-$C_4$-hydroxyalkyl, cyano or nitro (e.g. nitro). More preferably, at least one of $R^{6b}$, $R^{6c}$ is halogen (e.g. fluoro, bromo, chloro) or nitro (e.g. nitro).

According to a further particular embodiment, $R^{6c}$ is different from hydrogen. Preferably, $R^{6c}$ is halogen (e.g. fluoro, bromo, chloro), $C_1$-$C_4$-hydroxyalkyl; cyano or nitro (e.g. nitro). More preferably, $R^{6c}$ is halogen (e.g. fluoro, bromo, chloro) or nitro (e.g. nitro).

According to a further particular embodiment, $R^{6a}$, $R^{6e}$ are both hydrogen.

$R^7$, $R^8$, $R^9$, $R^{10}$ are independently hydrogen, halogen, $C_1$-$C_6$-alkyl or $C_1$-$C_6$-alkoxy. Preferably, $R^7$, $R^8$, $R^9$, $R^{10}$ are all hydrogen.

4-Benzylaminoquinoline of the formula (I)

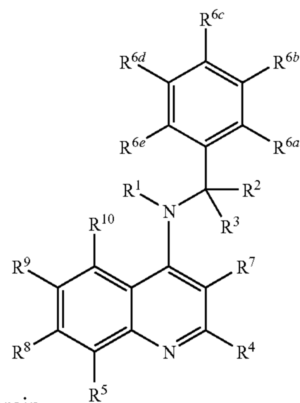

wherein $R^1$ is hydrogen;

$R^2$ is hydrogen, $C_1$-$C_4$-alkyl (e.g. methyl), amino-$C_1$-$C_4$-alkyl (e.g. aminomethyl), $C_1$-$C_6$-alkylamino-$C_1$-$C_4$-alkyl (e.g. isopropylaminomethyl), di-$C_1$-$C_6$-alkylamino-$C_1$-$C_4$-alkyl (e.g. dimethylaminomethyl), ($C_6$-$C_{12}$-aryl-$C_1$-$C_4$-alkyl)amino-$C_1$-$C_4$-alkyl (e.g. benzylaminomethyl), $C_3$-$C_{12}$-heterocyclyl-$C_1$-$C_4$-alkyl (e.g. N-pyrrolidinylmethyl, N-piperidinylmethyl, N-morpholinylmethyl), $C_3$-$C_{12}$-cycloalkyl (e.g. cyclopropyl), $C_6$-$C_{12}$-aryl (e.g. phenyl), aminocarbonyl (e.g. aminocarbonyl), $C_3$-$C_{12}$-heterocyclyl (e.g. piperidin-2-yl, N-methylpiperidin-2-yl, N-allylpiperidin-2-yl, pyridin-4-yl or N-methylimidazol-2-yl);

$R^3$ is hydrogen;

$R^4$ is methyl or dimethylamino;

$R^5$ is hydrogen, halogen (e.g. fluoro, chloro), $C_1$-$C_6$-alkyl (e.g. methyl), hydroxy (e.g. hydroxy), $C_1$-$C_6$-alkoxy (e.g. methoxy, n-propyloxy, isopropyloxy, 2-methylpropyloxy), halogenated $C_1$-$C_4$-alkoxy (e.g. trifluoromethoxy), $C_1$-$C_6$-alkoxy-$C_1$-$C_4$-alkoxy (e.g. 2-methoxyethoxy), amino-$C_1$-$C_4$-alkoxy (e.g. 2-aminoethoxy), di-$C_1$-$C_6$-alkylamino-$C_1$-$C_4$-alkoxy (e.g. 2-(dimethylamino)ethoxy), $C_1$-$C_6$-alkylcarbonylamino-$C_1$-$C_4$-alkoxy (e.g. 2-(methylcarbonylamino)ethoxy, 2-(isopropylcarbonylamino)ethoxy), ($C_6$-$C_{12}$-arylcarbonylamino-$C_1$-$C_4$-alkoxy (e.g. 2-(benzoylamino)ethoxy), $C_1$-$C_6$-alkoxycarbonylamino-$C_1$-$C_4$-alkoxy (e.g. 2-(t-butyloxycarbonylamino)ethoxy), $C_3$-$C_{12}$-heterocyclyl-$C_1$-$C_6$-alkoxy (e.g. 2-(N-pyrrolidinyl)ethoxy, 2-(N-morpholinyl)ethoxy, 2-(N-imidazolyl)ethoxy), $C_1$-$C_6$-alkylsulfonylamino-$C_1$-$C_4$-alkoxy (e.g. 2-(methylsulfonylamino)ethoxy, 2-(ethylsulfonylamino)ethoxy, 2-[(2-methylpropyl)sulfonylamino]ethoxy), (halogenated $C_1$-$C_4$-alkyl)sulfonylamino-$C_1$-$C_4$-alkoxy (e.g. 2-(trifluoromethylsulfonylamino)ethoxy), $C_6$-$C_{12}$-arylsulfonylamino-$C_1$-$C_4$-alkoxy (e.g. 2-(phenylsulfonylamino) ethoxy, 2-(naphthylsulfonylamino)ethoxy), ($C_6$-$C_{12}$-aryl-$C_1$-$C_4$-alkyl)sulfonylamino-$C_1$-$C_4$-alkoxy (e.g. 2-(benzylsulfonylamino)ethoxy), $C_3$-$C_{12}$-heterocyclylsulfonylamino-$C_1$-$C_4$-alkoxy (e.g. 2-(pyridin-3-yl-sulfonylamino)ethoxy), $C_6$-$C_{12}$-aryl-$C_1$-$C_4$-alkoxy (e.g. benzyloxy), $C_6$-$C_{12}$-aryloxy (e.g. phenoxy), $C_6$-$C_{12}$-heteroaryloxy (e.g. pyridin-2-yloxy), $C_1$-$C_6$-alkylthio (e.g. methylthio), $C_1$-$C_6$-alkylsulfinyl (e.g. methylsulfinyl), $C_1$-$C_6$-alkylsulfonyl (e.g. methylsulfonyl), aminosulfonyl (e.g. aminosulfonyl), $C_1$-$C_6$-alkylaminosulfonyl (e.g. isopropylaminosulfonyl), di-$C_1$-$C_6$-alkylaminosulfonyl (e.g. dimethylaminosulfonyl), (optionally substituted $C_6$-$C_{12}$-aryl)aminosulfonyl (e.g. (4-chlorophenyl)aminosulfonyl), amino (e.g. amino), $C_1$-$C_6$-alkylamino (e.g. methylamino, ethylamino), di-$C_1$-$C_6$-alkylamino (e.g. dimethylamino), $C_1$-$C_6$-alkylcarbonylamino (e.g. methylcarbonylamino, isopropylcarbonylamino), $C_6$-$C_{12}$-arylcarbonylamino (e.g. phenylcarbonylamino), $C_1$-$C_6$-alkylsulfonylamino (e.g. methylsulfonylamino), $C_6$-$C_{12}$-arylsulfonylamino (e.g. phenylsulfonylamino), di-($C_1$-$C_6$-alkylsulfonyl) amino (e.g. di(methylsulfonyl)amino), optionally substituted $C_3$-$C_{12}$-heterocyclyl (e.g. N-pyrrolidinyl, N-piperazinyl or 4[(4-methylphenyl)sulfonyl]piperazinyl, morpholin-1-yl);

$R^{6a}$, $R^{6e}$ are hydrogen;

$R^{6b}$, $R^{6c}$, $R^{6d}$ are independently hydrogen, halogen (e.g. fluoro, bromo, chloro), $C_1$-$C_6$-alkyl (e.g. methyl, t-butyl), halogenated $C_1$-$C_4$-alkyl (e.g. trifluoromethyl), $C_1$-$C_6$-alkoxycarbonyl (e.g. methoxycarbonyl), $C_1$-$C_6$-alkoxy (e.g. methoxy), halogenated $C_1$-$C_4$-alkoxy (e.g. trifluoromethoxy), halogenated $C_1$-$C_4$-alkylthio (e.g. trifluoromethylthio) or nitro (e.g. nitro), at least one of $R^{6b}$, $R^{6c}$, $R^{6d}$ being different from hydrogen, and $R^7$, $R^8$, $R^9$, $R^{10}$ are all hydrogen, or a physiologically tolerated acid addition salt (e.g. trifluoroacetate, bromide, chloride) thereof, are particularly preferred compounds of the present invention.

Particular compounds of the present invention are the 4-benzylaminoquinolines disclosed in examples 1 to 96 and physiologically tolerated acid addition salts thereof.

The compounds of the formula (I) can be prepared by analogy to methods which are well known in the art. A suitable method for the preparation of compounds of formula (I) is outlined in the following schemes.

The process depicted in scheme 1 is useful for obtaining 4-benzylaminochinolines having N-alkyl, N-aryl, amide or sulfonamide radicals in 8-position.

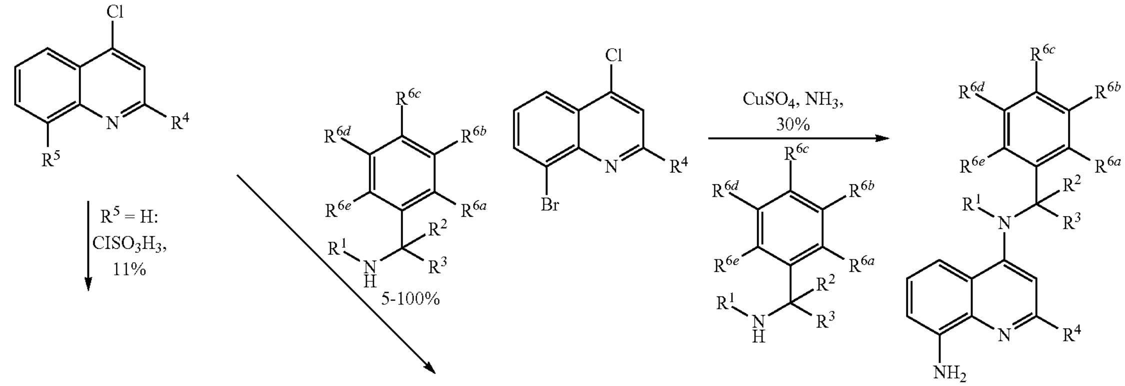

-continued

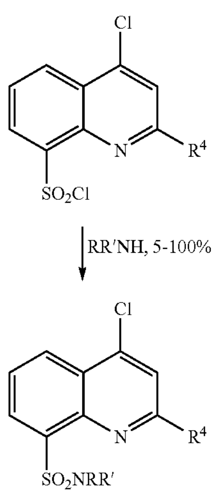

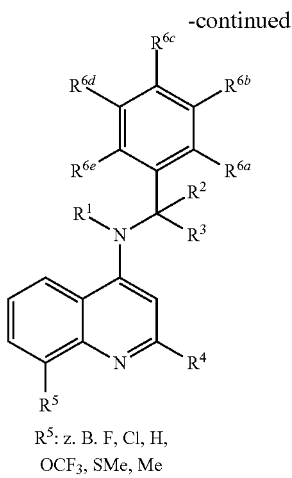

Alkylation: R-Hal, NEt$_3$, DMF, 14-27%
Acylation: RCOCl, Pyridine, 53-62%
Sulfonylation: RSO$_2$Cl, Pyridine, 14-24%

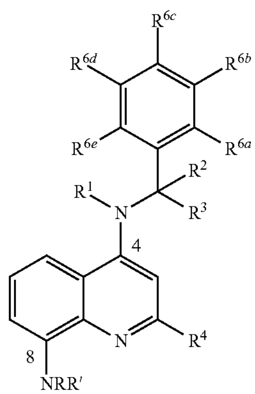

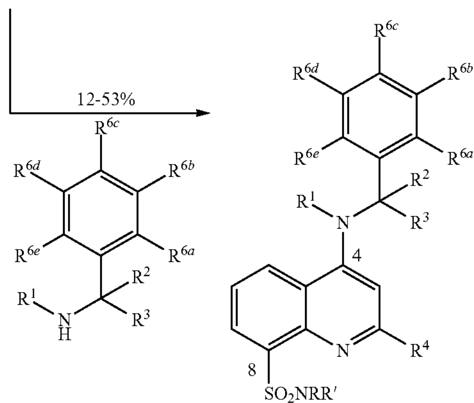

In scheme 1, the variables $R^1$, $R^2$, $R^3$, $R^4$, $R^5$, $R^{6a}$, $R^{6b}$, $R^{6c}$, $R^{6d}$, $R^{6e}$ are as defined herein (unless indicated otherwise). Hal is chlorine or bromine. R, R' are independently hydrogene, $C_1$-$C_6$-alkyl or optionally substituted $C_6$-$C_{12}$-aryl as defined herein.

The process depicted in scheme 2 is useful for obtaining 4-benzylaminochinolines having ether radicals in 8-position.

Scheme 2:

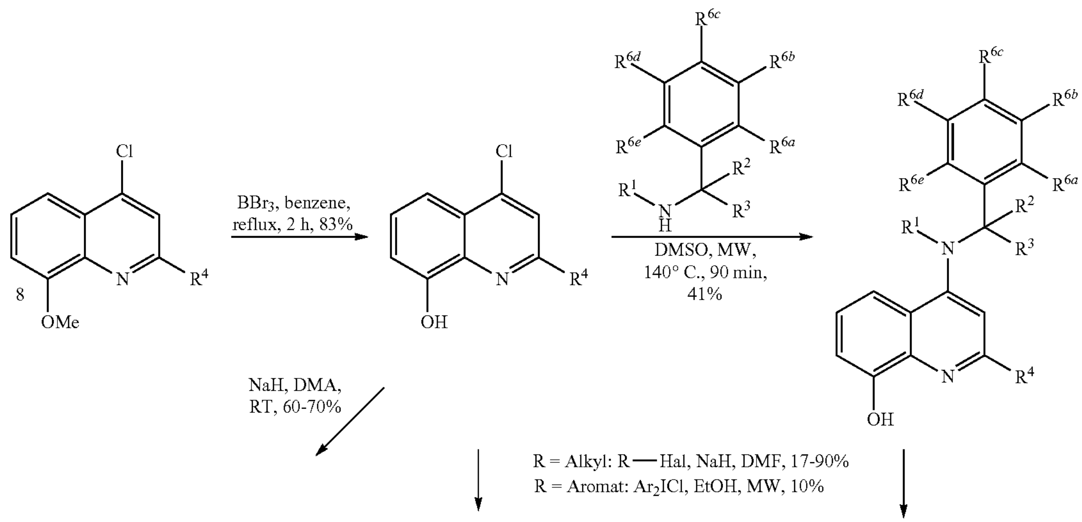

-continued

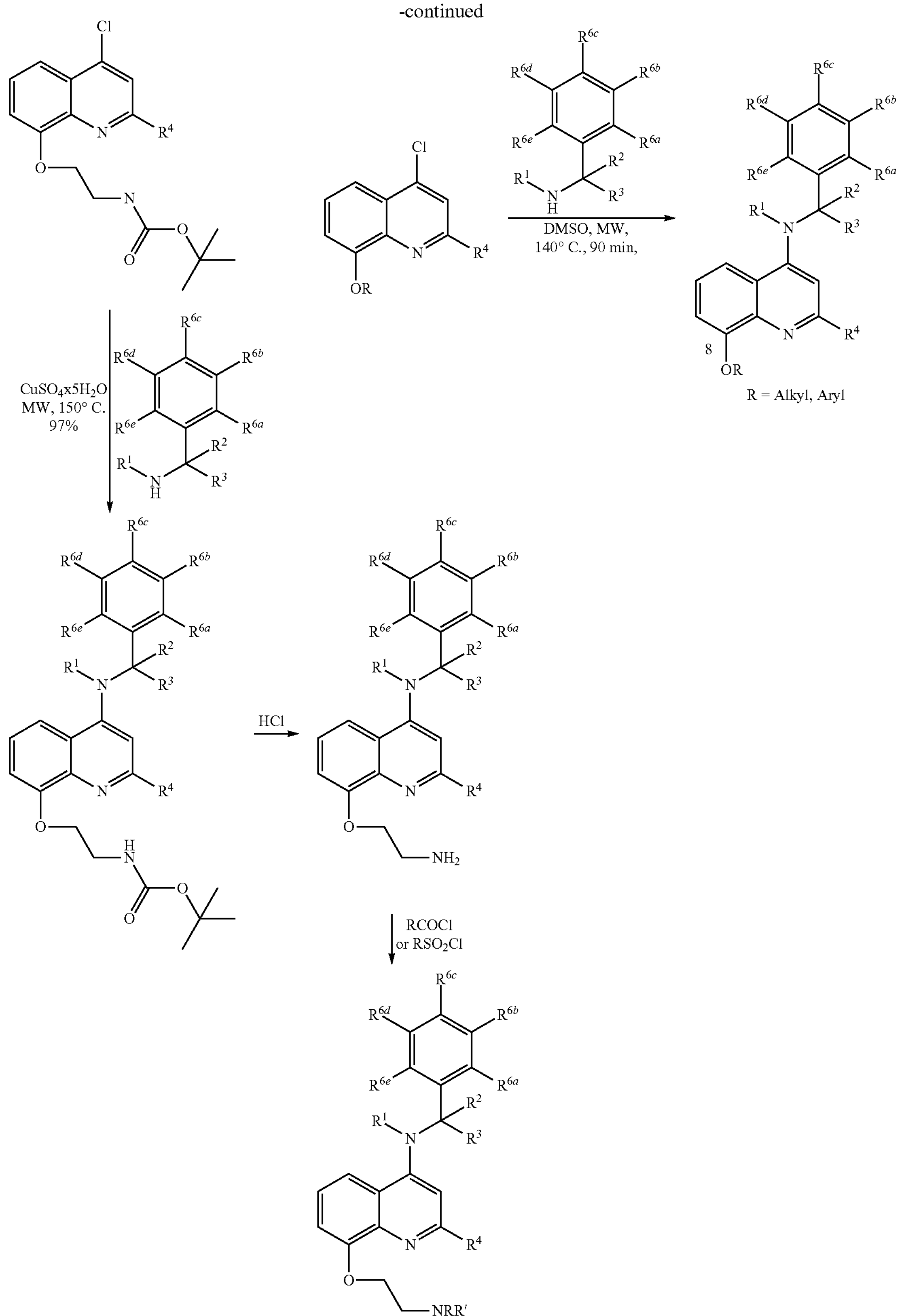

In scheme 2, the variables $R^1$, $R^2$, $R^3$, $R^4$, $R^5$, $R^{6a}$, $R^{6b}$, $R^{6c}$, $R^{6d}$, $R^{6e}$ are as defined herein (unless indicated otherwise). Hal is chlorine or bromine. R, R' are independently hydrogen, $C_1$-$C_6$-alkyl, $C_1$-$C_6$-alkylcarbonyl, $C_1$-$C_6$-alkenylcarbonyl, $C_1$-$C_6$-alkylsulfonyl, (halogenated $C_1$-$C_6$-alkyl)sulfonyl, $C_6$-$C_{12}$-arylsulfonyl, ($C_6$-$C_{12}$-aryl $C_1$-$C_4$-alkyl)sulfonyl or $C_3$-$C_{12}$-heterocyclylsulfonyl.

4-Benzylaminochinolines having a dimethylamine radical in 2-position are obtainable by the process depicted in scheme 3.

Scheme 3:

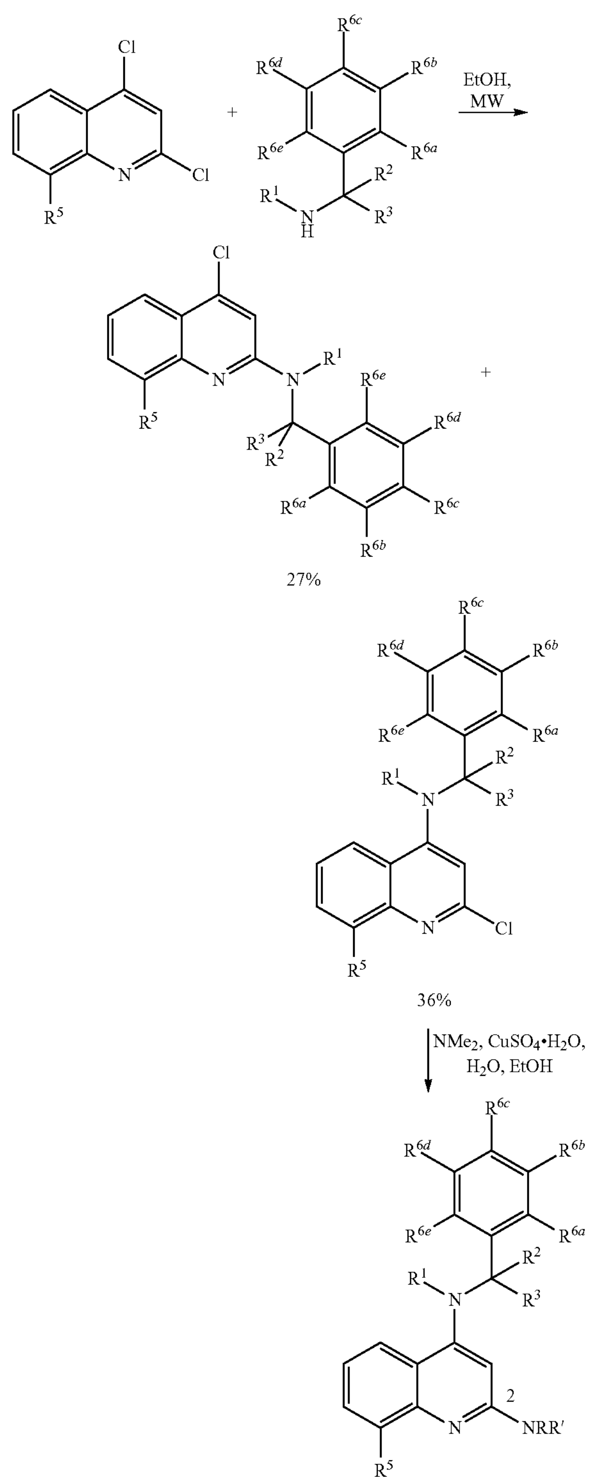

In scheme 3, the variables $R^1$, $R^2$, $R^3$, $R^4$, $R^5$, $R^{6a}$, $R^{6b}$, $R^{6c}$, $R^{6d}$, $R^{6e}$ are as defined herein (unless indicated otherwise). R, R' are independently $C_1$-$C_6$-alkyl.

The acid addition salts of the 4-benzylaminoquinolines of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition (ICA by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}<1$ μMol, more preferably at a level of $IC_{50}<0.5$ μMol, particularly preferably at a level of $IC_{50}<0.2$ μMol and most preferably at a level of $IC_{50}<0.1$ μMol.

The compounds of the formula (I) according to the present invention are thus useful as pharmaceuticals.

The present invention therefore also relates to pharmaceutical compositions which comprise a carrier and a compound of the formula (I). Said carrier is preferably inert.

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

The compounds of formula (I) are particularly useful in the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; anti-irritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refitting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4th edition, Aulendorf: ECV-Editio-Cantor-Verlag, 1996.

The following examples serve to explain the invention without limiting it.

The compounds were characterized by mass spectrometry, generally recorded via HPLC-MS in a fast gradient on C18-material (electrospray-ionisation (ESI) mode).

PREPARATION EXAMPLES

Example 1

4-(3,4-Dichlorobenzylamino)-2-methylquinoline-8-sulfonic dimethylamide

1.1 4-Chloro-2-methylquinoline-8-sulfonyl chloride

4-Chloro-2-methylquinoline (10.0 g, 0.056 mole) was added dropwise to chlorosulfonic

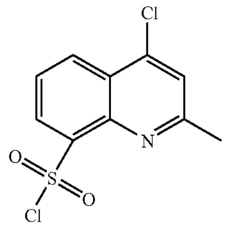 [SMILES: Cc1cc(Cl)c2cccc(S(=O)(=O)Cl)c2n1]

acid (61.3 g, 0.526 mole) under stirring at room temperature to undergo an exothermic reaction. The mixture was stirred at 110° C. for 18 hrs. The content of the flask was poured into ice cold water and extracted with dichloromethane. The combined organic phases were concentrated and purified using silica gel chromatography, eluting with cyclohexane:ethyl acetate 80:20. The residue was extracted with cyclohexane to give 1.7 g (11%) of a yellowish solid.

ESI-MS [M+H]+=276.0/278.0 calculated for $C_{10}H_7Cl_2NO_2S$=276 g/mole

1.2 4-Chloro-2-methylquinoline-8-sulfonic dimethylamide

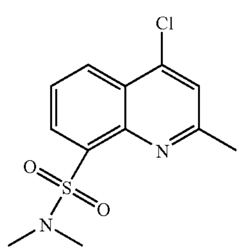

4-Chloro-2-methylquinoline-8-sulfonyl chloride (100 mg, 0.362 mmole) and a 40% solution of dimethylamine in water (408 mg, 3.62 mmole) were stirred at 60° C. for 1 h. The content of the flask was filtered off and a white solid was obtained (103 mg, 100%).

ESI-MS [M+H]+=285.1 calculated for $C_{12}H_{13}ClN_2O_2S$=285 g/mole

1.3 4-(3,4-Dichlorobenzylamino)-2-methylquinoline-8-sulfonic dimethylamide

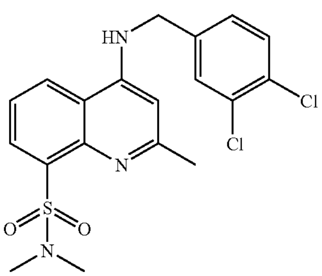 [SMILES: Cc1cc(NCc2ccc(Cl)c(Cl)c2)c2cccc(S(=O)(=O)N(C)C)c2n1]

4-Chloro-2-methylquinoline-8-sulfonic dimethylamide (80 mg, 0.281 mmole) and 3,4-dichlorobenzylamine (100 mg, 0.568 mmole) were stirred at 155° C. for 10 min in a microwave oven. Methanol was added and the mixture was concentrated, mixed with dichloromethane and then filtered. The residue was purified using silica gel chromatography, eluting with dichloromethane:methanol 95:5. Precipitation in ethyl acetate gave a pink solid (15 mg, 13%).

ESI-MS [M+H]+=424.1/428.1 calculated for $C_{19}H_{19}Cl_2N_3O_2S$=424 g/mole

Example 2

4-(3,4-Dichlorobenzylamino)-2-methylquinoline-8-sulfonamide

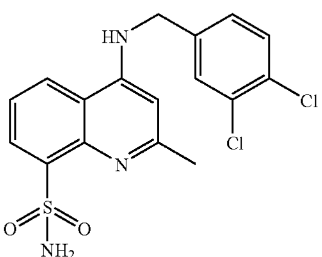

Preparation was made using a similar procedure as described in example 1, method 1.3. Starting materials were 4-chloro-2-methylquinoline-8-sulfonamide and dichlorobenzylamine.

Yield: 29%.

ESI-MS [M+H]+=396.1/398.1 calculated for $C_{17}H_{15}Cl_2N_3O_2S$=396 g/mole

Example 3

4-(3,4-Dichlorobenzylamino)-2-methyl-quinoline-8-sulfonic isopropylamide

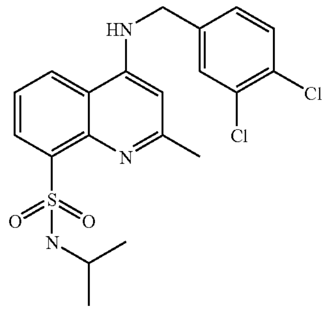 [SMILES: Cc1cc(NCc2ccc(Cl)c(Cl)c2)c2cccc(S(=O)(=O)NC(C)C)c2n1]

Preparation was made using a similar procedure as described in example 1, method 1.3. Starting materials were 4-chloro-2-methylquinoline-8-sulfonic isopropylamide and dichlorobenzylamine.

Yield: 53° A.

ESI-MS [M+H]+=438.4/440.4 calculated for $C_{20}H_{21}Cl_2N_3O_2S$=438 g/mole

Example 4

4-(3,4-Dichlorobenzylamino)-2-methylquinoline-8-sulfonic (4-chlorophenyl)-amide

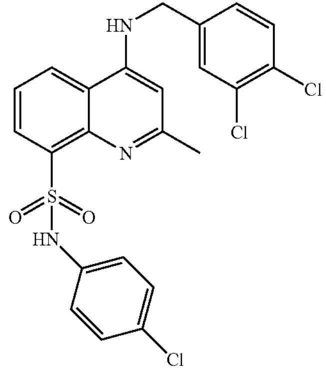 [SMILES: Cc1cc(NCc2ccc(Cl)c(Cl)c2)c2cccc(S(=O)(=O)Nc3ccc(Cl)cc3)c2n1]

Preparation was made using a similar procedure as described in example 1, method 1.3. Starting materials were 4-chloro-2-methylquinoline-8-sulfonic (4-chlorophenyl)-amide and dichlorobenzylamine.

Yield: 25%.

ESI-MS [M+H]+=506.1/510.0 calculated for $C_{23}H_{18}Cl_3N_3O_2S$=507 g/mole

Example 5

N*4*-(3,4-Dichlorobenzyl)-2-methylquinoline-4,8-diamine 5.1 (8-Bromo-2-methylquinolin-4-yl)-(3,4-dichlorobenzyl)-amine

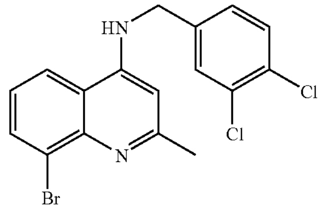 [SMILES: Cc1cc(NCc2ccc(Cl)c(Cl)c2)c2cccc(Br)c2n1]

8-Bromo-4-chloro-2-methylquinoline (4.50 g, 17.5 mmole) and 3,4-dichlorobenzylamine (6.30 g, 35.8 mmole) in dimethylsulfoxide (6 mL) were stirred at 140° C. for 2 h in a microwave oven. Water was added and the mixture was decanted to obtain an oily residue. The residue was washed with ethyl acetate to give a white solid (1.40 g, 20%).

ESI-MS [M+H]+=395.1/397.1 calculated for $C_{17}H_{13}BrCl_2N_2$=396 g/mole 5.2. N*4*-(3,4-Dichlorobenzyl)-2-methylquinoline-4,8-diamine (8-Bromo-2-methylquinolin-4-yl)-(3,4-dichlorobenzyl)-amine (500 mg, 1.26 mmole), copper(II)sulphate pentahydrate (316 mg, 1.27 mmole) and ammonia (20% in water/ethanol 1:1, 20 mL) were stirred in a microwave oven at 150° C. for 5 hrs. The reaction mixture was dissolved in water and extracted with dichloromethane. The resulting organic phases were dried and purified using silica gel chromatography, eluting with dichloromethane:water 99:1. Precipitation in isopropyl ether gave a brownish solid (220 mg, 52%).

ESI-MS [M+H]+=332.1/334.1 calculated for $C_{17}H_{15}Cl_2N_3$=332 g/mole

Example 6

(3,4-Dichlorobenzyl)-(2-methyl-8-morpholin-4-yl-quinolin-4-yl)-amine hydrobromide

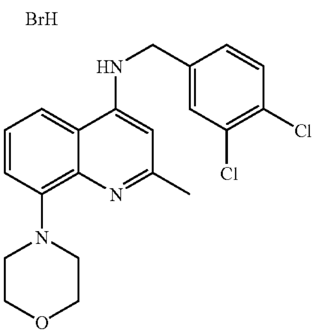 [SMILES: Br ; Cc1cc(NCc2ccc(Cl)c(Cl)c2)c2cccc(N3CCOCC3)c2n1]

N*4*-(3,4-Dichlorobenzyl)-2-methylquinoline-4,8-diamine (60.0 mg, 0.181 mmole) and bis(2-bromoethyl)ether (83.7 mg, 0.361 mmole) in dimethylformamide (1 mL), were stirred at 100° C. for 90 min in a microwave oven. Water was added and the mixture was extracted with dichloromethane. The organic phases were washed with saturated NaCl solution, dried and the solvent was removed. The residue thus obtained was purified using silica gel chromatography, eluting with dichloromethane:water 90:10. Precipitation in ethyl acetate gave a brownish solid (15 mg, 17%).

ESI-MS [M+H]+=402.1/406.0 calculated for $O_{21}H_{21}Cl_2N_3O$+402 g/mole

Example 7

(3,4-Dichlorobenzyl)-(2-methyl-8-pyrrolidin-1-yl-quinolin-4-yl)-amine hydrochloride

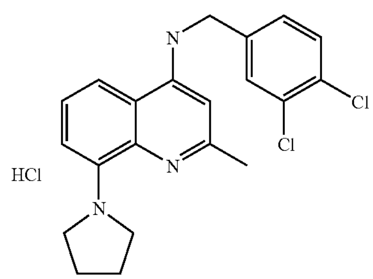 [SMILES: Cl ; Cc1cc(NCc2ccc(Cl)c(Cl)c2)c2cccc(N3CCCC3)c2n1]

Preparation was made using a similar procedure as described in example 6. Starting materials were 8-bromo-2-methylquinolin-4-yl)-(3,4-dichlorobenzyl)-amine and 1,4-dibromobutane.

Yield: 28%.

ESI-MS [M+H]+=386.1/390.1 calculated for $O_{21}H_{21}Cl_2N_3$=386 g/mole

Example 8

N-[4-(3,4-Dichlorobenzylamino)-2-methylquinolin-8-yl]-phenylsulfonamide

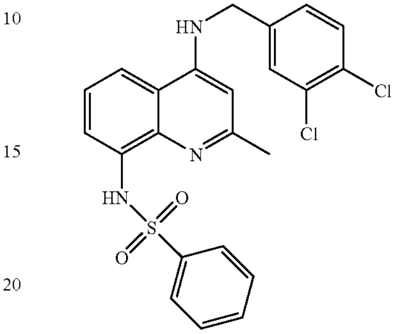

N*4*-(3,4-Dichlorobenzyl)-2-methylquinoline-4,8-diamine (60 mg, 0.181 mmole, example 5.1) and phenylsulfonylchloride (33.4 mg, 0.190 mmole) were dissolved in pyridine and stirred at RT for 76 hrs. The content of the flask was concentrated, 1N NaOH was added and the mixture was extracted using dichloromethane. The organic phase was washed with water and saturated NaCl solution and concentrated. The residue thus obtained was purified using silica gel chromatography, eluting with dichloromethane:water 95:5. Cristallisation from ethyl acetate:isopropyl ether 1:1 gave a yellow solid (21 mg, 25%). ESI-MS [M+H]+=472.3/474.3 calculated for $C_{23}H_{19}Cl_2N_3O_2S$=472 g/mole Example 9

N*4*-(3,4-Dichlorobenzyl)-N*8*-ethyl-2-methylquinolin-4,8-diamine

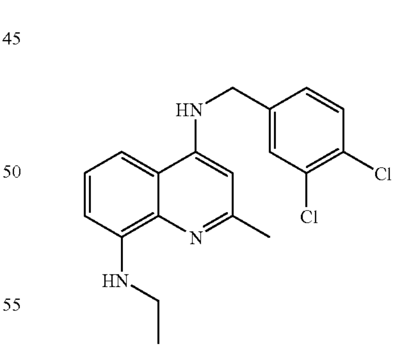

Preparation was made using a similar procedure as described in example 6. Starting materials were 8-bromo-2-methylquinolin-4-yl)-(3,4-dichlorobenzyl)-amine and bromoethane.

Yield: 17%.

ESI-MS [M+H]+=360.1/364.0 calculated for $C_{19}H_{19}Cl_2N_3$=360 g/mole

Example 10

N-[4-(3,4-Dichlorobenzylamino)-2-methylquinolin-8-yl]-benzamide

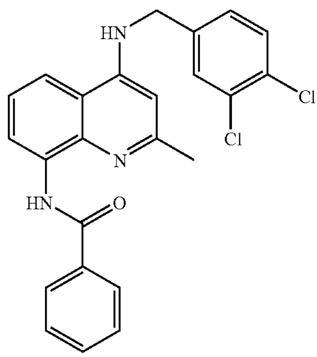 [SMILES: Cc1cc(NCc2ccc(Cl)c(Cl)c2)c2cccc(NC(=O)c3ccccc3)c2n1]

Preparation was made using a similar procedure as described in example 8. Starting materials were 8-bromo-2-methylquinolin-4-yl)-(3,4-dichlorobenzyl)-amine and benzoyl chloride.

Yield: 63%.

ESI-MS [M+H]+=436.1/440.1 calculated for $C_{24}H_{19}Cl_2N_3O$=436 g/mole

Example 11

N-[4-(3,4-Dichlorobenzylamino)-2-methylquinolin-8-yl]-bis-methanesulfonamide

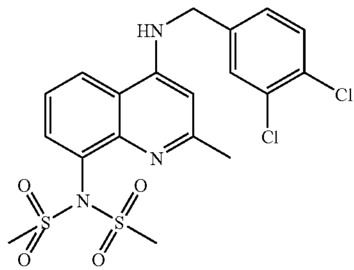 [SMILES: Cc1cc(NCc2ccc(Cl)c(Cl)c2)c2cccc(N(S(C)(=O)=O)S(C)(=O)=O)c2n1]

Preparation was made using a similar procedure as described in example 8. Starting materials were 8-bromo-2-methylquinolin-4-yl)-(3,4-dichlorobenzyl)-amine and methanesulfonyl chloride Yield: 15%.

ESI-MS [M+H]+=488.1/490.1 calculated for $C_{19}H_{19}Cl_2N_3O_4S_2$=488 g/mole

Example 12

N-[4-(3,4-Dichlorobenzylamino)-2-methylquinolin-8-yl]-methanesulfonamide

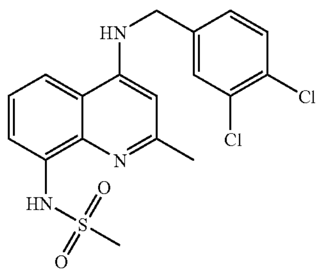 [SMILES: Cc1cc(NCc2ccc(Cl)c(Cl)c2)c2cccc(NS(C)(=O)=O)c2n1]

Preparation was made using a similar procedure as described in example 8. Starting materials were 8-bromo-2-methylquinolin-4-yl)-(3,4-dichlorobenzyl)-amine and methanesulfonyl chloride.

Yield: 17%.

ESI-MS [M+H]+=410.1/414.1 calculated for $C_{18}H_{17}Cl_2N_3O_2S$=410 g/mole

Example 13

N-[4-(3,4-Dichlorobenzylamino)-2-methylquinolin-8-yl]-acetamide

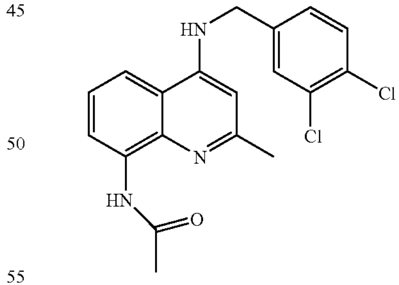

Preparation was made using a similar procedure as described in example 8. Starting materials were 8-bromo-2-methylquinolin-4-yl)-(3,4-dichlorobenzyl)-amine and acetylchloride.

Yield: 53° A.

ESI-MS [M+H]+=374.1/378.1 calculated for $C_{19}H_{17}Cl_2N_3O$=374 g/mole

Example 14

N-[4-(3,4-Dichlorobenzylamino)-2-methylquinolin-8-yl]-isobutyramide

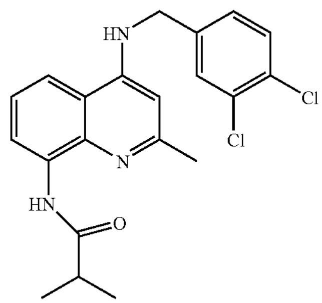 [SMILES: Cc1cc(NCc2ccc(Cl)c(Cl)c2)c2cccc(NC(=O)C(C)C)c2n1]

Preparation was made using a similar procedure as described in example 8. Starting materials were 8-bromo-2-methylquinolin-4-yl)-(3,4-dichlorobenzyl)-amine and isobutyrylchloride.

Yield: 58%.

ESI-MS [M+H]+=402.1/406.1 calculated for $O_{21}H_{21}Cl_2N_3O$=402 g/mole

Example 15

N*4*-(3,4-Dichlorobenzyl)-N*8*-methyl-2-methylquinolin-4,8-diamine

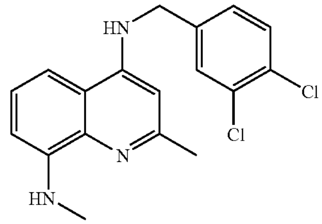 [SMILES: CNc1cccc2c(NCc3ccc(Cl)c(Cl)c3)cc(C)nc12]

Preparation was made using a similar procedure as described in example 6. Starting materials were 8-bromo-2-methylquinolin-4-yl)-(3,4-dichlorobenzyl)-amine and iodomethane.

Yield: 19%.

ESI-MS [M+H]+=346.2 calculated for $C_{18}H_{17}Cl_2N_3$=346 g/mole

Example 16

N*4*-(3,4-Dichlorobenzyl)-N*8*-dimethyl-2-methylquinolin-4,8-diamine hydrochloride

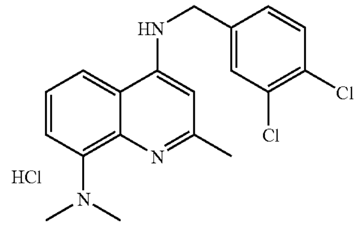 [SMILES: Cl ; Cc1cc(NCc2ccc(Cl)c(Cl)c2)c2cccc(N(C)C)c2n1]

(3,4-Dichlorobenzyl)-(8-fluoro-2-methyl-quinolin-4-yl)-amine (100 mg, 0.298 mmole), a solution of dimethylamine in water (40%, 4 mL), copper(I)chloride (59 mg, 0.596 mmole), and copper(II)sulphate pentahydrate (150 mg, 0.601 mmole) were suspended with absolute ethanol (0.5 mL) and stirred at 155° C. for 7 hrs in a microwave oven. Water was added and the mixture was extracted using dichloromethane. The organic phases were washed with saturated NaCl solution, dried and the solvent was removed. The residue thus obtained was purified using silica gel chromatography, eluting with dichloromethane:water 99:1 to give a yellow salt (12 mg, 10%).

ESI-MS [M+H]+=360.2/3.2 calculated for $C_{19}H_{19}Cl_2N_3$=360 g/mole

Example 17

(3,4-Dichlorobenzyl)-{2-methyl-8-[4-(toluene-4-sulfonyl)-piperazin-1-yl]-quinolin-4-yl}-amine

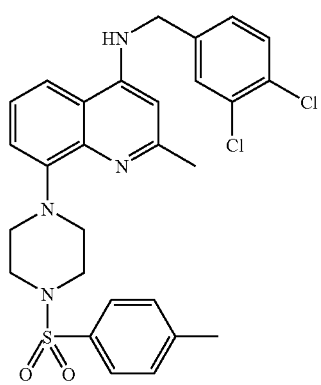 [SMILES: Cc1ccc(S(=O)(=O)N2CCN(c3cccc4c(NCc5ccc(Cl)c(Cl)c5)cc(C)nc34)CC2)cc1]

Preparation was made using a similar procedure as described in example 6. Starting materials were 8-bromo-2-methylquinolin-4-yl)-(3,4-dichlorobenzyl)-amine and N,N-bis(2-chloroethyl)-p-toluenesulfonamide.

Yield: 26%.

ESI-MS [M+H]+=555.2/557.2 calculated for $C_{28}H_{28}Cl_2N_4O_2S$=556 g/mole

Example 18

(3,4-Dichlorobenzyl)-(2-methyl-8-piperazin-1-yl-quinolin-4-yl)-amine dihydrochloride

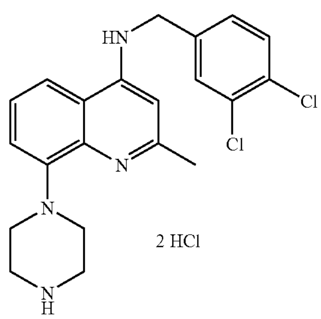 [SMILES: Cc1cc(NCc2ccc(Cl)c(Cl)c2)c2cccc(N3CCNCC3)c2n1 ; "2 HCl"]

(3,4-Dichlorobenzyl)-{2-methyl-8-[4-(toluene-4-sulfonyl)-piperazin-1-yl]-quinolin-4-yl}-amine (example 17, 40 mg, 0.072 mmole) and a mixture of HBr/glacial acetic acid (33%, 1 mL)/0.2 mL) were stirred at 70° C. for 3 hrs. The content of the flask was diluted with water and extracted with ethyl acetate. The aqueous phase was alkalized and extracted with dichloromethane. The organic phases were washed with saturated NaCl solution and concentrated. The residue was crystallized as hydrochloride from isopropanol/iso-propyl ether/ethanol/HCl to give a light fawn salt (17 mg, 50%).

ESI-MS [M+H]+=401.1/405.1 calculated for $C_{21}H_{22}Cl_2N_4$=401 g/mole

Example 19

{2-[4-(3,4-Dichlorobenzylamino)-2-methylquinolin-8-yloxy]-ethyl}-carbamate tert-butyl ester 19.1 [2-(4-Chloro-2-methylquinolin-8-yloxy)-ethyl]-carbamate tert-butyl ester

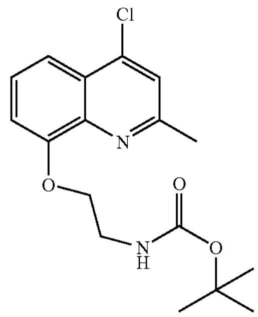 [SMILES: Cc1cc(Cl)c2cccc(OCCNC(=O)OC(C)(C)C)c2n1]

0.6 g Sodium hydride, free of paraffin, was suspended in dimethyl acetamide (50 mL), then 4-chloro-2-methylquinoline-8-ol (1.6 g, 8.26 mmole) was added at RT and the mixture was stirred for 1 h. 2-(boc-amino)ethylbromide was added dropwise and the mixture was kept on stirring for 48 hrs. The content of the flask was poured into half concentrated NaCl solution and extracted with ethyl acetate. The organic phases were washed with water and saturated NaCl solution, dried and concentrated. Dimethyl acetamide was removed in vacuo and the residue was precipitated from isopropyl ether to give a light fawn solid (2.50 g, 90%).

ESI-MS [M+H]+=337.2 calculated for $C_{17}H_{21}ClN_2O_3$=337 g/mole 19.2 {2-[4-(3,4-Dichlorobenzylamino)-2-methylquinolin-8-yloxy]-ethyl}-carbamate tert-butyl ester

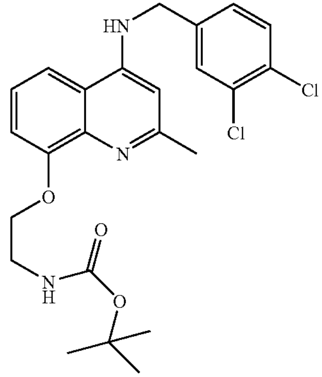 [SMILES: Cc1cc(NCc2ccc(Cl)c(Cl)c2)c2cccc(OCCNC(=O)OC(C)(C)C)c2n1]

[2-(4-Chloro-2-methylquinolin-8-yloxy)-ethyl]-carbamate tert-butyl ester (1.30 g, 3.86 mmole), 3,4-dichlorobenzylamine (1.36 g, 7.72 mmole) and a catalytic effective amount of copper(II)sulphate pentahydrate in dimethylsulfoxide (0.2 mL) were stirred at 155° C. for 30 min in a microwave oven. The organic phases were washed with water and saturated NaCl solution, dried and the solvent was removed. The residue thus obtained was purified using silica gel chromatography, eluting with dichloromethane:water 90:10. Precipitation in ethyl acetate gave a brownish solid (230 mg, 13%).

ESI-MS [M+H]+=476.2/478.2 calculated for $C_{24}H_{27}Cl_2N_3O_3$=476 g/mole

Example 20

[8-(2-Aminoethoxy)-2-methylquinolin-4-yl]-(3,4-dichlorobenzyl)-amine dihydrochloride

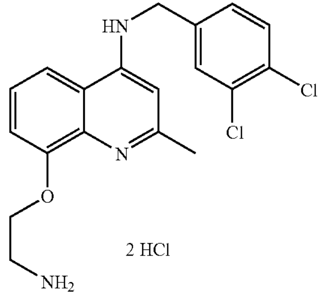 [SMILES: Cc1cc(NCc2ccc(Cl)c(Cl)c2)c2cccc(OCCN)c2n1 ; "2 HCl"]

[2-(4-Chloro-2-methylquinolin-8-yloxy)-ethyl]carbamate tert-butyl ester (example 19, 230 mg, 0.483 mmole) was stirred in isopropanol/HCl (5-6N, 10 mL) at RT overnight. The content of the flask was diluted with isopropyl ether and the precipitated solid was filtered off to obtain a white salt (215 mg, 99%).

ESI-MS [M+H]+=377.0/379.0 calculated for $C_{16}H_{16}Cl_2N_3O$=376 g/mole

Example 21

N-{2-[4-(3,4-Dichlorobenzylamino)-2-methylquinolin-8-yloxy]-ethyl}-ethanesulfonamide

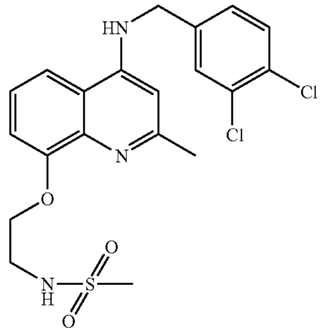 [SMILES: Cc1cc(NCc2ccc(Cl)c(Cl)c2)c2cccc(OCCNS(C)(=O)=O)c2n1]

[8-(2-Aminoethoxy)-2-methylquinolin-4-yl]-(3,4-dichlorobenzyl)-amine dihydrochloride (example 20, 60 mg, 0.160 mmole) and methanesulfonyl chloride (33.8 mg, 0.30 mmole) were dissolved in pyridine and stirred at RT for 12 hrs. The content of the flask was concentrated, mixed with 1N NaOH and extracted with dichloromethane. The organic layer was washed with water and saturated NaCl solution and concentrated. The residue thus obtained was purified using silica gel chromatography, eluting with dichloromethane:methanol 95:5. After precipitation in ethyl acetate a white solid was obtained (12 mg, 17%).

ESI-MS [M+H]+=454.0/458.1 calculated for $C_{20}H_{21}Cl_2N_3O_3S$=454 g/mole

Example 22

N-{2-[4-(3,4-Dichlorobenzylamino)-2-methylquinolin-8-yloxy]-ethyl}-phenylamide

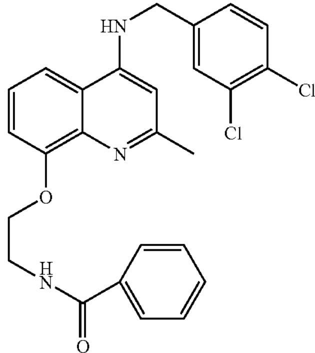 [SMILES: Cc1cc(NCc2ccc(Cl)c(Cl)c2)c2cccc(OCCNC(=O)c3ccccc3)c2n1]

Preparation was made using a similar procedure as described in example 21. Starting materials were [8-(2-aminoethoxy)-2-methylquinolin-4-yl]-(3,4-dichlorobenzyl)-amine dihydrochloride and benzoyl chloride.

Yield: 37%.

ESI-MS [M+H]+=480.1/484.1 calculated for $C_{26}H_{23}Cl_2N_3O_2$=480 g/mole

Example 23

N-{2-[4-(3,4-Dichlorobenzylamino)-2-methylquinolin-8-yloxy]-ethyl}-benzamide hydrochloride

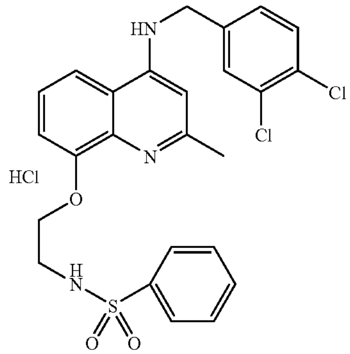 [SMILES: Cl ; Cc1cc(NCc2ccc(Cl)c(Cl)c2)c2cccc(OCCNS(=O)(=O)c3ccccc3)c2n1]

Preparation was made using a similar procedure as described in example 21. Starting materials were [8-(2-aminoethoxy)-2-methylquinolin-4-yl]-(3,4-dichlorobenzyl)-amine dihydrochloride and phenylsulfonyl chloride.

Yield: 8%.

ESI-MS [M+H]+=516.1/520.0 calculated for $C_{25}H_{23}Cl_2N_3O_3S$=516 g/mole

Example 24

N-{2-[4-(3,4-Dichlorobenzylamino)-2-methylquinolin-8-yloxy]-ethyl}-acetamide

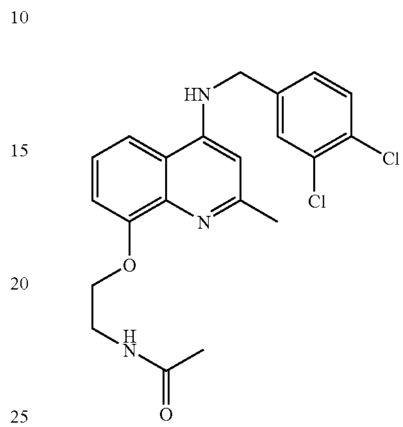

Preparation was made using a similar procedure as described in example 21. Starting materials were [8-(2-aminoethoxy)-2-methylquinolin-4-yl]-(3,4-dichlorobenzyl)-amine dihydrochloride and acetylchloride.

Yield: 65%.

ESI-MS [M+H]+=418.1/422.1 calculated for $C_{21}H_{21}Cl_2N_3O_2$=418 g/mole

Example 26

N-{2-[4-(3,4-Dichlorobenzylamino)-2-methylquinolin-8-yloxy]-ethyl}-isobutyramide

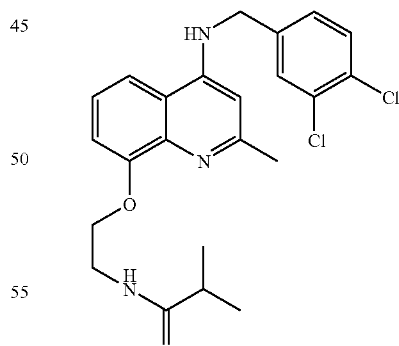

Preparation was made using a similar procedure as described in example 21. Starting materials were [8-(2-aminoethoxy)-2-methylquinolin-4-yl]-(3,4-dichlorobenzyl)-amine dihydrochloride and isobutyrylchloride.

Yield: 11%.

ESI-MS [M+H]+=446.1/450.1 calculated for $C_{23}H_{25}Cl_2N_3O_2$=446 g/mole

Example 27

Ethanesulfonic {2-[4-(3,4-Dichloro-benzylamino)-2-methylquinolin-8-yloxy]-ethyl}-amide

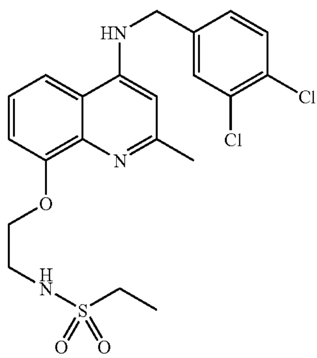 [SMILES: CCS(=O)(=O)NCCOc1cccc2c(NCc3ccc(Cl)c(Cl)c3)cc(C)nc12]

Preparation was made using a similar procedure as described in example 21. Starting materials were [8-(2-aminoethoxy)-2-methylquinolin-4-yl]-(3,4-dichlorobenzyl)-amine dihydrochloride and ethanesulfonyl chloride.

Yield: 19%.

ESI-MS [M+H]+=468.0/472.0 calculated for $O_{21}H_{23}Cl_2N_3O_3S$=468 g/mole

Example 28

Naphthyl-2-sulfonic {2-[4-(3,4-dichlorobenzylamino)-2-methylquinolin-8-yloxy]-ethyl}-amide

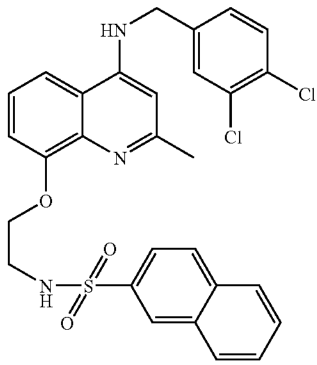 [SMILES: Cc1cc(NCc2ccc(Cl)c(Cl)c2)c2cccc(OCCNS(=O)(=O)c3ccc4ccccc4c3)c2n1]

Preparation was made using a similar procedure as described in example 21. Starting materials were [8-(2-aminoethoxy)-2-methylquinolin-4-yl]-(3,4-dichlorobenzyl)-amine dihydrochloride and naphthyl-2-sulfonic chloride.

Yield: 27%.

ESI-MS [M+H]+=566.1/570.1 calculated for $C_{29}H_{25}Cl_2N_3O_3S$=566 g/mole

Example 29

N-{2-[4-(3,4-Dichlorobenzylamino)-2-methylquinolin-8-yloxy]-ethyl}-C,C,C-trifluoromethanesulfonamide

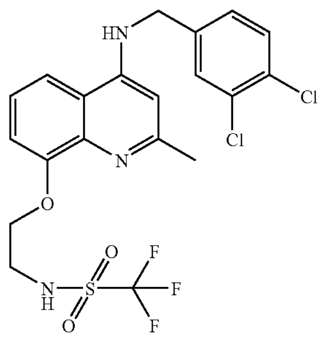 [SMILES: Cc1cc(NCc2ccc(Cl)c(Cl)c2)c2cccc(OCCNS(=O)(=O)C(F)(F)F)c2n1]

Preparation was made using a similar procedure as described in example 21. Starting materials were [8-(2-aminoethoxy)-2-methylquinolin-4-yl]-(3,4-dichlorobenzyl)-amine dihydrochloride and trifluoromethanesulfonyl chloride.

Yield: 40%.

ESI-MS [M+H]+=508.0/512.0 calculated for $C_{20}H_{18}Cl_2F_3N_3O_3S$=508 g/mole Example 30

Pyridine-3-sulfonic {2-[4-(3,4-dichlorobenzylamino)-2-methylquinolin-8-yloxy]-ethyl}amide

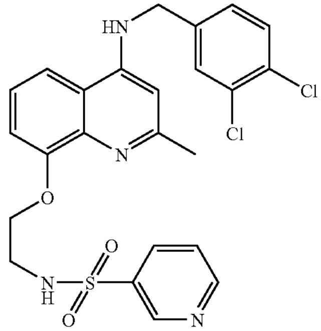 [SMILES: Cc1cc(NCc2ccc(Cl)c(Cl)c2)c2cccc(OCCNS(=O)(=O)c3cccnc3)c2n1]

Preparation was made using a similar procedure as described in example 21. Starting materials were [8-(2-aminoethoxy)-2-methylquinolin-4-yl]-(3,4-dichlorobenzyl)-amine dihydrochloride and pyridine-3-sulfonyl chloride.

Yield: 28%.

ESI-MS [M+H]+=517.0/521.0 calculated for $C_{24}H_{22}Cl_2N_4O_3S$=517 g/mole

Example 31

2-Methylpropane-1-sulfonic {2-[4-(3,4-dichlorobenzylamino)-2-methylquinolin-8-yloxy]-ethyl}-amide

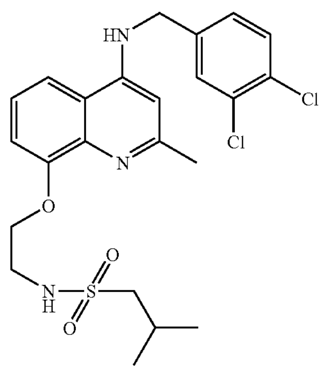 [SMILES: Cc1cc(NCc2ccc(Cl)c(Cl)c2)c2cccc(OCCNS(=O)(=O)CC(C)C)c2n1]

Preparation was made using a similar procedure as described in example 21. Starting materials were [8-(2-aminoethoxy)-2-methylquinolin-4-yl]-(3,4-dichlorobenzyl)-amine dihydrochloride and isobutanesulfonyl chloride.

Yield: 14%.

ESI-MS [M+H]+=496.1/500.1 calculated for $C_{23}H_{27}Cl_2N_3O_3S$=496 g/mole

Example 32

N-{2-[4-(3,4-Dichloro-benzylamino)-2-methylquinolin-8-yloxy]-ethyl}-C-phenyl-methanesulfonamide

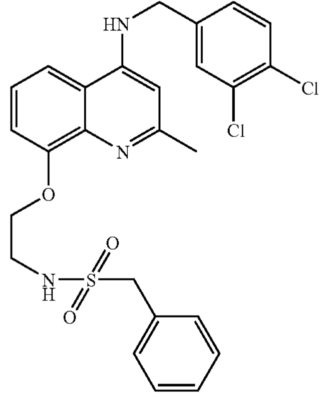 [SMILES: Cc1cc(NCc2ccc(Cl)c(Cl)c2)c2cccc(OCCNS(=O)(=O)Cc3ccccc3)c2n1]

Preparation was made using a similar procedure as described in example 21. Starting materials were [8-(2-aminoethoxy)-2-methylquinolin-4-yl]-(3,4-dichlorobenzyl)-amine dihydrochloride and phenylmethanesulfonyl chloride.

Yield: 3%.

ESI-MS [M+H]+=530.1/534.1 calculated for $C_{26}H_{25}Cl_2N_3O_3S$=530 g/mole

Example 33

[2-(4-{[(S)—((S)-1-Allyl-piperidin-2-yl)-phenylmethyl]-amino}-2-methylquinolin-8-yloxy)ethyl]-carbamate tert-butyl ester

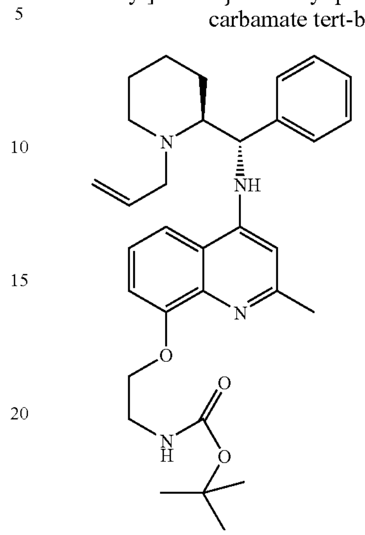

Preparation was made using a similar procedure as described in example 19, method 19.2. Starting materials were 2-(4-chloro-2-methylquinolin-8-yloxy)-ethyl]-carbamate tert-butyl ester (200 mg, 0.594 mmole) and C—[(S)—C—((S)-1-allyl-piperidin-2-yl)-C-phenyl]-methylamine (274 mg, 1.19 mmole).

Yield: 18%.

ESI-MS [M+H]+=531.4 calculated for $C_{32}H_{42}N_4O_3$=531 g/mole

Example 34

[(S)—((S)-1-Allylpiperidin-2-yl)-phenyl methyl]-[8-(2-aminoethoxy)-2-methylquinolin-4-yl]-amine

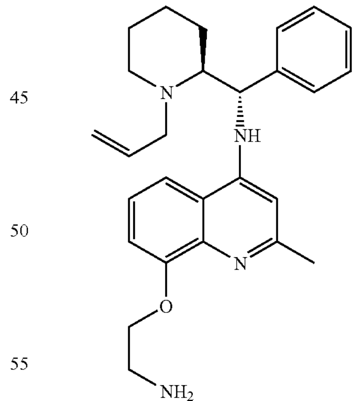

Preparation was made using a similar procedure as described in example 19, method 19.2. Starting materials were 2-(4-chloro-2-methylquinolin-8-yloxy)-ethyl]-carbamate tert-butyl ester (200 mg, 0.594 mmole) and C—[(S)—C—((S)-1-allyl-piperidin-2-yl)-C-phenyl]-methylamine (274 mg, 1.19 mmole).

Yield: 78%.

ESI-MS [M+H]+=431.4 calculated for $C_{27}H_{34}N_4O$=431 g/mole

Example 35

N-[2-(4-{[(S)—((S)-1-Allylpiperidin-2-yl)-phenylmethyl]-amino}-2-methylquinolin-8-yloxy)ethyl] methanesulfonamide

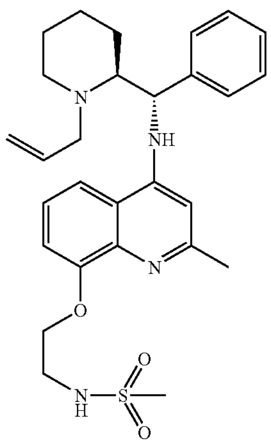 [SMILES: C=CCN1CCCC[C@H]1[C@@H](Nc1cc(C)nc2c(OCCNS(C)(=O)=O)cccc12)c1ccccc1]

Preparation was made using a similar procedure as described in example 21. Starting materials were [(S)—((S)-1-allylpiperidin-2-yl)-phenylmethyl]-[8-(2-aminoethoxy)-2-methylquinolin-4-yl]-amine (example 34) and methanesulfonyl chloride.

Yield: 33%.

ESI-MS [M+H]+=509.3 calculated for $C_{27}H_{35}ClN_4$=509 g/mole

Example 36

[8-(2-Aminoethoxy)-2-methylquinolin-4-yl]-(2,4-dichlorobenzyl)-amine

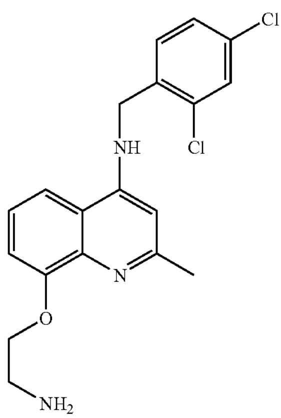 [SMILES: Cc1cc(NCc2ccc(Cl)cc2Cl)c2cccc(OCCN)c2n1]

Preparation was made using a similar procedure as described in example 20. Starting materials were [2-(4-chloro-2-methylquinoline-8-yloxy)-ethyl]-carbamate tert-butyl ester and 2,4-dichlorobenzylamine.

Yield: 30%.

ESI-MS [M+H]+=376.2/378.2 calculated for $C_{19}H_{19}Cl_2N_3O$=376 g/mole

Example 37

N-(2-{2-Methyl-4-[((S)-phenyl-(S)-piperidin-2-yl-methyl)-amino]-quinolin-8-yloxy}-ethyl)methanesulfonamide dihydrochloride

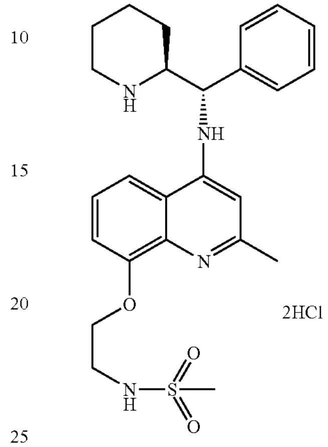

Tris-(dibenzylidenaceton)-dipalladium(0) (19.0 mg, 0.021 mmole) and 1,4-bis(diphenylphosphino)butane (9 mg, 0.021 mmole) were mixed with THF (10 mL). N-[2-(4-{[(S)—((S)-1-Allylpiperidin-2-yl)-phenylmethyl]-amino}-2-methylquinolin-8-yloxy)-ethyl]-methanesulfonamide (example 35, 130 mg, 0.256 mmole) in THF (5 mL) and 2-mercaptobenzoic acid (86.7 mg, 0.562 mmole) in THF (5 mL) were added and the mixture was stirred at RT for 2 hrs. The content of the flask was mixed with 1N NaOH and extracted with dichloromethane. The organic layer was washed with water and saturated NaCl solution and concentrated. The residue thus obtained was cystallized from isopropanol/water/HCl to obtain a white solid (42 mg, 30%).

ESI-MS [M+H]+=469.3 calculated for $C_{25}H_{32}N_4O_3S$=469 g/mole

Example 38

N-{2-[4-(2,4-Dichlorobenzylamino)-2-methylquinolin-8-yloxy]-ethyl}-methanesulfonamide

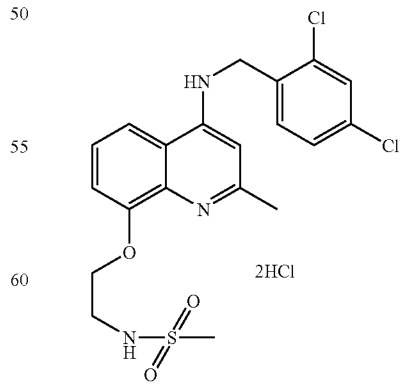

Preparation was made using a similar procedure as described in example 21. Starting materials were [8-(2-aminoethoxy)-2-methylquinolin-4-yl]-(2,4-dichlorobenzyl)-amine (example 36) and methanesulfonyl chloride.

Yield: 32%.

ESI-MS [M+H]+=454.2/456.2 calculated for $C_{20}H_{20}Cl_2N_3O_3S$=454 g/mole

Example 39

2-Methylpropane-1-sulfonic {2-[4-(2,4-dichlorobenzylamino)-2-methylquinolin-8-yloxy]-ethyl}-amide

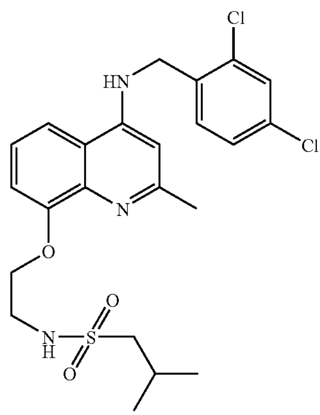 [SMILES: Cc1cc(NCc2ccc(Cl)cc2Cl)c2cccc(OCCNS(=O)(=O)CC(C)C)c2n1]

Preparation was made using a similar procedure as described in example 21. Starting materials were [8-(2-aminoethoxy)-2-methylquinolin-4-yl]-(2,4-dichlorobenzyl)-amine dihydrochloride (example 36) and isobutanesulfonyl chloride.

Yield: 25%.

ESI-MS [M+H]+=496.3/498.2 calculated for $C_{23}H_{27}Cl_2N_3O_3S$=496 g/mole

Example 40

Pyridin-3-sulfonic (2-{2-methyl-4-[((S)-phenyl-(S)-piperidin-2-yl-methyl)-amino]-quinolin-8-yloxy}-ethyl)-amide dihydrochloride

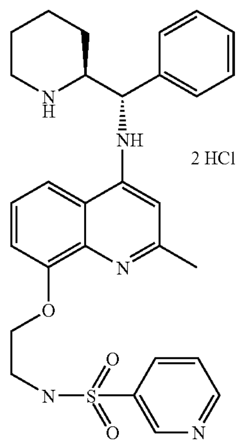 [SMILES: Cc1cc(N[C@@H](c2ccccc2)[C@@H]2CCCCN2)c2cccc(OCCNS(=O)(=O)c3cccnc3)c2n1 ; "2 HCl"]

Preparation was made using a similar procedure as described in example 37. Starting materials were pyridine-3-sulfonic[2-(4-{[(S)—((S)-1-allylpiperidin-2-yl)-phenylmethyl]-amino}-2-methylquinolin-8-yloxy)-ethyl]-amide.

Yield: 34%.

ESI-MS [M+H]+=532.2 calculated for $C_{29}H_{33}N_5O_3S$=532 g/mole

Example 41

4-(3,4-Dichlorobenzylamino)-2-methylquinolin-8-ol

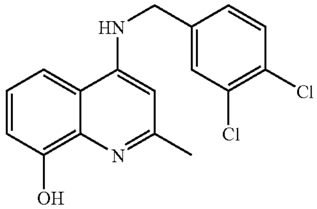 [SMILES: Cc1cc(NCc2ccc(Cl)c(Cl)c2)c2cccc(O)c2n1]

4-Chloro-8-hydroxy-2-methylquinoline (500 mg, 2.58 mmole) and 3,4-dichlorobenzylamine (910 mg, 5.16 mmole) in dimethylsulfoxide (5 mL) were stirred at 140° C. for 90 min in a microwave oven. Water was added and the mixture was decanted to obtain an oily residue. The residue was washed with ethyl acetate to give a brownish solid (350 mg, 41%). ESI-MS [M+H]+=333.1/337.0 calculated for $C_{17}H_{14}Cl_2N_2O$=333 g/mole Example 42

(3,4-Dichlorobenzyl)-(8-isopropoxy-2-methylquinolin-4-yl)-amine hydrochloride

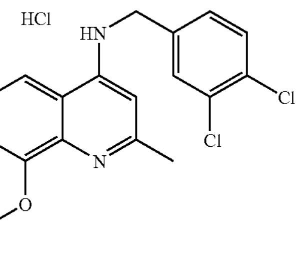

4-(3,4-Dichlorobenzylamino)-2-methylquinolin-8-ol (example 41, 70.0 mg, 0.210 mmole) was suspended in dimethylformamide (5 mL) and mixed with sodium hydride (60% in paraffin liq., 9.24 mg). After stirring for 30 min isopropyliodide (37.5 mg, 0.221 mmole) was added dropwise and the mixture was kept under stirring at RT for 16 hrs. Diluted NaCl solution was added and the mixture was extracted with ethyl acetate. The organic phases were dried and concentrated and the residue thus obtained was purified using silica gel chromatography, eluting with dichloromethane:methanol 90:10. Precipitation in Isopropanol/iso-propyl ether/HCl gave a brownish salt (15 mg, 17%). ESI-MS [M+H]+=375.1/379.2 calculated for $C_{20}H_{20}Cl_2N_2O$=375 g/mole Example 43

(3,4-Dichlorobenzyl)-(2-methyl-8-propoxyquinolin-4-yl)-amine 43.1 4-Chloro-2-methyl-8-propoxyquinoline

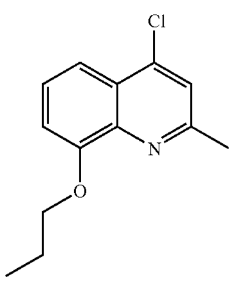 [SMILES: CCCOc1cccc2c(Cl)cc(C)nc12]

4-Chloro-8-hydroxy-2-methylquinoline (500 mg, 2.58 mmole) was suspended in dimethylformamide (4 mL) and mixed with sodium hydride (60% in paraffin liq., 113 mg). After stirring for 1 h, propyliodide (461 mg, 2.71 mmole) in dimethylformamide (1 mL) was added dropwise and the mixture was kept under stirring at RT for 16 hrs. Diluted NaCl solution was added and the mixture was extracted with ethyl acetate. The organic phases were dried, concentrated and the residue thus obtained was purified using silica gel chromatography, eluting with dichloromethane:methanol 95:5. Precipitation in isopropanol/iso-propyl ether/HCl gave the product (300 mg, 49%).

43.2 (3,4-Dichlorobenzyl)-(2-methyl-8-propoxyquinolin-4-yl)-amine

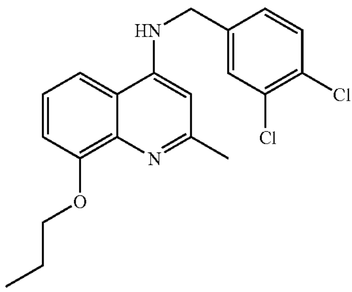 [SMILES: CCCOc1cccc2c(NCc3ccc(Cl)c(Cl)c3)cc(C)nc12]

Preparation was made using a similar procedure as described in example 5, method 5.1. Starting materials were 4-chloro-2-methyl-8-propoxyquinoline and 3,4-dichlorobenzylamine. A catalytic effective amount of copper(II) sulphate hydrate was added to the reaction mixture. The product was purified using silica gel chromatography, eluting with dichloromethane:methanol 90:10.

Yield: 8%.

ESI-MS [M+H]+=375.1/377.1 calculated for $C_{20}H_{20}Cl_2N_2O$=375 g/mole

Example 44

(3,4-Dichlorobenzyl)-(2-methyl-8-phenoxyquinolin-4-yl)-amine

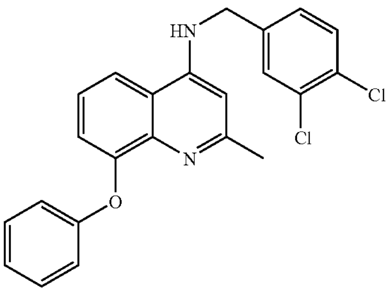 [SMILES: Cc1cc(NCc2ccc(Cl)c(Cl)c2)c2cccc(Oc3ccccc3)c2n1]

Preparation was made using a similar procedure as described in example 43, using 4-chloro-8-hydroxy-2-methylquinoline.

Yield: 25% in last step.

ESI-MS [M+H]+=409.1/411.1 calculated for $C_{23}H_{18}Cl_2N_2O$=409 g/mole

Example 45

(3-Chloro-4-trifluoromethylbenzyl)-(2-methyl-8-propoxyquinoline-4-yl)-amine hydrochloride

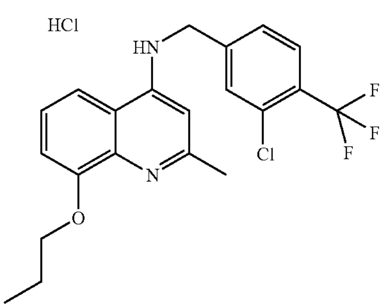 [SMILES: Cl ; CCCOc1cccc2c(NCc3ccc(C(F)(F)F)c(Cl)c3)cc(C)nc12]

Preparation was made using a similar procedure as described in example 43, using 4-chloro-8-hydroxy-2-methylquinoline.

Yield: 25% in last step

ESI-MS [M+H]+=409.2 calculated for $C_{21}H_{20}ClF_3N_2O$=409 g/mole

Example 46

(8-Benzyloxy-2-methylquinolin-4-yl)-(3,4-dichlorobenzyl)-amine

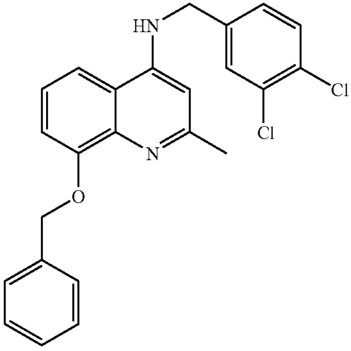 [SMILES: Cc1cc(NCc2ccc(Cl)c(Cl)c2)c2cccc(OCc3ccccc3)c2n1]

Preparation was made using a similar procedure as described in example 43, using 4-chloro-8-hydroxy-2-methylquinoline.

Yield: 11% in last step

ESI-MS [M+H]+=423.3/425.3 calculated for $C_{24}H_{20}Cl_2N_2O$=423 g/mole

Example 47

(3,4-Dichlorobenzyl)-[2-methyl-8-(2-pyrazol-1-yl-ethoxy)-quinolin-4-yl]-amine hydrochloride

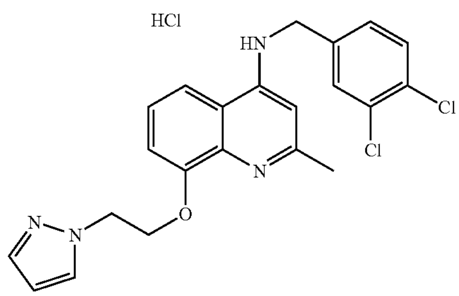 [SMILES: Cl ; Cc1cc(NCc2ccc(Cl)c(Cl)c2)c2cccc(OCCn3cccn3)c2n1]

Preparation was made using a similar procedure as described in example 43, using 4-chloro-8-hydroxy-2-methylquinoline.

Yield: 35% in last step

ESI-MS [M+H]+=427.4/429.4 calculated for $C_{22}H_{21}Cl_3N_4O$=427 g/mole

Example 48

(3,4-Dichlorobenzyl)-[2-methyl-8-(2-morpholin-4-yl-ethoxy)-quinolin-4-yl]-amine dihydrochloride

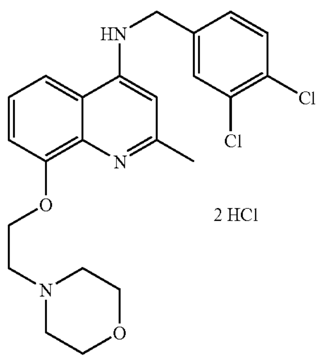 [SMILES: Cc1cc(NCc2ccc(Cl)c(Cl)c2)c2cccc(OCCN3CCOCC3)c2n1 ; "2 HCl"]

Preparation was made using a similar procedure as described in example 43, using 4-chloro-8-hydroxy-2-methylquinoline.

Yield: 19% in last step

ESI-MS [M+H]+=446.3/448.4 calculated for $C_{23}H_{27}Cl_4N_3O_2$=446 g/mole

Example 49

(3,4-Dichlorobenzyl)-[8-(2-methoxyethoxy)-2-methylquinolin-4-yl]-amine

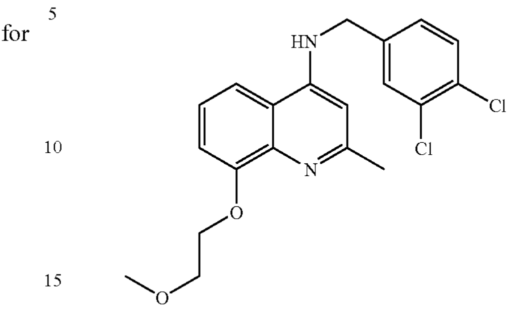

Preparation was made using a similar procedure as described in example 43, using 4-chloro-8-hydroxy-2-methylquinoline.

Yield: 28% in last step

ESI-MS [M+H]+=391.1/393.1 calculated for $C_{20}H_{20}Cl_2N_2O_2$=391 g/mole

Example 50

(3,4-Dichlorobenzyl)-[8-(2-dimethylamino-ethoxy)-2-methylquinolin-4-yl]-amine dihydrochloride

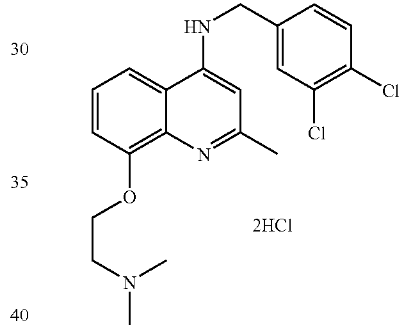

Preparation was made using a similar procedure as described in example 43, using 4-chloro-8-hydroxy-2-methylquinoline.

Yield: 20% in last step

ESI-MS [M+H]+=404.2/406.2 calculated for $O_{21}H_{25}Cl_4N_3O$=404 g/mole

Example 51

(3,4-Dichlorobenzyl)-(8-isobutoxy-2-methylquinolin-4-yl)-amine

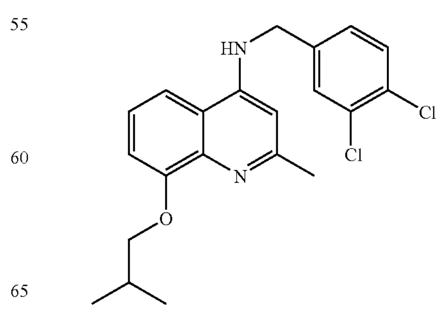

Preparation was made using a similar procedure as described in example 43, using 4-chloro-8-hydroxy-2-methylquinoline.

Yield: 48% in last step

ESI-MS [M+H]+=389.2/391.2 calculated for $C_{21}H_{22}Cl_2N_2O$=389 g/mole

Example 52

(3,4-Dichlorobenzyl)-[2-methyl-8-(2-pyrrolidin-1-yl-ethoxy)-quinolin-4-yl]-amine

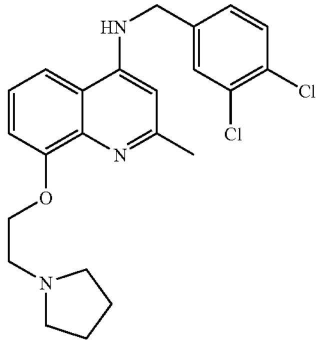 [SMILES: Cc1cc(NCc2ccc(Cl)c(Cl)c2)c2cccc(OCCN3CCCC3)c2n1]

Preparation was made using a similar procedure as described in example 43, using 4-chloro-8-hydroxy-2-methylquinoline.

Yield: 32% in last step

ESI-MS [M+H]+=430.2/432.2 calculated for $C_{23}H_{25}Cl_2N_3O$=430 g/mole

Example 53

[(S)—((S)-1-Allylpiperidin-2-yl)-phenylmethyl]-(8-methoxy-2-methylquinolin-4-yl)-amine

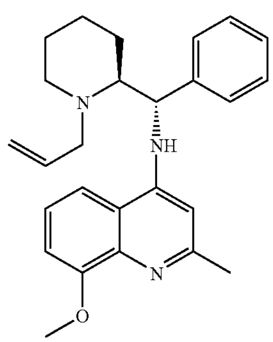 [SMILES: C=CCN1CCCC[C@H]1[C@@H](Nc1cc(C)nc2c(OC)cccc12)c1ccccc1]

Preparation was made using a similar procedure as described in example 5, method 5.1. Starting materials were 4-chloro-8-hydroxy-2-methylquinoline) and C—[(S)—C—((S)-1-allylpiperidin-2-yl)-C-phenyl]-methylamine. Acetonitrile was used as solvent instead of dimethylformamide.

Yield: 32%.

ESI-MS [M+H]+=402.2 calculated for $C_{26}H_{31}N_3O$=402 g/mole

Example 54

(8-Methoxy-2-methylquinolin-4-yl)-((S)-phenyl-(S)-piperidin-2-yl-methyl)-amine

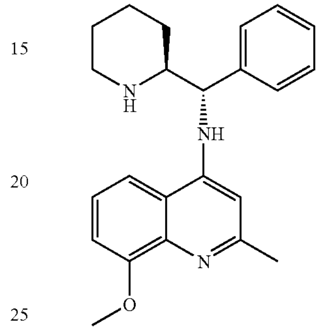

Preparation was made using a similar procedure as described in example 37, using [(S)((S)-1-allyl-piperidin-2-yl)-phenyl]-(8-methoxy-2-methylquinolin-4-yl)-amine (example 53).

Yield: 37%.

ESI-MS [M+H]+=362.1 calculated for $C_{23}H_{29}Cl_2N_3O$=402 g/mole

Example 55

(3,4-Dichlorobenzyl)-[2-methyl-8-(pyridin-2-yloxy)-quinolin-4-yl]-amine

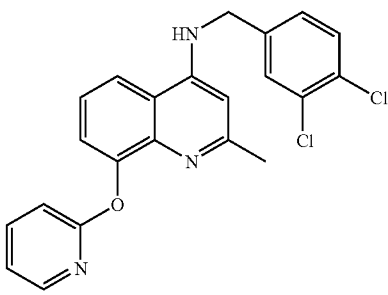 [SMILES: Cc1cc(NCc2ccc(Cl)c(Cl)c2)c2cccc(Oc3ccccn3)c2n1]

Preparation was made using a similar procedure as described in example 1, method 1.3. Starting materials were 4-chloro-2-methyl-8-(pyridin-2-yloxy)-quinoline and 3,4-dichlorobenzylamine.

Yield: 7%.

ESI-MS [M+H]+=410.1/414.1 calculated for $C_{22}H_{17}Cl_2N_3O$=410 g/mole

Example 56

(3,4-Dichloro-benzyl)-(2-methyl-8-trifluoromethoxyquinolin-4-yl)-amine

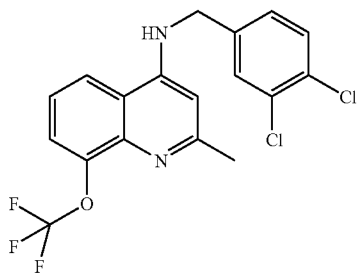 [SMILES: Cc1cc(NCc2ccc(Cl)c(Cl)c2)c2cccc(OC(F)(F)F)c2n1]

Preparation was made using a similar procedure as described in example 1, method 1.3. Starting materials were 4-chloro-2-methyl-8-trifluoromethoxyquinoline and 3,4-dichlorobenzylamine.

Yield: 5%.

ESI-MS [M+H]+=401.1/405.1 calculated for $C_{18}H_{13}Cl_2F_3N_2O$=401 g/mole

Example 57

[(S)-1-(4-Chlorophenyl)-ethyl]-(8-methoxy-2-methylquinolin-4-yl)-amine

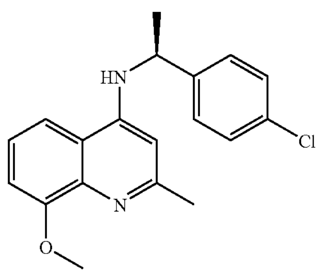 [SMILES: COc1cccc2c(N[C@@H](C)c3ccc(Cl)cc3)cc(C)nc12]

Preparation was made using a similar procedure as described in example 41. Starting materials were 4-chloro-8-methoxy-2-methylquinoline and (S)-1-(4-chloro-phenyl) ethylamine.

Yield: 28%.

ESI-MS [M+H]+=327.1/329.1 calculated for $C_{19}H_{19}ClN_2O$=327 g/mole

Example 58

[(R)-1-(4-Chlorophenyl)-ethyl]-(8-methoxy-2-methylquinolin-4-yl)-amine

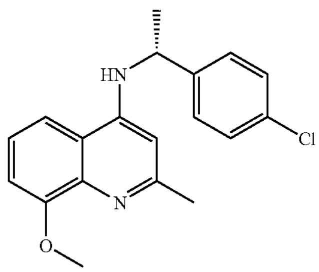 [SMILES: COc1cccc2c(N[C@H](C)c3ccc(Cl)cc3)cc(C)nc12]

Preparation was made using a similar procedure as described in example 41. Starting materials were 4-chloro-8-methoxy-2-methylquinoline and (R)-1-(4-chloro-phenyl) ethylamine.

Yield: 64%.

ESI-MS [M+H]+=327.2 calculated for $C_{19}H_{19}ClN_2O$=327 g/mole

Example 59

[(S)—((S)-1-Allylpiperidin-2-yl)-phenylmethyl]-(2-methylquinolin-4-yl)-amine

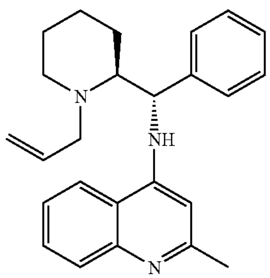 [SMILES: C=CCN1CCCC[C@H]1[C@@H](Nc1cc(C)nc2ccccc12)c1ccccc1]

Preparation was made using a similar procedure as described in example 5, method 5.1. Starting materials were 4-chloro-2-methylquinoline and C—[(S)—C—((S)-1-allylpiperidin-2-yl)C-phenyl]-methylamine. Acetonitrile was used as solvent instead of dimethylformamide.

Yield: 64%.

ESI-MS [M+H]+=372.3/373.3 calculated for $C_{25}H_{29}N_3$=372 g/mole

Example 60

(2-Methylquinolin-4-yl)-((S)-phenyl-(S)-piperidin-2-yl-methyl)-amine

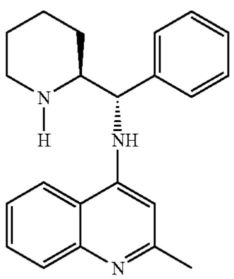 [SMILES: Cc1cc(N[C@@H](c2ccccc2)[C@@H]2CCCCN2)c2ccccc2n1]

Preparation was made using a similar procedure as described in example 37, using [(S)((S)-1-allylpiperidin-2-yl)-phenylmethyl]-(2-methylquinolin-4-yl)-amine (example 59).

Yield: 60%.

ESI-MS $[M+H]^+$=332.2/333.3 calculated for $C_{22}H_{25}N_3$=331 g/mole

Example 61

(S)—((S)-1-Methylpiperidin-2-yl)-phenylmethyl]-(2-methylquinolin-4-yl)-amine dihydrochloride

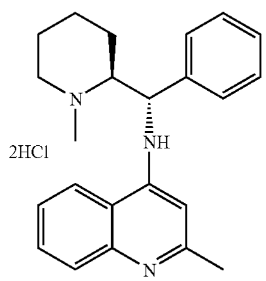 [SMILES: "2HCl" ; Cc1cc(N[C@@H](c2ccccc2)[C@@H]2CCCCN2C)c2ccccc2n1]

(2-Methylquinolin-4-yl)-((S)-phenyl-(S)-piperidin-2-yl-methyl)-amine (example 60, 27 mg, 0.08 mmole) was suspended in dichloromethane and mixed with paraformaldehyde (37%, 7 mg) and one drop of acetic acid. Sodium triacetoxyborohydride was added and the mixture was stirred for 14 hrs. The reaction mixture was washed with saturated $NaHCO_3$ solution, the watery phase was washed with dichloromethane and the combined organic phases were dried with sodium sulphate and concentrated. After purification using silica gel chromatography, eluting with dichloromethane: methanol 80:20, the product was precipitated in diethyl ether as hydrochloride (8.40 mg, 25%).

ESI-MS $[M+H]^+$=346.3/347.2 calculated for $O_{21}H_{27}N_3$.2HCl=418 g/mole

Example 62

(8-Methoxy-2-methylquinolin-4-yl)-(2-morpholin-4-yl-1-phenyl)-ethylamine

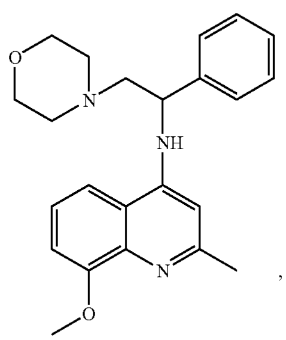 [SMILES: COc1cccc2c(NC(CN3CCOCC3)c3ccccc3)cc(C)nc12 ; ","]

Preparation was made using a similar procedure as described in example 68. Starting materials were 4-chloro-2-methylquinoline and 2-morpholin-4-yl-1-phenyl-ethylamine.

Yield: 17%.

ESI-MS $[M+H]^+$=378.1/379.1 calculated for $C_{23}H_{27}N_3O_2$=377 g/mole

Example 63

(8-Methoxy-2-methyl-quinolin-4-yl)-(1-phenyl-2-piperidin-1-yl)-ethylamine

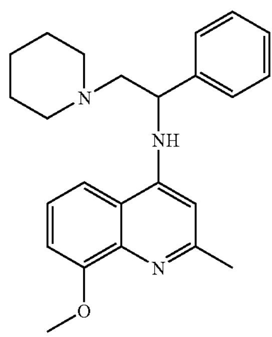 [SMILES: COc1cccc2c(NC(CN3CCCCC3)c3ccccc3)cc(C)nc12]

Preparation was made using a similar procedure as described in example 68. Starting materials were 4-chloro-2-methylquinoline and 1-phenyl-2-piperidin-1-yl-ethylamine.

Yield: 34%.

ESI-MS $[M+H]^+$=376.3/377.2 calculated for $C_{24}H_{29}N_3O$=376 g/mole

Example 64

[(4-Chlorophenyl)-phenylmethyl]-(8-methoxy-2-methylquinolin-4-yl)-amine

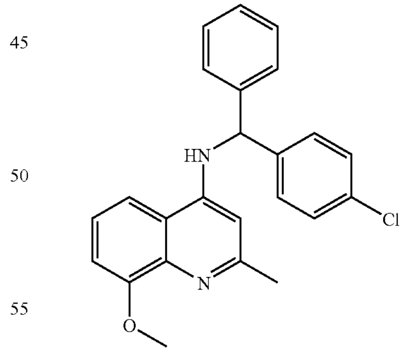

Preparation was made using a similar procedure as described in example 5, method 5.1. Starting materials were 4-chloro-2-methylquinoline and C-(4-chloro-phenyl)-C-phenylmethylamine.

Yield: 57%.

ESI-MS [M+H]+=389.2 calculated for $C_{24}H_{21}ClN_2O$=389 g/mole

Example 65

[1-(4-Chlorophenyl)-2-morpholin-4-yl-ethyl]-(8-methoxy-2-methylquinolin-4-yl)-amine

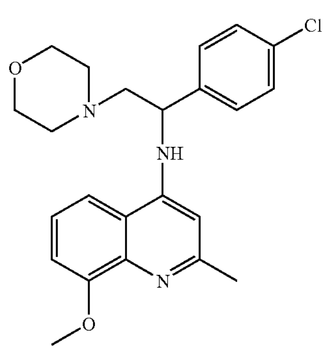 [SMILES: COc1cccc2c(NC(CN3CCOCC3)c3ccc(Cl)cc3)cc(C)nc12]

Preparation was made using a similar procedure as described in example 68. Starting materials were 4-chloro-2-methylquinoline and 1-(4-chlorophenyl)-2-morpholin-4-yl-ethylamine.

Yield: 29%.

ESI-MS $[M+H]^+$=412.1/414.1 calculated for $C_{23}H_{26}ClN_3O_2$=412 g/mole

Example 66

[1-(4-Chlorophenyl)-2-piperidin-1-yl-ethyl]-(8-methoxy-2-methylquinolin-4-yl)-amine

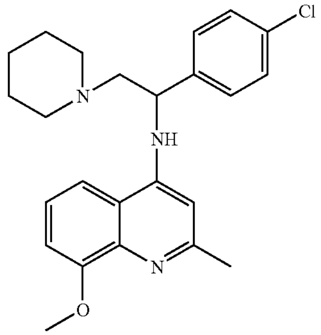 [SMILES: COc1cccc2c(NC(CN3CCCCC3)c3ccc(Cl)cc3)cc(C)nc12]

Preparation was made using a similar procedure as described in example 68. Starting materials were 4-chloro-2-methylquinoline and 1-(4-chlorophenyl)-2-piperidin-1-yl-ethylamine.

Yield: 84%.

ESI-MS [M+H]+=331.2/332.3 calculated for $C_{24}H_{28}ClN_3O$=410 g/mole

Example 67

[1-(4-Chloro-phenyl)-2-pyrrolidin-1-yl-ethyl]-(8-methoxy-2-methyl-quinolin-4-yl)-amine

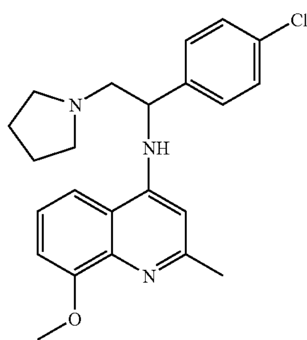 [SMILES: COc1cccc2c(NC(CN3CCCC3)c3ccc(Cl)cc3)cc(C)nc12]

Preparation was made using a similar procedure as described in example 68. Starting materials were 4-chloro-2-methylquinoline and 1-(4-chlorophenyl)-2-pyrrolidin-1-yl-ethylamine.

Yield: 28%.

ESI-MS $[M+H]^+$=396.3/398.3 calculated for $C_{23}H_{26}ClN_3O$=396 g/mole

Example 68

(rac)-1-(4-Chlorophenyl)-N*1*-(8-methoxy-2-methylquinolin-4-yl)-N*2*,N*2*-dimethylethane-1,2-diamine dihydrochloride

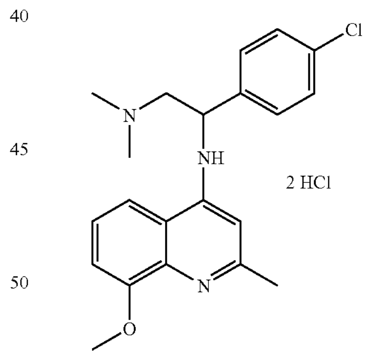

4-Chloro-8-methoxy-2-methylquinoline (2.00 g, 9.63 mmole), 1-(4-chlorophenyl)N*2*,N*2*-dimethylethane-1,2-diamine (2.30 g, 11.6 mmole), sodium tert-butylate (1.3 g, 13.5 mmole), tris(dibenzylidenaceton)-dipalladium(0) (0.18 g, 0.193 mmole) and 2-dicyclohexyl-phosphino-2(N,N-dimethylamino)biphenyl (0.27 g, 0.674 mmole) were stirred at 150° C. under nitrogen atmosphere in a microwave oven for 30 min. The reaction mixture was dissolved in ethyl acetate and filtered. The filtrate was extracted with water. The organic phases were dried, concentrated and the residue was purified using silica gel chromatography, eluting with dichloromethane:methanol 90:10. Precipitation in isopropanol/HCl and in ethyl acetate gave the product (1.55 g, 36%).

ESI-MS $[M+H]^+$=370.1/372.1 calculated for $O_{21}H_{24}ClN_3O.2HCl$=442 g/mole Example 69

(8-Methoxy-2-methylquinolin-4-yl)-(1-phenyl-2-pyrrolidin-1-ylethyl)-amine

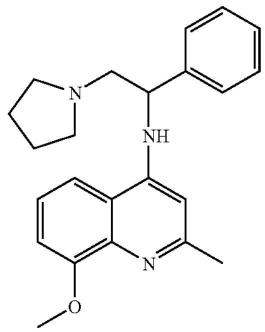 [SMILES: COc1cccc2c(NC(CN3CCCC3)c3ccccc3)cc(C)nc12]

Preparation was made using a similar procedure as described in example 68. Starting materials were 4-chloro-2-methylquinoline and 1-phenyl-2-pyrrolidin-1-yl-ethylamine.

Yield: 41%.

ESI-MS $[M+H]^+$=362.1/363.2 calculated for $C_{23}H_{27}N_3O$=361 g/mole

Example 70

[(4-Chlorophenyl)-(1-methyl-1H-imidazol-2-yl)-methyl]-(8-methoxy-2-methylquinoline-4-yl)amine

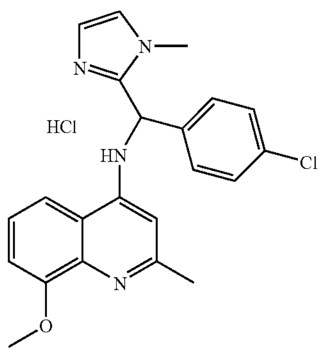 [SMILES: COc1cccc2c(NC(c3ccc(Cl)cc3)c3nccn3C)cc(C)nc12 ; Cl]

Preparation was made using a similar procedure as described in example 68. Starting materials were 4-chloro-2-methylquinoline and C-(4-chlorophenyl)-C-(1-methyl-1H-imidazol-2-yl)-methylamine.

Yield: 4%.

ESI-MS [M+H]+=393.2/395.2 calculated for $C_{22}H_{21}ClN_4O$=393 g/mole

Example 71

N*1*-(8-Methoxy-2-methylquinolin-4-yl)-N*2*,N*2*-dimethyl-1-phenylethane-1,2-diamine

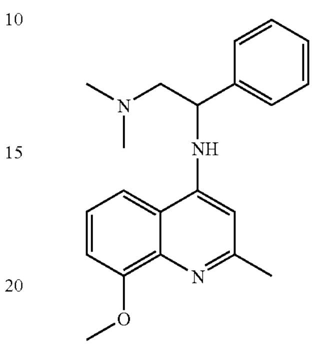

Preparation was made using a similar procedure as described in example 68. Starting materials were 4-chloro-2-methylquinoline and N*2*,N*2*-dimethyl-1-phenylethane-1,2-diamine.

Yield: 11%.

ESI-MS $[M+H]^+$=336.2/337.2 calculated for $O_{21}H_{25}N_3O$=335 g/mole

Example 72

[(4-Chlorophenyl)-cyclopropylmethyl]-(8-methoxy-2-methylquinolin-4-yl)-amine

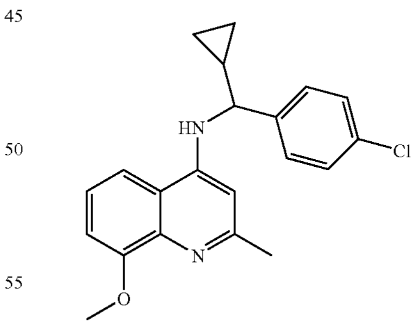

Preparation was made using a similar procedure as described in example 68. Starting materials were 4-chloro-2-methylquinoline and N*2*,N*2*-dimethyl-1-phenylethane-1,2-diamine.

Yield: 8%.

ESI-MS [M+H]+=353.2/355.2 calculated for $C_{21}H_{22}Cl_2N_2O$=353 g/mole

Example 73

[(4-Chlorophenyl)-pyridin-4-ylmethyl]-(8-methoxy-2-methylquinolin-4-yl)-amine

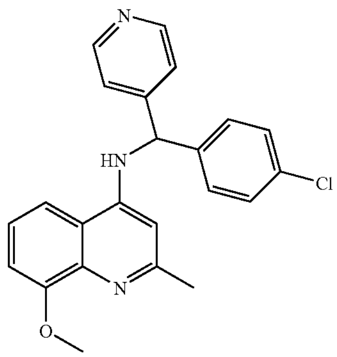 [SMILES: COc1cccc2c(NC(c3ccncc3)c3ccc(Cl)cc3)cc(C)nc12]

Preparation was made using a similar procedure as described in example 19, method 19.2. Starting materials were 4-chloro-8-methoxy-2-methylquinoline and C-(4-chlorophenyl)-C-pyridin-4-yl-methylamine. Acetonitrile was used as solvent instead of dimethylformamide.

Yield: 2%.

ESI-MS [M+H]+=390.2 calculated for $C_{23}H_{20}ClN_3O$=390 g/mole

Example 74

2-(8-Methoxy-2-methylquinolin-4-ylamino)-2-phenylacetamide

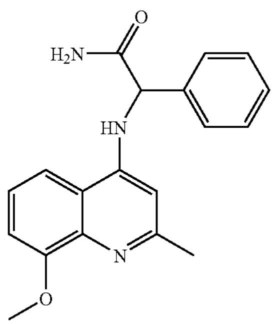 [SMILES: COc1cccc2c(NC(C(N)=O)c3ccccc3)cc(C)nc12]

Preparation was made using a similar procedure as described in example 19, method 19.2. Starting materials were 4-chloro-8-methoxy-2-methylquinoline and 2-amino-2-phenyl-acetamide. Acetonitrile was used as solvent instead of dimethylformamide.

Yield: 59%.

ESI-MS [M+H]+=322.3 calculated for $C_{19}H_{19}N_3O_2$=321 g/mole

Example 75

N*1*-(8-Methoxy-2-methylquinolin-4-yl)-1-phenylethane-1,2-diamine

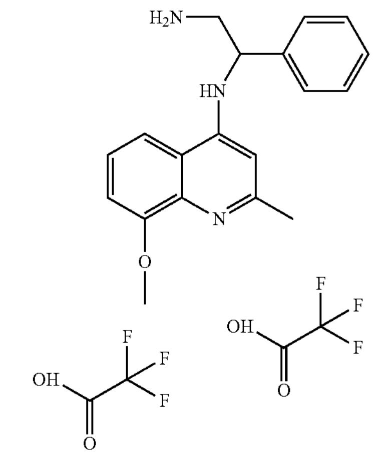

2-(8-Methoxy-2-methylquinolin-4-ylamino)-2-phenylacetamide (example 74, 430 mg, 1.33 mmole) was suspended in tetrahydrofurane (20 mL) and $BH_3xSMe_2$ (2M in tetrahydrofurane) was added dropwise. The mixture was refluxed under stirring for 1 h and then stirred at RT for 12 hrs. The content of the flask was carefully mixed with 2N HCl and refluxed for 2 hrs. The reaction mixture was alkalized and extracted with dichloromethane. The organic phases were dried and concentrated. The residue thus obtained was purified using HPLC (RP-18, eluting with water/acetonitrile) to obtain the product (12%, 83 mg). ESI-MS [M+H]+=294.1 calculated for $C_{22}H_{21}F_6N_3O_5$=293 g/mole Example 76

(S)-1-(4-Chlorophenyl)-N*1*-(8-methoxy-2-methylquinolin-4-yl)-N*2*,N*2*-dimethylethane-1,2-diamine

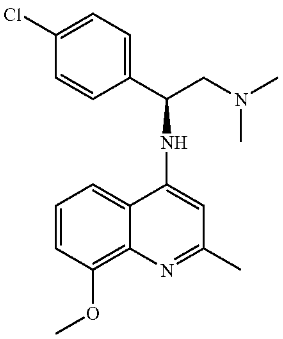 [SMILES: COc1cccc2c(N[C@H](CN(C)C)c3ccc(Cl)cc3)cc(C)nc12]

Preparative chiral chromatography (Chiracel-OD, OD85-15) was used to separate 1-(4-chlorophenyl)-N*1*-(8-methoxy-2-methylquinoline-4-yl)-N*2*,N*2*-dimethylethane-1,2-diamine dihydrochloride (example 68, 200 mg) into its enantiomers. 42 mg (25%) of (S)-1-(4-chlorophenyl)-N*1*-(8-methoxy-2-methylquinoline-4-yl)-N*2*,N*2*-dimethylethane-1,2-diamine were obtained.

ESI-MS $[M+H]^{+}$=370.1/372.1 calculated for $O_{21}H_{24}ClN_3O$=370 g/mole

Example 77

(R)-1-(4-Chlorphenyl)-N*1*-(8-methoxy-2-methylquinoline-4-yl)-N*2*,N*2*-dimethylethane-1,2-diamin

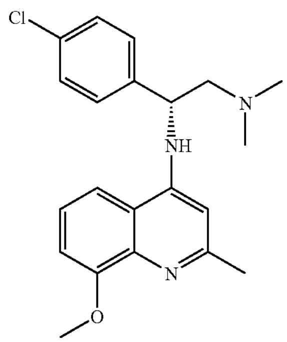 [SMILES: COc1cccc2c(N[C@@H](CN(C)C)c3ccc(Cl)cc3)cc(C)nc12]

Preparative chiral chromatography (Chiracel-OD, OD85-15, n-hexane: isopropanol/$NEt_3$ 850:150:1) was used to separate 1-(4-chlorophenyl)-N*1*-(8-methoxy-2-methylquinoline-4-yl)-N*2*,N*2*-dimethylethane-1,2-diamine dihydrochloride (example 68, 200 mg) into its enantiomers. 37 mg (22%) of (R)-1-(4-chlorophenyl)-N*1*-(8-methoxy-2-methylquinoline-4-yl)-N*2*,N*2*-dimethylethane-1,2-diamine were obtained. ESI-MS [M+H]+=370.1/372.1 calculated for $O_{21}H_{24}ClN_3O$=370 g/mole Example 78

N*2*-Benzyl-N*1*-(8-methoxy-2-methylquinolin-4-yl)-1-phenylethane-1,2-diamine

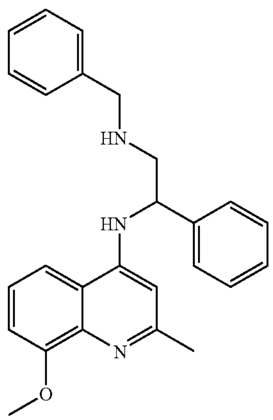 [SMILES: COc1cccc2c(NC(CNCc3ccccc3)c3ccccc3)cc(C)nc12]

N*1*-(8-Methoxy-2-methylquinolin-4-yl)-1-phenylethane-1,2-diamine (Example 75, 150 mg, 0.488 mmole) and benzaldehyde were stirred at RT for 20 hrs. Molecular sieve (4A) was added and the mixture was heated to 60° C. within 2 hrs. $NaBH_4$ was added and the mixture was stirred for 1 h at RT. The resulting mixture was filtered and extracted with dichloromethane. The organic phases were dried and concentrated. The residue was purified using preparative HPLC (RP-18, water/acetonitrile) to obtain the product (21 mg, 11%).

ESI-MS [M+H]+=398.3 calculated for $C_{26}H_{27}N_3O$=398 g/mole

Example 79

N*2*-Isopropyl-N*1*-(8-methoxy-2-methylquinolin-4-yl)-1-phenylethane-1,2-diamine

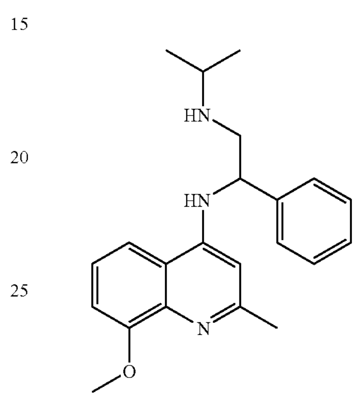

Preparation was made using a similar procedure as described in example 79. Starting materials were N*1*-(8-methoxy-2-methylquinolin-4-yl)-1-phenylethane-1,2-diamine (Example 75) and acetone.

Yield: 27%.

ESI-MS [M+H]+=350.3 calculated for $C_{22}H_{27}N_3O$=349 g/mole

Example 80

(3-Chloro-4-trifluoromethylbenzyl)-(8-methoxy-2-methylquinolin-4-yl)-amine

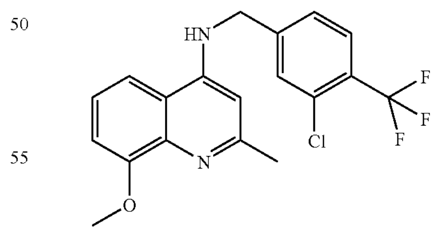

Preparation was made using a similar procedure as described in example 1, method 1.3. Starting materials were 4-chloro-8-methoxy-2-methylquinoline and 3-chloro-4-trifluoromethylbenzylamine.

Yield: 39° A.

ESI-MS [M+H]+=381.2 calculated for $C_{19}H_{16}ClF_3N_2O$=380 g/mole

Example 81

(8-Chlor-2-methylquinolin-4-yl)-(3,4-dichlorobenzyl)-amine

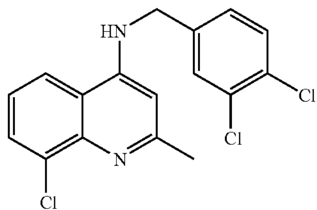 [SMILES: Cc1cc(NCc2ccc(Cl)c(Cl)c2)c2cccc(Cl)c2n1]

Preparation was made using a similar procedure as described in example 1, method 1.3. Starting materials were 4,8-dichloro-2-methylquinoline and 3,4-dichlorobenzylamine.

Yield: 6%.

ESI-MS [M+H]+=351.1/353.1 calculated for $C_{17}H_{13}Cl_3N_2$=352 g/mole

Example 82

(3,4-Dichlorobenzyl)-(8-fluoro-2-methylquinolin-4-yl)-amine

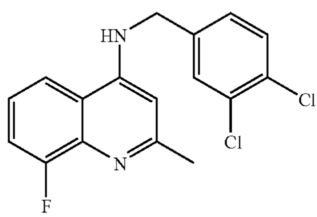 [SMILES: Cc1cc(NCc2ccc(Cl)c(Cl)c2)c2cccc(F)c2n1]

Preparation was made using a similar procedure as described in example 1, method 1.3. Starting materials were 4-chloro-8-fluoro-2-methylquinoline and 3,4-dichlorobenzylamine.

Yield: 24%.

ESI-MS [M+H]+=335.1/337.1 calculated for $C_{17}H_{13}Cl_2FN_2$=335 g/mole

Example 83

(4-Chlorobenzyl)-(2-methyl-8-methylsulfanylquinolin-4-yl)-amine

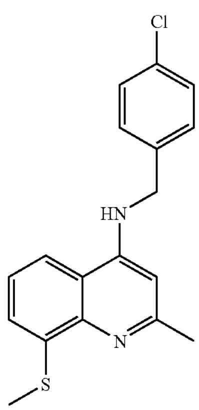 [SMILES: CSc1cccc2c(NCc3ccc(Cl)cc3)cc(C)nc12]

Preparation was made using a similar procedure as described in example 1, method 1.3. Starting materials were 4-chloro-2-methyl-8-methylsulfanylquinoline and 4-chlorobenzylamine.

Yield: 19%.

ESI-MS [M+H]+=329.1 calculated for $C_{18}H_{17}ClN_2S$=329 g/mole

Example 84

(4-Chlorobenzyl)-(2-methyl-8-methoxyquinolin-4-yl)amine

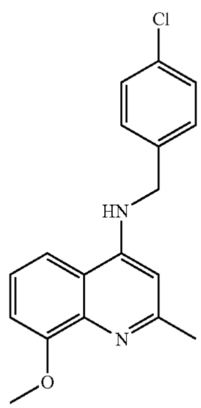 [SMILES: COc1cccc2c(NCc3ccc(Cl)cc3)cc(C)nc12]

Preparation was made using a similar procedure as described in example 1, method 1.3. Starting materials were 4-chloro-2-methyl-8-methoxyquinoline and 4-chlorobenzylamine.

Yield: 72%.

ESI-MS [M+H]+=313.0 calculated for $C_{18}H_{17}ClN_2O$=313 g/mole

Example 85

(3,4-Difluoro-benzyl)-(2,8-dimethyl-quinolin-4-yl)-amine

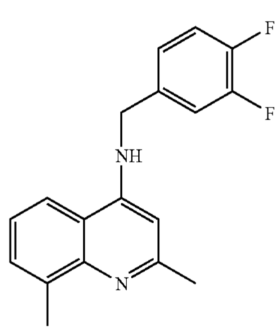 [SMILES: Cc1cc(NCc2ccc(F)c(F)c2)c2cccc(C)c2n1]

Preparation was made using a similar procedure as described in example 1, method 1.3. Starting materials were 4-chloro-2-methyl-8-methylquinoline and 3,4-difluorobenzylamine.

Yield: 19%.

ESI-MS [M+H]+=299.1 calculated for $C_{18}H_{16}F_2N_2$=298 g/mole

Example 86

(3,4-Difluorobenzyl)-(2-methyl-8-methylsulfanylquinolin-4-yl)-amine

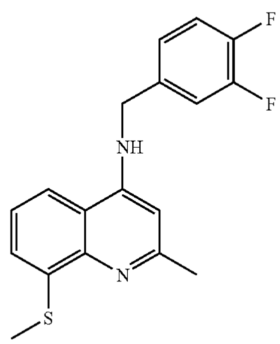 [SMILES: CSc1cccc2c(NCc3ccc(F)c(F)c3)cc(C)nc12]

Preparation was made using a similar procedure as described in example 1, method 1.3. Starting materials were 4-chloro-2-methyl-8-methylsulfanylquinoline and 3,4-difluorobenzylamine.

Yield: 24%.

ESI-MS [M+H]+=331.0 calculated for $C_{18}H_{16}F_2N_2S$=330 g/mole

Example 87

(3,4-Dichlorobenzyl)-(2-methyl-8-methylquinolin-4-yl)-amine

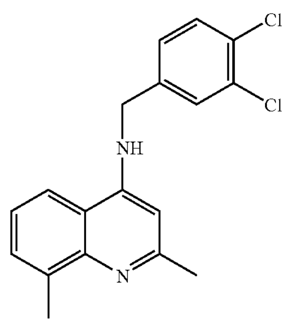 [SMILES: Cc1cc(NCc2ccc(Cl)c(Cl)c2)c2cccc(C)c2n1]

Preparation was made using a similar procedure as described in example 1, method 1.3. Starting materials were 4-chloro-2-methyl-8-methylquinoline and 3,4-dichlorobenzylamine.

Yield: 24%.

ESI-MS [M+H]+=331.0/333.0 calculated for $C_{18}H_{16}Cl_2N_2$=331 g/mole

Example 88

(3,4-Dichlorobenzyl)-(2-methyl-8-methylsulfanylquinolin-4-yl)-amine

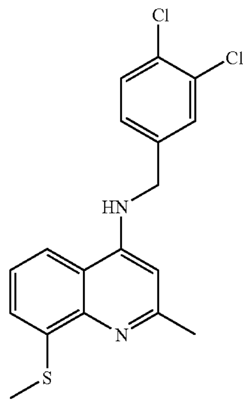 [SMILES: CSc1cccc2c(NCc3ccc(Cl)c(Cl)c3)cc(C)nc12]

Preparation was made using a similar procedure as described in example 1, method 1.3. Starting materials were 4-chloro-2-methyl-8-methylsulfanylquinoline and 3,4-dichlorobenzylamine.

Yield: 48%.

ESI-MS [M+H]+=313.0 calculated for $C_{18}H_{16}Cl_2N_2S$=363 g/mole

Example 89

(3,4-Dichlorobenzyl)-(2-methylquinolin-4-yl)-amine

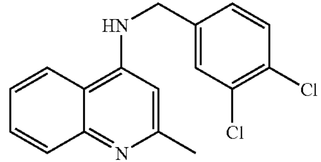 [SMILES: Cc1cc(NCc2ccc(Cl)c(Cl)c2)c2ccccc2n1]

Preparation was made using a similar procedure as described in example 1, method 1.3. Starting materials were 4-chloro-2-methylquinoline and 3,4-dichlorobenzylamine.

Yield: 10%.

ESI-MS [M+H]+=317.0/319.0 calculated for $C_{17}H_{14}Cl_2N_2$=317 g/mole

Example 90

(4-Fluorobenzyl)-(2-methylquinoline-4-yl)-amine

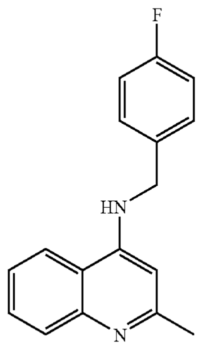 [SMILES: Cc1cc(NCc2ccc(F)cc2)c2ccccc2n1]

Preparation was made using a similar procedure as described in example 1, method 1.3. Starting materials were 4-chloro-2-methylquinoline and 4-fluorobenzylamine.

Yield: 47%.

ESI-MS [M+H]+=267.1 calculated for $C_{17}H_{15}FN_2$=266 g/mole

Example 91

(2,3-Dichloro-benzyl)-(2-methylquinolin-4-yl)-amine

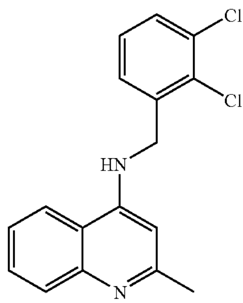 [SMILES: Cc1cc(NCc2cccc(Cl)c2Cl)c2ccccc2n1]

Preparation was made using a similar procedure as described in example 1, method 1.3. Starting materials were 4-chloro-2-methylquinoline and 2,3-dichlorobenzylamine.

Yield: 47%.

ESI-MS [M+H]+=317.0/319.0 calculated for $C_{17}H_{14}Cl_2N_2$=317 g/mole

Example 92

(3,4-Dichlorobenzyl)-(8-methanesulfinyl-2-methylquinolin-4-yl)-amine

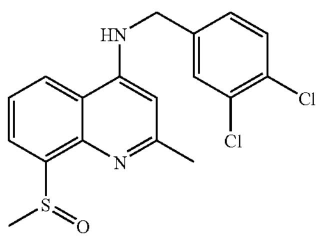 [SMILES: Cc1cc(NCc2ccc(Cl)c(Cl)c2)c2cccc(S(C)=O)c2n1]

$H_2O_2$ (30%, 20.0 mg, 0.55 mmole) was added dropwise to a solution of (3,4-dichlorobenzyl)-(2-methyl-8-methylsulfanylquinolin-4-yl)-amine (100 mg, 0.275 mmole) in acetic acid (3.5 mL) at 0° C. The mixture was stirred at RT for 16 hrs, concentrated by half, 2N NaOH was added and the resulting mixture was extracted with ethyl acetate. The organic phases were dried and concentrated. Precipitation in isopropyl ether gave the product as a white solid (37 mg, 35%).

ESI-MS [M+H]+=379.1/383.1 calculated for $C_{18}H_{16}Cl_2N_2OS$=379 g/mole

Example 93

(3,4-Dichlorobenzyl)-(8-methanesulfonyl-2-methylquinolin-4-yl)-amine

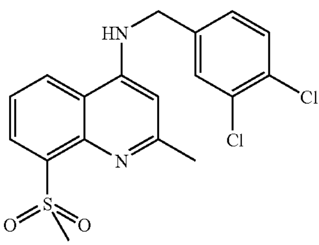 [SMILES: Cc1cc(NCc2ccc(Cl)c(Cl)c2)c2cccc(S(C)(=O)=O)c2n1]

$H_2O_2$ (30%, 18.0 mg, 0.53 mmole) was added dropwise to a solution of (3,4-dichlorobenzyl)-(8-methanesulfinyl-2-methylquinolin-4-yl)-amine (50 mg, 0.132 mmole) in acetic acid (3.5 mL) at 0° C. The mixture was stirred at 70° C. for 16 hrs, concentrated by half, 2N NaOH was added and the resulting mixture was extracted with ethyl acetate. The organic phases were dried and concentrated. Precipitation in ethyl acetate gave the product as white solid (32 mg, 61%).

ESI-MS [M+H]+=395.1/399.0 calculated for $C_{18}H_{16}Cl_2N_2O_2S$=395 g/mole

Example 94

N*4*-Benzyl-N*2*,N*2*-dimethylquinoline-2,4-diamine 94.1 Benzyl-(2-chloroquinolin-4-yl)-amine

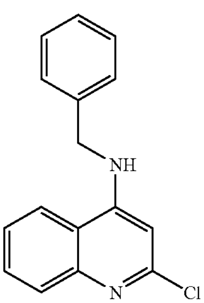 [SMILES: Clc1cc(NCc2ccccc2)c2ccccc2n1]

2,4-Dichloroquinoline (0.70 g, 3.53 mmole) and benzylamine (3.79 g, 35.3 mmole) in ethanol (2 mL) were stirred at 110° C. in a microwave oven for 1 h. Water was added and the mixture was extracted with ethyl acetate. The organic phases were washed with saturated NaCl solution, dried and concentrated. The residue thus obtained was purified using silica gel chromatography, eluting with dichloromethane:methanol 95:5 to give a white solid (330 mg, 35%).

ESI-MS [M+H]+=269.1/271.0 calculated for $C_{16}H_{13}ClN_2$=269 g/mole 94.2 N*4*-Benzyl-N*2*,N*2*-dimethylquinoline-2,4-diamine

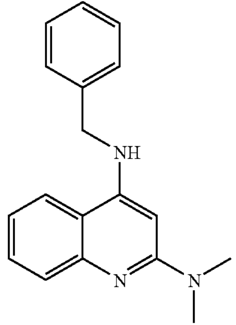 [SMILES: CN(C)c1cc(NCc2ccccc2)c2ccccc2n1]

Benzyl-(2-chloroquinolin-4-yl)-amine (100 mg, 0.372 mmole), copper(II)sulphate pentahydrate (92.9 mg, 0.372 mmole) and dimethylamine (1M in MeOH, 3 mL) were stirred at 150° C. in a microwave oven for 5 hrs. The reaction mixture was dissolved with water and extracted with ethyl acetate. The residue obtained from the organic phases was purified using silica gel chromatography, eluting with dichloromethane:methanol 90:10. Precipitation in isopropyl ether gave a yellowish solid (70.0 mg, 68%).

ESI-MS [M+H]+=278.2/279.2 calculated for $C_{18}H_{19}N_3$=277 g/mole

Example 95

N*4*-(3,4-Dichlorobenzyl)-N*2*,N*2*-dimethylquinoline-2,4-diamine

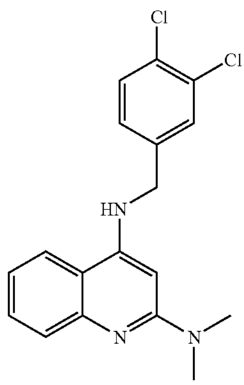 [SMILES: CN(C)c1cc(NCc2ccc(Cl)c(Cl)c2)c2ccccc2n1]

Preparation was made using a procedure similar to example 94. Yield of the desired product was 31% in the last step.

ESI-MS [M+H]+=346.1/350.1 calculated for $C_{18}H_{17}Cl_2N_3$=346 g/mole

Example 96

N*4*-(2,4-Dichlorobenzyl)-N*2*,N*2*-dimethylquinoline-2,4-diamin

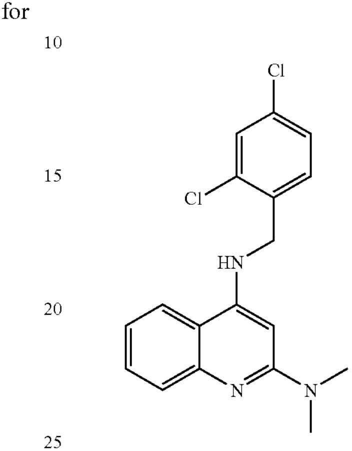

Preparation was made using a procedure similar to example 94. Yield of the desired product was 5% in the last step.

ESI-MS [M+H]+=346.1/350.1 calculated for $C_{18}H_{17}Cl_2N_3$=346 g/mole

Biological Testing

1. Glycine Uptake in Recombinant hGlyT1 Expressing Cells:

Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 µl HBSS (Gibco BRL, #14025-050) with 5 mM L-Alanine (Merck #1007). 80 µl HBSS buffer were added, followed by 10 µl inhibitor or vehicle (10% DMSO) and 10 µl [$^3$H]-glycine (TRK71, Amersham Biosciences) to a final concentration of 200 for initiation of glycine uptake. The plates were placed in a Wallac Microbeta (PerkinElmer) and continuously counted by solid phase scintillation spectrometry during up to 3 hours. Nonspecific uptake was determined in the presence of 10 µM Org24598. $IC_{50}$ calculations were made by four-parametric logistic non-linear regression analysis (GraphPad Prism) using determinations within the range of linear increase of [$^3$H]-glycine incorporation between 60 and 120 min.

2. [$^3$H]-(R)-NPTS Radioligand Binding Assays using Recombinant hGlyT1 Expressing Cell Membranes:

Radioligand binding to human GlyT1c transporter-expressing membranes was measured in duplicate in a total volume of 200 µl in 96-well plates. To 100 µl of membrane suspension (yielding a final membrane protein concentration of 50 µg/ml) in assay buffer (120 mM NaCl, 2 mM KCl, 10 mM Hepes, 1 mM MgCl2, 1 mM $CaCl_2$, pH 7.5) 80 µl of [$^3$H]-(R)NPTS (0.5 nM final) were added in assay buffer. For competition experiments 10 µl of buffer or unlabeled compound solution obtained from dilution series of test compounds in DMSO followed. An intermediate 1:10 dilution in assay buffer yielded a final DMSO concentration of 1%. Non-specific binding was determined in the presence of 10 µM Org24598 (or its racemate Org24461) for [$^3$H]-(R)-NPTS. After incubation at room temperature for 1 h, the incubation mixture was harvested (Tomtec Mach III U Harvester) through 96-well GF/B filter plates (PerkinElmer), presoaked for 1 h with 40 μl per well of 0.1% polyethylene-imine (PEI). After washing twice with ice-cold 50 mM Tris-HCl pH 7.4 buffer, drying and addition of 35 μl scintillator (Beta-plateScint, PerkinElmer) per well followed. The radioactivity was determined by liquid scintillation spectrometry in a MicroBeta (PerkinElmer) plate counter.

Data analysis: For binding of [$^3$H]-(R)-NPTS to cell membranes, the calculation of Kd and Bmax values from the saturation binding assays and the $IC_{50}$ values from the displacement binding was performed by iterative non-linear regression analysis adapted from the 'Ligand' program (Munson and Rodbard, 1980). Radioligand displacement curves in absence or in presence of increasing concentrations of tested compounds were fitted using a one-site fit and the apparent Ki values were calculated from the $IC_{50}$ values using the Cheng-Prusoff equation (Cheng and Prusoff 1973).

The following results were obtained with the compounds of examples 1 to 96:

TABLE 1

| Example | [3H]-(R)-NPTS bindung Ki [μmol] | Glycine uptake $IC_{50}$ [μmol] |
|---|---|---|
| 1 | ≦1 | ≦10 |
| 2 | ≦1 | ≦1000 |
| 3 | ≦1 | ≦10 |
| 4 | ≦1 | ≦100 |
| 5 | ≦0.1 | ≦0.1 |
| 6 | ≦0.1 | ≦1 |
| 7 | ≦1 | ≦1 |
| 8 | ≦1 | ≦10 |
| 9 | ≦0.1 | ≦1 |
| 10 | ≦1 | ≦100 |
| 11 | ≦10 | ≦100 |
| 12 | ≦1 | ≦10 |
| 13 | ≦1 | ≦1 |
| 14 | ≦10 | ≦10 |
| 15 | ≦0.1 | ≦1 |
| 16 | ≦0.1 | ≦1 |
| 17 | ≦1 | ≦10 |
| 18 | ≦0.1 | ≦1 |
| 19 | ≦0.1 | ≦0.1 |
| 20 | ≦0.01 | ≦1 |
| 21 | ≦0.01 | ≦0.1 |
| 22 | ≦0.01 | ≦0.1 |
| 23 | ≦0.01 | ≦1 |
| 24 | ≦0.1 | ≦1 |
| 26 | ≦1 | ≦1 |
| 27 | ≦0.01 | ≦0.01 |
| 28 | ≦0.1 | ≦1 |
| 29 | ≦0.1 | ≦0.1 |
| 30 | ≦0.01 | ≦0.1 |
| 31 | ≦0.01 | ≦0.1 |
| 32 | ≦0.1 | ≦1 |
| 33 | ≦10 | ≦10 |
| 34 | ≦10 | ≦100 |
| 35 | ≦10 | ≦10 |
| 36 | ≦0.1 | ≦10 |
| 37 | ≦0.1 | ≦1 |
| 38 | ≦0.1 | ≦1 |
| 39 | ≦0.1 | ≦1 |
| 40 | ≦0.1 | ≦10 |
| 41 | ≦0.1 | ≦1 |
| 42 | ≦0.1 | ≦0.1 |
| 43 | ≦0.1 | ≦1 |
| 44 | ≦1 | ≦1 |
| 45 | ≦10 | ≦10 |
| 46 | ≦0.1 | ≦1 |
| 47 | ≦0.1 | ≦1 |
| 48 | ≦0.1 | ≦0.1 |
| 49 | ≦0.1 | ≦0.1 |
| 50 | ≦0.1 | ≦1 |
| 51 | ≦1 | ≦1 |
| 52 | ≦0.1 | ≦1 |
| 53 | ≦10 | ≦100 |
| 54 | ≦1 | ≦1 |
| 55 | ≦1 | ≦10 |
| 56 | ≦1 | ≦0.1 |
| 57 | ≦10 | ≦100 |
| 58 | ≦0.1 | ≦1 |
| 59 | ≦10 | ≦100 |
| 60 | ≦1 | ≦1 |
| 61 | ≦10 | ≦10 |
| 62 | ≦10 | ≦10 |
| 63 | ≦10 | ≦100 |
| 64 | ≦10 | ≦10 |
| 65 | ≦10 | ≦10 |
| 66 | ≦10 | ≦10 |
| 67 | ≦1 | ≦10 |
| 68 | ≦0.01 | ≦0.1 |
| 69 | ≦10 | ≦10 |
| 70 | ≦10 | ≦100 |
| 71 | ≦0.1 | ≦1 |
| 72 | ≦1 | ≦10 |
| 73 | ≦1 | ≦1 |
| 74 | ≦10 | ≦1000 |
| 75 | ≦1 | ≦1 |
| 76 | ≦0.001 | ≦0.1 |
| 77 | ≦1 | ≦10 |
| 78 | ≦1 | ≦10 |
| 79 | ≦10 | ≦10 |
| 80 | ≦1 | ≦1 |
| 81 | ≦0.1 | ≦1 |
| 82 | ≦1 | ≦1 |
| 83 | ≦1 | ≦1 |
| 84 | ≦1 | ≦1 |
| 85 | ≦1 | ≦1 |
| 86 | ≦1 | ≦1 |
| 87 | ≦0.1 | ≦0.1 |
| 88 | ≦0.1 | ≦0.1 |
| 89 | ≦0.1 | ≦1 |
| 90 | ≦1 | ≦1 |
| 91 | ≦10 | ≦10 |
| 92 | ≦1 | ≦1 |
| 93 | ≦1 | ≦10 |
| 94 | ≦10 | ≦100 |
| 95 | ≦0.1 | ≦0.1 |
| 96 | ≦1 | ≦10 |

We claim:

1. A 4-Benzylaminoquinoline of formula (I)

(I)

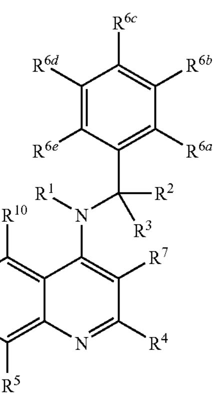

wherein $R^1$ is hydrogen, $C_1$-$C_6$-alkyl or $C_6$-$C_{12}$-aryl;

$R^2$, $R^3$ are independently hydrogen, $C_1$-$C_6$-alkyl, substituted $C_1$-$C_4$-alkyl, $C_3$-$C_{12}$-cycloalkyl, $C_6$-$C_{12}$-aryl, aminocarbonyl, amino or optionally substituted $C_3$-$C_{12}$-heterocyclyl;

$R^4$ is $C_1$-$C_6$-alkyl, halogenated $C_1$-$C_6$-alkyl, $C_1$-$C_6$-alkoxy, di-($C_1$-$C_6$-alkyl)amino, $C_6$-$C_{12}$-arylamino or sulfonylamino;

$R^5$ is hydrogen, halogen, $C_1$-$C_6$-alkyl, hydroxy, $C_1$-$C_6$-alkoxy, substituted $C_1$-$C_4$-alkoxy, $C_6$-$C_{12}$-aryloxy, $C_6$-$C_{12}$-heteroaryloxy, $C_1$-$C_6$-alkylthio, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, (optionally substituted $C_6$-$C_{12}$-aryl)aminosulfonyl, amino, substituted amino or optionally substituted $C_3$-$C_{12}$-heterocyclyl;

$R^{6a}$, $R^{6b}$, $R^{6c}$, $R^{6d}$, $R^{6e}$ are independently hydrogen, halogen, $C_1$-$C_6$-alkyl, halogenated $C_1$-$C_4$-alkyl, $C_1$-$C_4$-hydroxyalkyl, $C_1$-$C_6$-alkoxycarbonyl, (halogenated $C_1$-$C_4$-alkoxy) carbonyl, cyano, $C_1$-$C_6$-alkoxy, halogenated $C_1$-$C_4$-alkoxy, optionally substituted $C_6$-$C_{12}$-aryl, $C_1$-$C_4$-alkylthio, (halogenated $C_1$-$C_4$-alkyl)thio, nitro, amino, $C_1$-$C_6$-alkylamino, (halogenated $C_1$-$C_6$-alkyl) amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl)carbonylamino, $C_1$-$C_6$-alkylsulfonylamino, (halogenated $C_1$-$C_4$-alkyl) sulfonylamino or $C_6$-$C_{12}$-arylsulfonylamino; or $R^{6a}$, $R^2$ together are optionally substituted $C_1$-$C_4$-alkylene; or $R^{6a}$ and $R^{6b}$ or $R^{6b}$ and $R^{6c}$ together with the carbon atoms to which they are attached form an anellated aryl ring; or together are $C_1$-$C_2$-alkylenedioxo; and $R^7$, $R^8$, $R^9$, $R^{10}$ are independently hydrogen, halogen, $C_1$-$C_6$-alkyl or $C_1$-$C_6$-alkoxy, or a physiologically tolerated salt thereof, provided that the following compounds and the physiologically tolerated salts thereof are excluded:

a) 4'-[[(2-methyl-4-quinolinyl)amino]methyl]-[1,1'-biphenyl]-2-carboxylic acid, 1,1-dimethylethyl ester
b) 2-methyl-N-[[2'-[1-(triphenylmethyl)-1H-tetrazol-5-yl][1,1'-biphenyl]-4-yl]methyl]-4-quinolinamine,
c) 2-methyl-N-[[3'-(1H-tetrazol-5-yl)[1,1'-biphenyl]-4-yl]methyl]-4-quinolinamine,
d) 4'-[[(2-methyl-4-quinolinyl)amino]methyl]-[1,1'-biphenyl]-2-carboxylic acid,
e) 4'-[[(2-methyl-4-quinolinyl)amino]methyl]-[1,1'-biphenyl]-3-carboxylic acid, 1,1-dimethylethyl ester
f) 2-methyl-N-[[2'-(1H-tetrazol-5-yl)[1,1'-biphenyl]-4-yl]methyl]-4-quinolinamine,
g) 4'-[[(8-methoxy-2-methyl-4-quinolinyl)amino]methyl]-[1,1'-biphenyl]-2-carboxylic acid,
h) 8-methoxy-2-methyl-N-[[2'-(1H-tetrazol-5-yl)[1,1'-biphenyl]-4-yl]methyl]-4-quinolinamine,
i) 4'-[[(2-methyl-4-quinolinyl)amino]methyl]-N-(methylsulfonyl)-[1,1'-biphenyl]-2-carboxamide,
j) 4'-[[(2-methyl-4-quinolinyl)amino]methyl]-[1,1'-biphenyl]-2-carboxylic acid,
k) 4'-[[(2-methyl-4-quinolinyl)amino]methyl]-[1,1'-biphenyl]-2-carboxylic acid, methyl ester
l) N-[(2-methylphenyl)methyl]-8-methoxy-2-methyl-4-quinolinamine,
m) N-[(2-methoxyphenyl)methyl]-8-methoxy-2-methyl-4-quinolinamine,
n) N-[(2-ethylphenyl)methyl]-8-methoxy-2-methyl-4-quinolinamine,
o) N-[(2-bromophenyl)methyl]-8-methoxy-2-methyl-4-quinolinamine,
p) N-[(2,6-dichlorophenyl)methyl]-8-methoxy-2-methyl-4-quinolinamine,
q) N-[(2,6-dimethoxyphenyl)methyl]-8-methoxy-2-methyl-4-quinolinamine,
r) N-[(2,6-dimethylphenyl)methyl]-8-methoxy-2-methyl-4-quinolinamine,
s) N-[(2,3-dimethylphenyl)methyl]-8-methoxy-2-methyl-4-quinolinamine,
t) N-[(2,4-dimethylphenyl)methyl]-8-methoxy-2-methyl-4-quinolinamine,
u) N-[(2,5-dimethylphenyl)methyl]-8-methoxy-2-methyl-4-quinolinamine,
v) N-[(2-chlorophenyl)methyl]-8-methoxy-2-methyl-4-quinolinamine,
w) N-[(2-fluorophenyl)methyl]-8-methoxy-2-methyl-4-quinolinamine,
x) N-[(2-chloro-6-fluorophenyl)methyl]-8-methoxy-2-methyl-4-quinolinamine,
y) N-[(2,6-difluorophenyl)methyl]-8-methoxy-2-methyl-4-quinolinamine,
z) N-[[2-(trifluoromethyl)phenyl]methyl]-8-methoxy-2-methyl-4-quinolinamine,
aa) 4-[[(8-methoxy-2-methyl-4-quinolinyl)amino]methyl]-3-methyl-phenol,
ab) 4-[(p-chlorobenzyl)amino]-quinaldine,
ac) N-[(1S)-1-phenylethyl]-2-methyl-4-quinolinamine,
ad) N-(phenylmethyl)-2-methyl-4-quinolinamine,
ae) 4-[[1-(3,4-dimethoxyphenyl)hexyl]amino]-2-methyl-8-quinolinol,
af) 4-[[1-(2-hexyl-4,5-dimethoxyphenyl)ethyl]amino]-2-methyl-8-quinolinol,
ag) 4-[[1-(3,4-dimethoxyphenyl)hexyl]amino]-2-methyl-8-quinolinol,
ah) 4-[[1-(2-hexyl-4,5-dimethoxyphenyl)ethyl]amino]-2-methyl-4-quinolinol,
ai) N-[1-(3,4-dimethoxyphenyl)hexyl]-8-methoxy-2-methyl-4-quinolinamine, or
aj) N-[1-(2-hexyl-4,5-dimethoxyphenyl)ethyl]-8-methoxy-2-methyl-4-quinolinamine.

2. The compound of claim 1, wherein $R^1$ is hydrogen.

3. The compound of claim 1, wherein $R^2$ is hydrogen or $C_1$-$C_3$-alkyl.

4. The compound of claim 1, wherein $R^3$ is $C_1$-$C_1$-alkyl substituted with amino, $C_1$-$C_4$ alkylamino, di-$C_1$-$C_4$-alkylamino, ($C_6$-$C_{12}$-aryl-$C_1$-$C_2$-alkyl)amino or $C_3$-$C_{12}$-heterocyclyl.

5. The compound of claim 1, wherein $R^4$ is methyl or dimethylamino.

6. The compound of claim 1, wherein $R^5$ is hydrogen or halogen.

7. The compound of claim 1, wherein $R^5$ is hydroxy, $C_1$-$C_6$-alkoxy, halogenated $C_1$-$C_4$-alkoxy, $C_6$-$C_1$-aryloxy or $C_6$-$C_{12}$-heteroaryloxy.

8. The compound of claim 1, wherein $R^5$ is a group of the formula (II):

$$-A^1-A^2-A^3-R^{5a} \quad (II)$$

wherein $A^1$ is O, $NR^{5b}$;

$A^2$ is optionally substituted $C_1$-$C_4$-alkylene;

$A^3$ is O, $NR^{5b}$;

$R^5$ is hydrogen, $C_1$-$C_4$-alkyl, $C_1$-$C_4$-alkylcarbonyl, $C_6$-$C_{12}$-arylcarbonyl, $C_1$-$C_6$-alkoxycarbonyl, halogenated $C_1$-$C_4$-alkoxycarbonyl, $C_6$-$C_{12}$-aryloxycarbonyl, $C_1$-$C_6$-alkylaminocarbonyl, (halogenated $C_1$-$C_4$-alkyl) aminocarbonyl, $C_6$-$C_{12}$-arylaminocarbonyl, $C_1$-$C_6$-alkylsulfonyl, (halogenated $C_1$-$C_6$-alkyl) sulfonyl, $C_6$-$C_{12}$-arylsulfonyl, ($C_6$-$C_{12}$-aryl-$C_1$-$C_4$-alkyl)sulfonyl, $C_3$-$C_{12}$-heterocyclylsulfonyl or $C_6$-$C_{12}$-aryl; and $R^{5b}$ is hydrogen or $C_1$-$C_4$-alkyl; or $R^{5a}$ and $R^{5b}$ together with the nitrogen atom to which they are attached are $C_3$-$C_{12}$-heterocyclyl.

9. The compound of claim 1, wherein $R^5$ is $C_1$-$C_4$-alkoxy substituted with $C_1$-$C_6$-alkoxy, amino, di-$C_1$-$C_6$-alkylamino, $C_1$-$C_6$-alkylcarbonylamino, $C_6$-$C_{12}$-arylcarbonylamino, $C_1$-$C_6$-alkoxycarbonylamino, $C_1$-$C_{12}$-heterocyclyl, $C_1$-$C_6$-alkylsulfonylamino, (halogenated $C_1$-$C_4$ alkyl)sulfonylamino, $C_6$-$C_{12}$-arylsulfonylamino, ($C_6$-$C_{12}$-aryl-$C_1$-$C_4$-alkyl)sulfonylamino, $C_3$-$C_1$-heterocyclylsulfonylamino or $C_6$-$C_{12}$-aryl.

10. The compound of claim 1, wherein $R^5$ is $C_1$-$C_6$-alkylthio, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl or (optionally substituted $C_6$-$C_{12}$-aryl)aminosulfonyl.

11. The compound of claim 1, wherein $R^5$ is amino.

12. The compound of claim 1, wherein $R^5$ is $C_1$-$C_6$-alkylamino, di-$C_1$-$C_6$-alkylamino, $C_1$-$C_6$-alkylcarbonylamino, $C_6$-$C_{12}$-arylcarbonylamino, $C_1$-$C_6$-alkylsulfonylamino, $C_6$-$C_{12}$ arylsulfonylamino, di-($C_1$-$C_6$-alkylsulfonyl)amino or optionally substituted $C_3$-$C_{12}$-heterocyclyl.

13. The compound of claim 1, wherein at least one of $R^{6a}$, $R^{6b}$, $R^{6c}$, $R^{6d}$, or $R^{6e}$ is different from hydrogen.

14. The compound of claim 13, wherein at least one of $R^{6a}$, $R^{6b}$, $R^{6c}$, $R^{6d}$, or $R^{6e}$ is halogen, $C_1$-$C_4$-hydroxyalkyl, cyano or nitro.

15. The compound of claim 1, wherein $R^7$, $R^8$, $R^9$, and $R^{10}$ are all hydrogen.

16. A 4-Benzylaminoquinoline of formula (I)

(I)

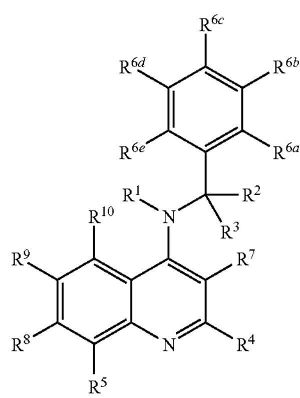

wherein $R^1$ is hydrogen;

$R^2$ is hydrogen, $C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, ($C_6$-$C_{12}$-aryl-$C_1$-$C_4$-alkyl)amino-$C_1$-$C_4$-alkyl, $C_3$-$C_{12}$-heterocyclyl-$C_1$-$C_4$-alkyl, $C_3$-$C_{12}$-cycloalkyl, $C_6$-$C_{12}$-aryl, aminocarbonyl or $C_3$-$C_{12}$-heterocyclyl;

$R^3$ is hydrogen;

$R^4$ is methyl or dimethylamino;

$R^5$ is hydrogen, halogen, $C_1$-$C_6$-alkyl, hydroxy, $C_1$-$C_6$-alkoxy, halogenated $C_1$-$C_4$-alkoxy, $C_1$-$C_6$-alkoxy-$C_1$-$C_4$-alkoxy, amino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_3$-$C_{12}$-heterocyclyl-$C_1$-$C_4$-alkoxy, $C_1$-$C_6$-alkylsulfonylamino-$C_1$-$C_4$-alkoxy, (halogenated $C_1$-$C_4$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_4$-alkyl)sulfonylamino-$C_1$-$C_4$-alkoxy, $C_1$-$C_{12}$-heterocyclylsulfonylamino-$C_1$-$C_4$-alkoxy, $C_6$-$C_{12}$-aryl-$C_1$-$C_4$-alkoxy, $C_6$-$C_{12}$-aryloxy, $C_6$-$C_{12}$-heteroaryloxy, $C_1$-$C_6$-alkylthio, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, (optionally substituted $C_6$-$C_{12}$-aryl)aminosulfonyl, amino, $C_1$-$C_6$-alkylamino, di-$C_1$-$C_6$-alkylamino, $C_1$-$C_6$-alkylcarbonylamino, $C_6$-$C_1$-arylcarbonylamino, $C_1$-$C_6$-alkylsulfonylamino, $C_6$-$C_{12}$-arylsulfonylamino, di-($C_1$-$C_6$-alkylsulfonyl)amino or optionally substituted $C_3$-$C_{12}$-heterocyclyl;

$R^{6a}$, $R^{6e}$ are hydrogen;

$R^{6b}$, $R^{6c}$, $R^{6d}$ are independently hydrogen, halogen, $C_1$-$C_6$-alkyl, halogenated $C_1$-$C_4$-alkyl, $C_1$-$C_6$-alkoxycarbonyl, $C_1$-$C_6$-alkoxy, halogenated $C_1$-$C_4$-alkoxy, halogenated $C_1$-$C_4$-alkylthio, nitro, at least one of $R^{6b}$, $R^{6c}$, $R^{6d}$ being different from hydrogen; and $R^7$, $R^8$, $R^9$, $R^{10}$ are all hydrogen, or a physiologically tolerated acid addition salt thereof, provided that 4-[(p-chlorobenzyl)amino]-quinaldine is excluded.

17. A pharmaceutical composition comprising a carrier and the compound of claim 1.

18. A method for treating a neurologic disorder selected from the group consisting of dementia, cognitive impairment, and attention deficit disorder, or a psychiatric disorder selected from the group consisting of an anxiety disorder, a mood disorder, a bipolar disorder, schizophrenia, and a psychotic disorder, the method comprising administering to a patient in need thereof a therapeutically effective amount of a 4-benzylaminoquinoline of formula (I)

(I)

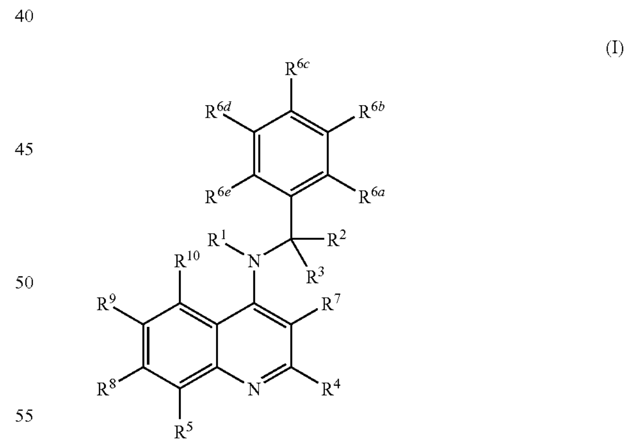

wherein $R^1$ is hydrogen, $C_1$-$C_6$-alkyl or $C_6$-$C_{12}$-aryl;

$R^2$, $R^3$ are independently hydrogen, $C_1$-$C_6$-alkyl, substituted $C_1$-$C_4$-alkyl, $C_3$-$C_{12}$-cycloalkyl, $C_6$-$C_{12}$-aryl, aminocarbonyl, amino or optionally substituted $C_3$-$C_{12}$-heterocyclyl;

$R^4$ is $C_1$-$C_6$-alkyl, halogenated $C_1$-$C_6$-alkyl, $C_1$-$C_6$-alkoxy, di-($C_1$-$C_6$-alkyl)amino, $C_6$-$C_{12}$-arylamino or sulfonylamino;

$R^5$ is hydrogen, halogen, $C_1$-$C_6$-alkyl, hydroxy, $C_1$-$C_6$-alkoxy, substituted $C_1$-$C_4$-alkoxy, $C_6$-$C_{12}$-aryloxy, $C_6$-$C_{12}$-heteroaryloxy, $C_1$-$C_6$-alkylthio, $C_1$-$C_6$-alkylsulfinyl, $C_1$-$C_6$-alkylsulfonyl, aminosulfonyl, $C_1$-$C_6$-alkylaminosulfonyl, di-$C_1$-$C_6$-alkylaminosulfonyl, (optionally substituted $C_6$-$C_{12}$-aryl)aminosulfonyl, amino, substituted amino or optionally substituted $C_3$-$C_{12}$-heterocyclyl;

$R^{6a}$, $R^{6b}$, $R^{6c}$, $R^{6d}$, $R^{6e}$ are independently hydrogen, halogen, $C_1$-$C_6$-alkyl, halogenated $C_1$-$C_4$-alkyl, $C_1$-$C_4$ hydroxyalkyl, $C_1$-$C_6$-alkoxycarbonyl, (halogenated $C_1$-$C_4$-alkoxy)carbonyl, cyano, $C_1$-$C_6$-alkoxy, halogenated $C_1$-$C_4$-alkoxy, optionally substituted $C_6$-$C_{12}$-aryl, $C_1$-$C_4$-alkylthio, (halogenated $C_1$-$C_4$-alkyl)thio, nitro, amino, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_4$-alkyl) carbonylamino, $C_1$-$C_6$-alkylsulfonylamino, (halogenated $C_1$-$C_4$-alkyl)sulfonylamino or $C_6$-$C_{12}$-arylsulfonylamino; or $R^{6a}$, $R^2$ together are optionally substituted $C_1$-$C_4$-alkylene; or $R^{6a}$ and $R^{6b}$ or $R^{6b}$ and $R^{6c}$ together with the carbon atoms to which they are attached form an anellated aryl ring; or together are $C_1$-$C_2$-alkylenedioxo; and $R^7$, $R^8$, $R^9$, $R^{10}$ are independently hydrogen, halogen, $C_1$-$C_6$-alkyl or $C_1$-$C_6$-alkoxy, or a physiologically tolerated salt thereof.

* * * * *

UNITED STATES PATENT AND TRADEMARK OFFICE

CERTIFICATE OF CORRECTION

PATENT NO. : 8,420,670 B2
APPLICATION NO. : 12/666629
DATED : April 16, 2013
INVENTOR(S) : Amberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 441 days.

Signed and Sealed this
Twenty-first Day of January, 2014

Michelle K. Lee
*Deputy Director of the United States Patent and Trademark Office*